US011779742B2

(12) United States Patent
Chalekian et al.

(10) Patent No.: US 11,779,742 B2
(45) Date of Patent: Oct. 10, 2023

(54) INTRODUCER WITH HEMOSTASIS MECHANISM

(71) Applicant: Neovasc Tiara Inc., Richmond (CA)

(72) Inventors: Aaron J. Chalekian, Savage, MN (US); Kellen Bodell, Plymouth, MN (US); Eric Soun-Sang Fung, Vancouver (CA); Karen Tsoek-Ji Wong, Richmond (CA)

(73) Assignee: Neovasc Tiara Inc., Richmond (CA)

( * ) Notice: Subject to any disclaimer, the term of this patent is extended or adjusted under 35 U.S.C. 154(b) by 307 days.

(21) Appl. No.: 16/879,416

(22) Filed: May 20, 2020

(65) Prior Publication Data

US 2020/0368514 A1    Nov. 26, 2020

Related U.S. Application Data

(60) Provisional application No. 62/850,179, filed on May 20, 2019.

(51) Int. Cl.
*A61M 39/06* (2006.01)
*A61M 39/20* (2006.01)

(52) U.S. Cl.
CPC ............ *A61M 39/06* (2013.01); *A61M 39/20* (2013.01); *A61M 2039/062* (2013.01); *A61M 2039/068* (2013.01); *A61M 2039/0626* (2013.01); *A61M 2210/125* (2013.01)

(58) Field of Classification Search
CPC .................. A61M 39/06; A61M 39/20; A61M 2039/062; A61M 2039/0626; A61M 2039/068; A61M 2210/125; A61M 39/0613; A61M 2039/0633; A61M 2039/0673; A61M 39/0693; A61M 2210/12; A61M 2210/127; A61M 39/22; A61M 39/227; A61M 39/228; A61M 39/28
See application file for complete search history.

(56) References Cited

U.S. PATENT DOCUMENTS

| 2,967,856 | A | 1/1961 | Coover, Jr. et al. |
| 4,204,283 | A | 5/1980 | Bellhouse et al. |
| 4,978,341 | A | 12/1990 | Niederhauser |

(Continued)

FOREIGN PATENT DOCUMENTS

| CA | 3007660 A1 | 6/2017 |
| CA | 2874219 C | 7/2020 |

(Continued)

OTHER PUBLICATIONS

U.S. Appl. No. 16/812,865, filed Mar. 9, 2020, Transseptal Delivery System.

(Continued)

*Primary Examiner* — Jason E Flick
(74) *Attorney, Agent, or Firm* — Schwegman Lundberg & Woessner, P.A.

(57) ABSTRACT

An introducer sheath includes an elongate shaft having a proximal end, a distal end and a lumen extending therebetween. An actuatable hemostasis valve in a hub is adjacent the proximal end of the elongate shaft and may be used to prevent blood from escaping from the elongate shaft. The introducer sheath may also have a a self-expanding funnel adjacent the distal end of the elongate shaft.

38 Claims, 29 Drawing Sheets

(56) References Cited

U.S. PATENT DOCUMENTS

| | | | |
|---|---|---|---|
| 5,415,664 A | 5/1995 | Pinchuk | |
| 5,897,533 A | 4/1999 | Glickman | |
| 5,928,281 A | 7/1999 | Huynh et al. | |
| 6,074,417 A | 6/2000 | Peredo | |
| 6,221,057 B1 * | 4/2001 | Schwartz | A61M 39/0613 |
| | | | 604/537 |
| 6,276,661 B1 | 8/2001 | Laird | |
| 6,312,465 B1 | 11/2001 | Griffin et al. | |
| 6,629,534 B1 | 10/2003 | St. Goar et al. | |
| 6,652,578 B2 | 11/2003 | Bailey et al. | |
| 7,018,406 B2 | 3/2006 | Seguin et al. | |
| 7,329,278 B2 | 2/2008 | Seguin et al. | |
| 7,338,520 B2 | 3/2008 | Bailey et al. | |
| 7,435,257 B2 | 10/2008 | Lashinski et al. | |
| 7,442,204 B2 | 10/2008 | Schwammenthal et al. | |
| 7,455,689 B2 | 11/2008 | Johnson | |
| 7,637,945 B2 | 12/2009 | Solem et al. | |
| 7,637,946 B2 | 12/2009 | Solem et al. | |
| 7,799,072 B2 | 9/2010 | Greenberg | |
| 7,914,569 B2 | 3/2011 | Nguyen et al. | |
| 7,914,575 B2 | 3/2011 | Guyenot et al. | |
| 7,972,377 B2 | 7/2011 | Lane | |
| 8,092,520 B2 | 1/2012 | Quadri | |
| 8,226,710 B2 | 7/2012 | Nguyen et al. | |
| 8,337,541 B2 | 12/2012 | Quadri et al. | |
| 8,398,708 B2 | 3/2013 | Meiri et al. | |
| 8,403,983 B2 | 3/2013 | Quadri et al. | |
| 8,408,214 B2 | 4/2013 | Spenser | |
| 8,414,644 B2 | 4/2013 | Quadri et al. | |
| 8,449,599 B2 | 5/2013 | Chau et al. | |
| 8,579,964 B2 | 11/2013 | Lane et al. | |
| 8,652,203 B2 | 2/2014 | Quadri et al. | |
| 8,795,356 B2 | 8/2014 | Quadri et al. | |
| 10,631,984 B2 | 4/2020 | Nyuli et al. | |
| 2002/0005891 A1 | 5/2002 | Hermann et al. | |
| 2004/0181238 A1 | 9/2004 | Zarbatany et al. | |
| 2005/0075727 A1 | 4/2005 | Wheatley | |
| 2005/0228475 A1 | 10/2005 | Keeble et al. | |
| 2006/0020334 A1 | 1/2006 | Lashinski et al. | |
| 2006/0259136 A1 | 11/2006 | Nguyen et al. | |
| 2006/0293698 A1 | 12/2006 | Douk | |
| 2006/0293745 A1 | 12/2006 | Carpentier et al. | |
| 2007/0016286 A1 | 1/2007 | Herrmann et al. | |
| 2007/0050020 A1 | 3/2007 | Spence | |
| 2008/0065011 A1 | 3/2008 | Marchand et al. | |
| 2008/0071362 A1 | 3/2008 | Tuval et al. | |
| 2008/0071363 A1 | 3/2008 | Tuval et al. | |
| 2008/0071366 A1 | 3/2008 | Tuval et al. | |
| 2008/0221672 A1 | 9/2008 | Lamphere | |
| 2008/0228201 A1 | 9/2008 | Zarbatany et al. | |
| 2008/0255660 A1 | 10/2008 | Guyenot et al. | |
| 2009/0012602 A1 | 1/2009 | Quadri | |
| 2009/0062908 A1 | 3/2009 | Bonhoeffer et al. | |
| 2009/0171447 A1 | 7/2009 | Von Segesser et al. | |
| 2009/0216314 A1 | 8/2009 | Quadri | |
| 2009/0234428 A1 | 9/2009 | Snow et al. | |
| 2009/0234443 A1 | 9/2009 | Ottma et al. | |
| 2009/0259306 A1 | 10/2009 | Rowe | |
| 2009/0276040 A1 | 11/2009 | Rowe et al. | |
| 2009/0306768 A1 | 12/2009 | Quadri | |
| 2009/0318871 A1 | 12/2009 | Zarbatany et al. | |
| 2010/0036479 A1 | 2/2010 | Hill et al. | |
| 2010/0082094 A1 | 4/2010 | Quadri et al. | |
| 2010/0094411 A1 | 4/2010 | Tuval et al. | |
| 2010/0131054 A1 | 5/2010 | Tuval et al. | |
| 2010/0168839 A1 | 7/2010 | Braido et al. | |
| 2010/0268332 A1 | 10/2010 | Tuval et al. | |
| 2010/0280495 A1 | 11/2010 | Paul et al. | |
| 2010/0298931 A1 | 11/2010 | Quadri et al. | |
| 2011/0015731 A1 | 1/2011 | Carpentier et al. | |
| 2011/0022157 A1 | 1/2011 | Essinger et al. | |
| 2011/0137338 A1 | 6/2011 | Phillips | |
| 2011/0137397 A1 | 6/2011 | Chau et al. | |
| 2011/0178597 A9 | 7/2011 | Navia et al. | |
| 2011/0202128 A1 | 8/2011 | Duffy | |
| 2011/0208290 A1 | 8/2011 | Straubinger et al. | |
| 2011/0208297 A1 | 8/2011 | Tuval et al. | |
| 2011/0208298 A1 | 8/2011 | Tuval et al. | |
| 2011/0224785 A1 | 9/2011 | Hacohen | |
| 2011/0313515 A1 | 12/2011 | Quadri et al. | |
| 2011/0319989 A1 | 12/2011 | Lane et al. | |
| 2012/0078353 A1 | 3/2012 | Quadri et al. | |
| 2012/0101571 A1 | 4/2012 | Thambar et al. | |
| 2012/0179239 A1 | 7/2012 | Quadri | |
| 2012/0215303 A1 | 8/2012 | Quadri et al. | |
| 2013/0053950 A1 | 2/2013 | Rowe et al. | |
| 2013/0110227 A1 | 5/2013 | Quadri et al. | |
| 2013/0131788 A1 | 5/2013 | Quadri et al. | |
| 2013/0131793 A1 | 5/2013 | Quadri et al. | |
| 2013/0138203 A1 | 5/2013 | Quadri | |
| 2013/0138207 A1 | 5/2013 | Quadri et al. | |
| 2013/0144378 A1 | 6/2013 | Quadri et al. | |
| 2013/0144380 A1 | 6/2013 | Quadri et al. | |
| 2013/0144381 A1 | 6/2013 | Quadri et al. | |
| 2013/0184813 A1 | 7/2013 | Quadri et al. | |
| 2013/0274870 A1 | 10/2013 | Lombardi et al. | |
| 2014/0155990 A1 | 6/2014 | Nyuli et al. | |
| 2014/0172085 A1 | 6/2014 | Quadri et al. | |
| 2014/0172086 A1 | 6/2014 | Quadri et al. | |
| 2014/0200649 A1 | 7/2014 | Essinger et al. | |
| 2014/0277390 A1 | 9/2014 | Ratz et al. | |
| 2014/0277422 A1 | 9/2014 | Ratz et al. | |
| 2014/0277427 A1 | 9/2014 | Ratz et al. | |
| 2015/0112279 A1 * | 4/2015 | Myers | A61M 39/0613 |
| | | | 604/256 |
| 2015/0127092 A1 | 5/2015 | Straubinger et al. | |
| 2015/0306358 A1 | 10/2015 | Duffy | |
| 2015/0342736 A1 | 12/2015 | Rabito et al. | |
| 2016/0296690 A1 | 10/2016 | Kume et al. | |
| 2017/0112513 A1 * | 4/2017 | Marchand | A61F 2/014 |
| 2017/0156857 A1 * | 6/2017 | Bishop | A61F 2/2436 |
| 2017/0165064 A1 | 6/2017 | Nyuli et al. | |
| 2020/0205972 A1 | 7/2020 | Nyuli et al. | |
| 2020/0281720 A1 | 9/2020 | Jackson et al. | |

FOREIGN PATENT DOCUMENTS

| | | |
|---|---|---|
| CN | 101553190 A | 10/2009 |
| CN | 103118630 A | 5/2013 |
| CN | 107206219 | 9/2017 |
| CN | 108601645 A | 9/2018 |
| DE | 10103955 B4 | 11/2001 |
| DE | 10033858 B4 | 1/2002 |
| DE | 102006052564 B3 | 12/2007 |
| DE | 102006013113 B4 | 12/2008 |
| DE | 102008015781 B4 | 9/2011 |
| DE | 102010051632 B4 | 9/2013 |
| DE | 102005032974 B4 | 11/2013 |
| DE | 202013011734 U1 | 4/2014 |
| DE | 102005052628 B4 | 6/2014 |
| DE | 10301026 B4 | 10/2014 |
| DE | 212013000104 U1 | 11/2014 |
| DE | 102008012438 B4 | 12/2014 |
| DE | 102011107551 B4 | 5/2015 |
| DE | 102011054176 B4 | 2/2016 |
| DE | 102014114762 B3 | 3/2016 |
| DE | 102013208038 B4 | 9/2016 |
| DE | 102010012677 B4 | 8/2017 |
| DE | 202011110951 U1 | 10/2017 |
| DE | 202011110985 U1 | 12/2017 |
| DE | 202016105963 U1 | 1/2018 |
| DE | 10394350 B4 | 5/2018 |
| DE | 102009024648 B4 | 5/2018 |
| DE | 102015206098 B4 | 9/2018 |
| DE | 10065824 B4 | 10/2018 |
| DE | 202017104793 U1 | 11/2018 |
| DE | 102011106928 B4 | 2/2019 |
| DE | 202016008737 U1 | 4/2019 |
| DE | 102013205519 B4 | 5/2019 |
| DE | 102008014730 B4 | 7/2019 |
| DE | 102018102940 B4 | 10/2019 |
| DE | 102009009158 B4 | 11/2020 |
| EP | 1077072 B1 | 11/2003 |
| EP | 1140244 B1 | 11/2003 |

(56) References Cited

FOREIGN PATENT DOCUMENTS

| | | | |
|---|---|---|---|
| EP | 1214106 B1 | 11/2003 |
| EP | 1143864 B1 | 2/2004 |
| EP | 1220651 B1 | 3/2004 |
| EP | 1265534 B1 | 6/2004 |
| EP | 1347785 B1 | 7/2004 |
| EP | 1245202 B1 | 8/2004 |
| EP | 1161204 B1 | 9/2004 |
| EP | 1266641 B1 | 10/2004 |
| EP | 1102567 B1 | 11/2004 |
| EP | 1117446 B1 | 11/2004 |
| EP | 1107710 B1 | 12/2004 |
| EP | 1121070 B1 | 12/2004 |
| EP | 1217966 B1 | 12/2004 |
| EP | 1233731 B1 | 12/2004 |
| EP | 1294318 B1 | 12/2004 |
| EP | 1237510 B1 | 1/2005 |
| EP | 1034753 B1 | 2/2005 |
| EP | 1259194 B1 | 2/2005 |
| EP | 1121069 B1 | 3/2005 |
| EP | 1143879 B1 | 3/2005 |
| EP | 1023879 B1 | 4/2005 |
| EP | 1339356 B1 | 4/2005 |
| EP | 1214022 B1 | 5/2005 |
| EP | 1318774 B1 | 5/2005 |
| EP | 1088529 B1 | 6/2005 |
| EP | 1171060 B1 | 6/2005 |
| EP | 1251803 B1 | 6/2005 |
| EP | 1259776 B1 | 6/2005 |
| EP | 1272123 B1 | 6/2005 |
| EP | 1049422 B1 | 7/2005 |
| EP | 1230901 B1 | 8/2005 |
| EP | 1335683 B1 | 8/2005 |
| EP | 1307246 B1 | 9/2005 |
| EP | 1267753 B1 | 10/2005 |
| EP | 1284688 B1 | 10/2005 |
| EP | 1343536 B1 | 10/2005 |
| EP | 1027020 B1 | 11/2005 |
| EP | 1152780 B1 | 11/2005 |
| EP | 1171059 B1 | 11/2005 |
| EP | 1237508 B1 | 11/2005 |
| EP | 1303234 B1 | 11/2005 |
| EP | 1328215 B1 | 11/2005 |
| EP | 1341487 B1 | 11/2005 |
| EP | 1392197 B1 | 11/2005 |
| EP | 1469797 B1 | 11/2005 |
| EP | 1255505 B1 | 12/2005 |
| EP | 1360942 B1 | 12/2005 |
| EP | 1322260 B1 | 1/2006 |
| EP | 1359870 B1 | 1/2006 |
| EP | 1237586 B1 | 2/2006 |
| EP | 1112043 B1 | 4/2006 |
| EP | 1309360 B1 | 4/2006 |
| EP | 1322259 B1 | 5/2006 |
| EP | 1124592 B1 | 6/2006 |
| EP | 1237516 B1 | 6/2006 |
| EP | 1098673 B1 | 7/2006 |
| EP | 1124591 B1 | 7/2006 |
| EP | 1083845 B1 | 8/2006 |
| EP | 1155666 B1 | 8/2006 |
| EP | 1463462 B1 | 8/2006 |
| EP | 1684671 A1 | 8/2006 |
| EP | 1519695 B1 | 9/2006 |
| EP | 1444993 B1 | 10/2006 |
| EP | 1117350 B1 | 11/2006 |
| EP | 1212011 B1 | 11/2006 |
| EP | 1261294 B1 | 11/2006 |
| EP | 1318775 B1 | 11/2006 |
| EP | 1429690 B1 | 11/2006 |
| EP | 1173111 B1 | 12/2006 |
| EP | 1239795 B1 | 12/2006 |
| EP | 1299049 B1 | 12/2006 |
| EP | 1487382 B1 | 12/2006 |
| EP | 1112044 B1 | 1/2007 |
| EP | 1482997 B1 | 1/2007 |
| EP | 1117352 B1 | 2/2007 |
| EP | 1128849 B1 | 2/2007 |
| EP | 1392666 B1 | 2/2007 |
| EP | 1474077 B1 | 2/2007 |
| EP | 1251805 B1 | 3/2007 |
| EP | 1117334 B1 | 4/2007 |
| EP | 1263484 B1 | 5/2007 |
| EP | 1313410 B1 | 5/2007 |
| EP | 1370200 B1 | 5/2007 |
| EP | 1560526 B1 | 6/2007 |
| EP | 1173117 B1 | 7/2007 |
| EP | 1434615 B1 | 7/2007 |
| EP | 1465546 B1 | 7/2007 |
| EP | 1499366 B1 | 7/2007 |
| EP | 1225948 B1 | 8/2007 |
| EP | 1819304 A2 | 8/2007 |
| EP | 1519962 B1 | 9/2007 |
| EP | 1337285 B1 | 10/2007 |
| EP | 1112042 B1 | 11/2007 |
| EP | 1148821 B1 | 11/2007 |
| EP | 1143882 B1 | 12/2007 |
| EP | 1330189 B1 | 12/2007 |
| EP | 1489996 B1 | 12/2007 |
| EP | 1296618 B1 | 1/2008 |
| EP | 1401356 B1 | 1/2008 |
| EP | 1629795 B1 | 1/2008 |
| EP | 1128786 B1 | 2/2008 |
| EP | 1616532 B1 | 2/2008 |
| EP | 1289447 B1 | 3/2008 |
| EP | 1895942 A2 | 3/2008 |
| EP | 1115353 B1 | 5/2008 |
| EP | 1330190 B1 | 5/2008 |
| EP | 1383448 B1 | 6/2008 |
| EP | 1251804 B1 | 7/2008 |
| EP | 1294310 B1 | 7/2008 |
| EP | 1313409 B1 | 7/2008 |
| EP | 1395202 B1 | 7/2008 |
| EP | 1395204 B1 | 7/2008 |
| EP | 1395205 B1 | 7/2008 |
| EP | 1423066 B1 | 7/2008 |
| EP | 1560545 B1 | 7/2008 |
| EP | 1605871 B1 | 7/2008 |
| EP | 1671608 B1 | 7/2008 |
| EP | 1690515 B1 | 7/2008 |
| EP | 1180987 B1 | 8/2008 |
| EP | 1337386 B1 | 8/2008 |
| EP | 1492579 B1 | 9/2008 |
| EP | 1524942 B1 | 9/2008 |
| EP | 1627091 B1 | 9/2008 |
| EP | 1827577 B1 | 9/2008 |
| EP | 1259195 B1 | 10/2008 |
| EP | 1704834 B1 | 10/2008 |
| EP | 1146835 B1 | 11/2008 |
| EP | 1498086 B1 | 11/2008 |
| EP | 1622548 B1 | 11/2008 |
| EP | 1235537 B1 | 12/2008 |
| EP | 1237509 B1 | 12/2008 |
| EP | 1355590 B1 | 12/2008 |
| EP | 1455680 B1 | 12/2008 |
| EP | 1472995 B1 | 12/2008 |
| EP | 1513474 B1 | 12/2008 |
| EP | 1562522 B1 | 12/2008 |
| EP | 1620042 B1 | 12/2008 |
| EP | 1690514 B1 | 12/2008 |
| EP | 1258232 B1 | 1/2009 |
| EP | 1420723 B1 | 1/2009 |
| EP | 1570809 B1 | 1/2009 |
| EP | 1395182 B1 | 2/2009 |
| EP | 1408882 B1 | 2/2009 |
| EP | 1482868 B1 | 2/2009 |
| EP | 1255510 B3 | 3/2009 |
| EP | 1330213 B1 | 3/2009 |
| EP | 1429651 B1 | 3/2009 |
| EP | 1610727 B1 | 4/2009 |
| EP | 1617788 B1 | 4/2009 |
| EP | 1634547 B1 | 4/2009 |
| EP | 1790318 B1 | 4/2009 |
| EP | 2040645 A1 | 4/2009 |
| EP | 1250165 B1 | 5/2009 |
| EP | 1842508 B1 | 6/2009 |

(56) References Cited

FOREIGN PATENT DOCUMENTS

| | | | |
|---|---|---|---|
| EP | 1968482 | B1 | 6/2009 |
| EP | 2072027 | A1 | 6/2009 |
| EP | 1343438 | B1 | 7/2009 |
| EP | 1406608 | B1 | 7/2009 |
| EP | 1509256 | B1 | 7/2009 |
| EP | 1626681 | B1 | 7/2009 |
| EP | 1723935 | B1 | 7/2009 |
| EP | 1803420 | B1 | 7/2009 |
| EP | 2073755 | A2 | 7/2009 |
| EP | 1401359 | B1 | 8/2009 |
| EP | 1411865 | B1 | 8/2009 |
| EP | 1485033 | B1 | 8/2009 |
| EP | 1581120 | B1 | 8/2009 |
| EP | 1620040 | B1 | 8/2009 |
| EP | 1684667 | B1 | 8/2009 |
| EP | 1872743 | B1 | 8/2009 |
| EP | 1100378 | B1 | 9/2009 |
| EP | 1198203 | B1 | 9/2009 |
| EP | 1370201 | B1 | 9/2009 |
| EP | 1408850 | B1 | 9/2009 |
| EP | 1472996 | B1 | 9/2009 |
| EP | 1478364 | B1 | 9/2009 |
| EP | 1653888 | B1 | 9/2009 |
| EP | 1785154 | B1 | 9/2009 |
| EP | 1881804 | B1 | 9/2009 |
| EP | 1903991 | B1 | 9/2009 |
| EP | 1418865 | B1 | 10/2009 |
| EP | 1561437 | B1 | 10/2009 |
| EP | 1615595 | B1 | 10/2009 |
| EP | 1353612 | B1 | 11/2009 |
| EP | 1348406 | B1 | 12/2009 |
| EP | 1370202 | B1 | 12/2009 |
| EP | 1603492 | B1 | 12/2009 |
| EP | 1670364 | B1 | 12/2009 |
| EP | 1759663 | B1 | 12/2009 |
| EP | 1994887 | B1 | 12/2009 |
| EP | 1615593 | B1 | 1/2010 |
| EP | 1643938 | B1 | 1/2010 |
| EP | 1863402 | B1 | 1/2010 |
| EP | 1943942 | B1 | 1/2010 |
| EP | 2010101 | B1 | 1/2010 |
| EP | 2081518 | B1 | 1/2010 |
| EP | 1703865 | B1 | 2/2010 |
| EP | 1276437 | B1 | 3/2010 |
| EP | 1276439 | B1 | 3/2010 |
| EP | 1411867 | B1 | 3/2010 |
| EP | 1458313 | B1 | 3/2010 |
| EP | 1520519 | B1 | 3/2010 |
| EP | 1648340 | B1 | 3/2010 |
| EP | 1682048 | B1 | 3/2010 |
| EP | 1773239 | B1 | 3/2010 |
| EP | 1935377 | B1 | 3/2010 |
| EP | 1994912 | B1 | 3/2010 |
| EP | 1154738 | B1 | 4/2010 |
| EP | 1531762 | B1 | 4/2010 |
| EP | 1600178 | B1 | 4/2010 |
| EP | 1626682 | B1 | 4/2010 |
| EP | 1511445 | B1 | 5/2010 |
| EP | 1198213 | B1 | 6/2010 |
| EP | 1250097 | B1 | 6/2010 |
| EP | 1272249 | B1 | 6/2010 |
| EP | 1978895 | B1 | 6/2010 |
| EP | 1572033 | B1 | 7/2010 |
| EP | 1968491 | B1 | 7/2010 |
| EP | 2019652 | B1 | 7/2010 |
| EP | 1610722 | B1 | 8/2010 |
| EP | 1682047 | B1 | 8/2010 |
| EP | 1952772 | B1 | 8/2010 |
| EP | 1427356 | B1 | 9/2010 |
| EP | 1631218 | B1 | 9/2010 |
| EP | 1765224 | B1 | 9/2010 |
| EP | 1871290 | B1 | 9/2010 |
| EP | 1895288 | B1 | 9/2010 |
| EP | 1895913 | B1 | 9/2010 |
| EP | 2014257 | B1 | 9/2010 |
| EP | 1176913 | B1 | 10/2010 |
| EP | 1178758 | B1 | 10/2010 |
| EP | 1248579 | B1 | 10/2010 |
| EP | 1913899 | B1 | 10/2010 |
| EP | 1259193 | B1 | 11/2010 |
| EP | 1928357 | B1 | 11/2010 |
| EP | 1968660 | B1 | 11/2010 |
| EP | 2249711 | A2 | 11/2010 |
| EP | 1408895 | B1 | 12/2010 |
| EP | 1465554 | B1 | 12/2010 |
| EP | 1732473 | B1 | 12/2010 |
| EP | 1768610 | B1 | 12/2010 |
| EP | 1827314 | B1 | 12/2010 |
| EP | 1940321 | B1 | 12/2010 |
| EP | 1964532 | B1 | 12/2010 |
| EP | 2078498 | B1 | 12/2010 |
| EP | 1600182 | B1 | 1/2011 |
| EP | 1617789 | B1 | 1/2011 |
| EP | 1663332 | B1 | 1/2011 |
| EP | 2147659 | B1 | 1/2011 |
| EP | 2268231 | A2 | 1/2011 |
| EP | 2273951 | A1 | 1/2011 |
| EP | 1187582 | B1 | 2/2011 |
| EP | 1450733 | B1 | 2/2011 |
| EP | 1803421 | B1 | 2/2011 |
| EP | 1833425 | B1 | 2/2011 |
| EP | 2029053 | B1 | 2/2011 |
| EP | 2068770 | B1 | 2/2011 |
| EP | 1441784 | B1 | 3/2011 |
| EP | 1534177 | B1 | 3/2011 |
| EP | 1893132 | B1 | 3/2011 |
| EP | 1951153 | B1 | 3/2011 |
| EP | 2289467 | A1 | 3/2011 |
| EP | 2299938 | A2 | 3/2011 |
| EP | 1359978 | B1 | 4/2011 |
| EP | 1667750 | B1 | 4/2011 |
| EP | 1718249 | B1 | 4/2011 |
| EP | 1903989 | B1 | 4/2011 |
| EP | 2018122 | B1 | 4/2011 |
| EP | 1610728 | B1 | 5/2011 |
| EP | 2105110 | B1 | 5/2011 |
| EP | 1347717 | B1 | 6/2011 |
| EP | 2331018 | A1 | 6/2011 |
| EP | 1347791 | B1 | 7/2011 |
| EP | 1862128 | B1 | 7/2011 |
| EP | 2120795 | B1 | 7/2011 |
| EP | 2229920 | B1 | 7/2011 |
| EP | 1637087 | B1 | 8/2011 |
| EP | 2153799 | B1 | 8/2011 |
| EP | 2247263 | B1 | 8/2011 |
| EP | 2349095 | | 8/2011 |
| EP | 2349097 | A1 | 8/2011 |
| EP | 2349098 | A1 | 8/2011 |
| EP | 2358307 | A1 | 8/2011 |
| EP | 1441672 | B1 | 9/2011 |
| EP | 1625832 | B1 | 9/2011 |
| EP | 2173279 | B1 | 9/2011 |
| EP | 2367505 | A1 | 9/2011 |
| EP | 2160150 | B1 | 10/2011 |
| EP | 2370138 | A2 | 10/2011 |
| EP | 1626679 | B1 | 11/2011 |
| EP | 1719476 | B1 | 11/2011 |
| EP | 1928355 | B1 | 11/2011 |
| EP | 2237747 | B1 | 11/2011 |
| EP | 2381895 | A2 | 11/2011 |
| EP | 2389121 | A1 | 11/2011 |
| EP | 1572031 | B1 | 12/2011 |
| EP | 1603493 | B1 | 12/2011 |
| EP | 1945109 | B1 | 12/2011 |
| EP | 1998688 | B1 | 12/2011 |
| EP | 2393442 | A2 | 12/2011 |
| EP | 2395944 | A1 | 12/2011 |
| EP | 1443877 | B1 | 1/2012 |
| EP | 2400922 | A1 | 1/2012 |
| EP | 1281375 | B1 | 2/2012 |
| EP | 1699501 | B1 | 2/2012 |
| EP | 1788984 | B1 | 2/2012 |
| EP | 1833415 | B1 | 2/2012 |
| EP | 1952785 | B1 | 2/2012 |

(56) References Cited

FOREIGN PATENT DOCUMENTS

| | | |
|---|---|---|
| EP | 2055266 B1 | 2/2012 |
| EP | 2205184 B1 | 2/2012 |
| EP | 2416736 A1 | 2/2012 |
| EP | 1337188 B1 | 3/2012 |
| EP | 1443974 B1 | 3/2012 |
| EP | 1542623 B1 | 3/2012 |
| EP | 1942835 B1 | 3/2012 |
| EP | 2074964 B1 | 3/2012 |
| EP | 2244661 B1 | 3/2012 |
| EP | 2273928 B1 | 3/2012 |
| EP | 2427144 A1 | 3/2012 |
| EP | 2429455 A1 | 3/2012 |
| EP | 1401336 B1 | 4/2012 |
| EP | 1749544 B1 | 4/2012 |
| EP | 2119417 B1 | 4/2012 |
| EP | 2152330 B1 | 4/2012 |
| EP | 2231069 B1 | 4/2012 |
| EP | 2437688 A1 | 4/2012 |
| EP | 2020958 B1 | 5/2012 |
| EP | 2192875 B1 | 5/2012 |
| EP | 2218425 B1 | 5/2012 |
| EP | 2445450 A2 | 5/2012 |
| EP | 1411847 B1 | 6/2012 |
| EP | 1727499 B1 | 6/2012 |
| EP | 2082690 B1 | 6/2012 |
| EP | 1740747 B1 | 7/2012 |
| EP | 1861044 B1 | 7/2012 |
| EP | 2052699 B1 | 7/2012 |
| EP | 2470121 A2 | 7/2012 |
| EP | 2471492 A1 | 7/2012 |
| EP | 1887975 B1 | 8/2012 |
| EP | 2000116 B1 | 8/2012 |
| EP | 2222247 B1 | 8/2012 |
| EP | 2486894 A1 | 8/2012 |
| EP | 1605870 B1 | 9/2012 |
| EP | 1887980 B1 | 9/2012 |
| EP | 2497445 A1 | 9/2012 |
| EP | 1740126 B1 | 10/2012 |
| EP | 1865889 B1 | 10/2012 |
| EP | 2033593 B1 | 10/2012 |
| EP | 2124824 B1 | 10/2012 |
| EP | 2139431 B1 | 10/2012 |
| EP | 2506777 A1 | 10/2012 |
| EP | 2512952 A2 | 10/2012 |
| EP | 1430853 B1 | 11/2012 |
| EP | 1928512 B1 | 11/2012 |
| EP | 2008615 B1 | 11/2012 |
| EP | 2088965 B1 | 11/2012 |
| EP | 2520249 A1 | 11/2012 |
| EP | 2522307 A1 | 11/2012 |
| EP | 1557138 B1 | 12/2012 |
| EP | 1924221 B1 | 12/2012 |
| EP | 2023859 B1 | 12/2012 |
| EP | 2250970 B1 | 12/2012 |
| EP | 2285317 B1 | 12/2012 |
| EP | 2536353 A1 | 12/2012 |
| EP | 2537486 A1 | 12/2012 |
| EP | 1494731 B1 | 1/2013 |
| EP | 1610752 B1 | 1/2013 |
| EP | 1796597 B1 | 1/2013 |
| EP | 1919397 B1 | 1/2013 |
| EP | 1942834 B1 | 1/2013 |
| EP | 2015709 B1 | 1/2013 |
| EP | 2079400 B1 | 1/2013 |
| EP | 2238947 B1 | 1/2013 |
| EP | 2241287 B1 | 1/2013 |
| EP | 2359774 B1 | 1/2013 |
| EP | 2538878 A1 | 1/2013 |
| EP | 2538881 A1 | 1/2013 |
| EP | 2538882 A1 | 1/2013 |
| EP | 2538883 A1 | 1/2013 |
| EP | 1512383 B1 | 2/2013 |
| EP | 1578474 B1 | 2/2013 |
| EP | 1648339 B1 | 2/2013 |
| EP | 1750622 B1 | 2/2013 |
| EP | 1994482 B1 | 2/2013 |
| EP | 2250975 B1 | 2/2013 |
| EP | 2257242 B1 | 2/2013 |
| EP | 2265225 B1 | 2/2013 |
| EP | 2558032 A1 | 2/2013 |
| EP | 1659992 B1 | 3/2013 |
| EP | 1701668 B1 | 3/2013 |
| EP | 2151216 B1 | 3/2013 |
| EP | 2340075 B1 | 3/2013 |
| EP | 2568924 A2 | 3/2013 |
| EP | 1781183 B1 | 4/2013 |
| EP | 1786367 B1 | 4/2013 |
| EP | 1850795 B1 | 4/2013 |
| EP | 1861041 B1 | 4/2013 |
| EP | 2319458 B1 | 4/2013 |
| EP | 2526898 B1 | 4/2013 |
| EP | 2537487 B1 | 4/2013 |
| EP | 2575681 A1 | 4/2013 |
| EP | 1901682 B1 | 5/2013 |
| EP | 1951166 B1 | 5/2013 |
| EP | 1994913 B1 | 5/2013 |
| EP | 2231070 B1 | 5/2013 |
| EP | 2401970 B1 | 5/2013 |
| EP | 2409651 B1 | 5/2013 |
| EP | 2594230 A1 | 5/2013 |
| EP | 1694246 B1 | 6/2013 |
| EP | 1948087 B1 | 6/2013 |
| EP | 2135559 B1 | 6/2013 |
| EP | 1115335 B1 | 7/2013 |
| EP | 1663339 B1 | 7/2013 |
| EP | 1864687 B1 | 7/2013 |
| EP | 1977719 B1 | 7/2013 |
| EP | 2111337 B1 | 7/2013 |
| EP | 2298237 B1 | 7/2013 |
| EP | 2309949 B1 | 7/2013 |
| EP | 2608741 A2 | 7/2013 |
| EP | 2611388 A2 | 7/2013 |
| EP | 2611389 A2 | 7/2013 |
| EP | 2618781 A2 | 7/2013 |
| EP | 1599151 B1 | 8/2013 |
| EP | 1761211 B1 | 8/2013 |
| EP | 2047871 B1 | 8/2013 |
| EP | 2142144 B1 | 8/2013 |
| EP | 2150206 B1 | 8/2013 |
| EP | 2319459 B1 | 8/2013 |
| EP | 2397108 B1 | 8/2013 |
| EP | 2623068 A1 | 8/2013 |
| EP | 1758523 B1 | 9/2013 |
| EP | 1545392 B1 | 10/2013 |
| EP | 1638627 B1 | 10/2013 |
| EP | 1779868 B1 | 10/2013 |
| EP | 2073756 B1 | 10/2013 |
| EP | 2111190 B1 | 10/2013 |
| EP | 2651336 A1 | 10/2013 |
| EP | 1848375 B1 | 11/2013 |
| EP | 1928356 B1 | 11/2013 |
| EP | 1933766 B1 | 11/2013 |
| EP | 2109417 B1 | 11/2013 |
| EP | 2194925 B1 | 11/2013 |
| EP | 2387977 B1 | 11/2013 |
| EP | 2476394 B1 | 11/2013 |
| EP | 2529701 B1 | 11/2013 |
| EP | 1945142 B1 | 12/2013 |
| EP | 2387972 B1 | 12/2013 |
| EP | 2477555 B1 | 12/2013 |
| EP | 2670349 A2 | 12/2013 |
| EP | 2670351 A1 | 12/2013 |
| EP | 2117476 B1 | 1/2014 |
| EP | 2526895 B1 | 1/2014 |
| EP | 2526899 B1 | 1/2014 |
| EP | 2529696 B1 | 1/2014 |
| EP | 2529697 B1 | 1/2014 |
| EP | 2529698 B1 | 1/2014 |
| EP | 2529699 B1 | 1/2014 |
| EP | 2679198 A1 | 1/2014 |
| EP | 2688516 A1 | 1/2014 |
| EP | 1395214 B1 | 2/2014 |
| EP | 1499266 B1 | 2/2014 |
| EP | 1838241 B1 | 2/2014 |

(56) References Cited

FOREIGN PATENT DOCUMENTS

| | | | |
|---|---|---|---|
| EP | 2520250 | B1 | 2/2014 |
| EP | 2526977 | B1 | 2/2014 |
| EP | 2693985 | A1 | 2/2014 |
| EP | 2698129 | A1 | 2/2014 |
| EP | 2699302 | A2 | 2/2014 |
| EP | 1629794 | B1 | 3/2014 |
| EP | 1919398 | B1 | 3/2014 |
| EP | 2099508 | B1 | 3/2014 |
| EP | 2399549 | B1 | 3/2014 |
| EP | 2422823 | B1 | 3/2014 |
| EP | 2706958 | A1 | 3/2014 |
| EP | 1804860 | B1 | 4/2014 |
| EP | 1926455 | B1 | 4/2014 |
| EP | 2081519 | B1 | 4/2014 |
| EP | 2117477 | B1 | 4/2014 |
| EP | 2405966 | B1 | 4/2014 |
| EP | 2420205 | B1 | 4/2014 |
| EP | 2593048 | B1 | 4/2014 |
| EP | 2713894 | A2 | 4/2014 |
| EP | 2713955 | A2 | 4/2014 |
| EP | 2723273 | A2 | 4/2014 |
| EP | 1499265 | B1 | 5/2014 |
| EP | 1594569 | B1 | 5/2014 |
| EP | 2029056 | B1 | 5/2014 |
| EP | 2257243 | B1 | 5/2014 |
| EP | 1791500 | B1 | 6/2014 |
| EP | 2073753 | B1 | 6/2014 |
| EP | 2306933 | B1 | 6/2014 |
| EP | 2331017 | B1 | 6/2014 |
| EP | 2337522 | B1 | 6/2014 |
| EP | 2389897 | B1 | 6/2014 |
| EP | 2606723 | B1 | 6/2014 |
| EP | 2739250 | A1 | 6/2014 |
| EP | 1487350 | B1 | 7/2014 |
| EP | 1977718 | B1 | 7/2014 |
| EP | 2117469 | B1 | 7/2014 |
| EP | 2124826 | B1 | 7/2014 |
| EP | 2258316 | B1 | 7/2014 |
| EP | 2747708 | A1 | 7/2014 |
| EP | 2750630 | A1 | 7/2014 |
| EP | 2750631 | A1 | 7/2014 |
| EP | 1667604 | B1 | 8/2014 |
| EP | 1786368 | B1 | 8/2014 |
| EP | 2211779 | B1 | 8/2014 |
| EP | 2217174 | B1 | 8/2014 |
| EP | 2293740 | B1 | 8/2014 |
| EP | 2367504 | B1 | 8/2014 |
| EP | 2453942 | B1 | 8/2014 |
| EP | 2475328 | B1 | 8/2014 |
| EP | 2545884 | B1 | 8/2014 |
| EP | 2571460 | B1 | 8/2014 |
| EP | 2763708 | A2 | 8/2014 |
| EP | 2765954 | A1 | 8/2014 |
| EP | 1935378 | B1 | 9/2014 |
| EP | 2246011 | B1 | 9/2014 |
| EP | 2422749 | B1 | 9/2014 |
| EP | 2531139 | B1 | 9/2014 |
| EP | 2609893 | B1 | 9/2014 |
| EP | 2777616 | A1 | 9/2014 |
| EP | 2779945 | A1 | 9/2014 |
| EP | 1853199 | B1 | 10/2014 |
| EP | 2133039 | B1 | 10/2014 |
| EP | 2549955 | B1 | 10/2014 |
| EP | 2549956 | B1 | 10/2014 |
| EP | 2651335 | B1 | 10/2014 |
| EP | 2785281 | A1 | 10/2014 |
| EP | 2793743 | A1 | 10/2014 |
| EP | 2793749 | | 10/2014 |
| EP | 2793752 | A1 | 10/2014 |
| EP | 2049721 | B1 | 11/2014 |
| EP | 2142143 | B1 | 11/2014 |
| EP | 2229921 | B1 | 11/2014 |
| EP | 2288403 | B1 | 11/2014 |
| EP | 2415421 | B1 | 11/2014 |
| EP | 1551274 | B1 | 12/2014 |
| EP | 1768735 | B1 | 12/2014 |
| EP | 1959865 | B1 | 12/2014 |
| EP | 2077718 | B1 | 12/2014 |
| EP | 2303185 | B1 | 12/2014 |
| EP | 2334857 | B1 | 12/2014 |
| EP | 2365840 | B1 | 12/2014 |
| EP | 2420207 | B1 | 12/2014 |
| EP | 2422750 | B1 | 12/2014 |
| EP | 2707073 | B1 | 12/2014 |
| EP | 1768630 | B1 | 1/2015 |
| EP | 2254515 | B1 | 1/2015 |
| EP | 2641569 | B1 | 1/2015 |
| EP | 2709559 | B1 | 1/2015 |
| EP | 2825203 | A1 | 1/2015 |
| EP | 1903990 | B1 | 2/2015 |
| EP | 2255753 | B1 | 2/2015 |
| EP | 2335649 | B1 | 2/2015 |
| EP | 2522308 | B1 | 2/2015 |
| EP | 2591754 | B1 | 2/2015 |
| EP | 2835112 | A1 | 2/2015 |
| EP | 2838473 | A1 | 2/2015 |
| EP | 1861045 | B1 | 3/2015 |
| EP | 2029057 | B1 | 3/2015 |
| EP | 2193761 | B1 | 3/2015 |
| EP | 2379010 | B1 | 3/2015 |
| EP | 2416737 | B1 | 3/2015 |
| EP | 2849678 | A1 | 3/2015 |
| EP | 1791495 | B1 | 4/2015 |
| EP | 2298252 | B1 | 4/2015 |
| EP | 2536359 | B1 | 4/2015 |
| EP | 2538879 | B1 | 4/2015 |
| EP | 2609894 | B1 | 4/2015 |
| EP | 2693984 | B1 | 4/2015 |
| EP | 2712633 | B1 | 4/2015 |
| EP | 2747707 | B1 | 4/2015 |
| EP | 2856973 | A1 | 4/2015 |
| EP | 2862546 | A1 | 4/2015 |
| EP | 2863842 | A1 | 4/2015 |
| EP | 1465555 | B1 | 5/2015 |
| EP | 1924224 | B1 | 5/2015 |
| EP | 1992369 | B1 | 5/2015 |
| EP | 2410947 | B1 | 5/2015 |
| EP | 2484311 | B1 | 5/2015 |
| EP | 2654616 | B1 | 5/2015 |
| EP | 2866741 | A1 | 5/2015 |
| EP | 1646332 | B1 | 6/2015 |
| EP | 2745805 | B1 | 6/2015 |
| EP | 2749254 | B1 | 6/2015 |
| EP | 2877123 | A2 | 6/2015 |
| EP | 2882374 | A1 | 6/2015 |
| EP | 2884906 | A1 | 6/2015 |
| EP | 1729685 | B1 | 7/2015 |
| EP | 1976439 | B1 | 7/2015 |
| EP | 2068767 | B1 | 7/2015 |
| EP | 2068769 | B1 | 7/2015 |
| EP | 2444031 | B1 | 7/2015 |
| EP | 2455041 | B1 | 7/2015 |
| EP | 2498719 | B1 | 7/2015 |
| EP | 2558030 | B1 | 7/2015 |
| EP | 2752209 | B1 | 7/2015 |
| EP | 2892467 | A1 | 7/2015 |
| EP | 1702247 | B1 | 8/2015 |
| EP | 1729688 | B1 | 8/2015 |
| EP | 1887979 | B1 | 8/2015 |
| EP | 2032079 | B1 | 8/2015 |
| EP | 2219558 | B1 | 8/2015 |
| EP | 2234657 | B1 | 8/2015 |
| EP | 2250976 | B1 | 8/2015 |
| EP | 2262447 | B1 | 8/2015 |
| EP | 2303384 | B1 | 8/2015 |
| EP | 2387365 | B1 | 8/2015 |
| EP | 2560579 | B1 | 8/2015 |
| EP | 2575621 | B1 | 8/2015 |
| EP | 2590595 | B1 | 8/2015 |
| EP | 2709560 | B1 | 8/2015 |
| EP | 2755603 | B1 | 8/2015 |
| EP | 2906147 | A1 | 8/2015 |
| EP | 1534185 | B1 | 9/2015 |
| EP | 1765225 | B1 | 9/2015 |

(56) References Cited

FOREIGN PATENT DOCUMENTS

| | | | |
|---|---|---|---|
| EP | 1778127 | B1 | 9/2015 |
| EP | 2094194 | B1 | 9/2015 |
| EP | 2201911 | B1 | 9/2015 |
| EP | 2306934 | B1 | 9/2015 |
| EP | 2397113 | B1 | 9/2015 |
| EP | 2453843 | B1 | 9/2015 |
| EP | 2459127 | B1 | 9/2015 |
| EP | 2675396 | B1 | 9/2015 |
| EP | 2675397 | B1 | 9/2015 |
| EP | 2736454 | B1 | 9/2015 |
| EP | 2754414 | A4 | 9/2015 |
| EP | 2790609 | B1 | 9/2015 |
| EP | 2805693 | B1 | 9/2015 |
| EP | 2911611 | A1 | 9/2015 |
| EP | 2916781 | A2 | 9/2015 |
| EP | 2919712 | | 9/2015 |
| EP | 1734903 | B1 | 10/2015 |
| EP | 1863546 | B1 | 10/2015 |
| EP | 1900343 | B1 | 10/2015 |
| EP | 2081515 | B1 | 10/2015 |
| EP | 2191792 | B1 | 10/2015 |
| EP | 2254513 | B1 | 10/2015 |
| EP | 2381896 | B1 | 10/2015 |
| EP | 2450008 | B1 | 10/2015 |
| EP | 2544626 | B1 | 10/2015 |
| EP | 2561830 | B1 | 10/2015 |
| EP | 2600798 | B1 | 10/2015 |
| EP | 2626039 | B1 | 10/2015 |
| EP | 2647354 | B1 | 10/2015 |
| EP | 2729093 | B1 | 10/2015 |
| EP | 2836165 | B1 | 10/2015 |
| EP | 1863545 | B1 | 11/2015 |
| EP | 2303395 | B1 | 11/2015 |
| EP | 2497446 | B1 | 11/2015 |
| EP | 2772228 | B1 | 11/2015 |
| EP | 1482869 | B1 | 12/2015 |
| EP | 1551473 | B1 | 12/2015 |
| EP | 1748745 | B1 | 12/2015 |
| EP | 1755459 | B1 | 12/2015 |
| EP | 1850796 | B1 | 12/2015 |
| EP | 1922030 | B1 | 12/2015 |
| EP | 1954212 | B1 | 12/2015 |
| EP | 2424472 | B1 | 12/2015 |
| EP | 2470120 | B1 | 12/2015 |
| EP | 2542179 | B1 | 12/2015 |
| EP | 2948100 | A1 | 12/2015 |
| EP | 2948103 | A2 | 12/2015 |
| EP | 2950752 | A2 | 12/2015 |
| EP | 2959866 | A1 | 12/2015 |
| EP | 1991168 | B1 | 1/2016 |
| EP | 2254512 | B1 | 1/2016 |
| EP | 2422748 | B1 | 1/2016 |
| EP | 2962664 | A1 | 1/2016 |
| EP | 2964153 | A1 | 1/2016 |
| EP | 2967700 | A1 | 1/2016 |
| EP | 2967807 | A2 | 1/2016 |
| EP | 2967834 | A1 | 1/2016 |
| EP | 2967856 | A1 | 1/2016 |
| EP | 2967858 | A2 | 1/2016 |
| EP | 2967860 | A1 | 1/2016 |
| EP | 2967866 | A2 | 1/2016 |
| EP | 2977026 | A1 | 1/2016 |
| EP | 1754684 | B1 | 2/2016 |
| EP | 1835948 | B1 | 2/2016 |
| EP | 2012712 | B1 | 2/2016 |
| EP | 2285318 | B1 | 2/2016 |
| EP | 2731550 | B1 | 2/2016 |
| EP | 2926766 | B1 | 2/2016 |
| EP | 2982337 | A1 | 2/2016 |
| EP | 1585463 | B1 | 3/2016 |
| EP | 1638621 | B1 | 3/2016 |
| EP | 1804726 | B1 | 3/2016 |
| EP | 1865886 | B1 | 3/2016 |
| EP | 1887982 | B1 | 3/2016 |
| EP | 2150205 | B1 | 3/2016 |
| EP | 2278944 | B1 | 3/2016 |
| EP | 2291126 | B1 | 3/2016 |
| EP | 2517674 | B1 | 3/2016 |
| EP | 2520253 | B1 | 3/2016 |
| EP | 2526897 | B1 | 3/2016 |
| EP | 2621409 | A4 | 3/2016 |
| EP | 2670353 | B1 | 3/2016 |
| EP | 2674130 | B1 | 3/2016 |
| EP | 2780042 | B1 | 3/2016 |
| EP | 2991584 | A1 | 3/2016 |
| EP | 2991587 | A2 | 3/2016 |
| EP | 2991588 | A1 | 3/2016 |
| EP | 2994072 | A1 | 3/2016 |
| EP | 2994075 | A1 | 3/2016 |
| EP | 2996632 | A1 | 3/2016 |
| EP | 2996633 | A1 | 3/2016 |
| EP | 2996641 | A1 | 3/2016 |
| EP | 2999435 | A1 | 3/2016 |
| EP | 1420730 | B1 | 4/2016 |
| EP | 1545371 | B1 | 4/2016 |
| EP | 1592367 | B1 | 4/2016 |
| EP | 1708649 | B1 | 4/2016 |
| EP | 1871300 | B1 | 4/2016 |
| EP | 2168536 | B1 | 4/2016 |
| EP | 2399550 | B1 | 4/2016 |
| EP | 2433591 | B1 | 4/2016 |
| EP | 2478871 | B1 | 4/2016 |
| EP | 2536355 | B1 | 4/2016 |
| EP | 2572676 | B1 | 4/2016 |
| EP | 2606852 | B1 | 4/2016 |
| EP | 2621408 | B1 | 4/2016 |
| EP | 2626041 | B1 | 4/2016 |
| EP | 2633821 | B1 | 4/2016 |
| EP | 2670354 | B1 | 4/2016 |
| EP | 2702965 | B1 | 4/2016 |
| EP | 2704669 | B1 | 4/2016 |
| EP | 2815725 | B1 | 4/2016 |
| EP | 3007651 | A1 | 4/2016 |
| EP | 3010564 | A1 | 4/2016 |
| EP | 2194933 | B1 | 5/2016 |
| EP | 2237746 | B1 | 5/2016 |
| EP | 2378947 | B1 | 5/2016 |
| EP | 2542184 | B1 | 5/2016 |
| EP | 2572684 | B1 | 5/2016 |
| EP | 2582326 | B1 | 5/2016 |
| EP | 2618784 | B1 | 5/2016 |
| EP | 2654623 | B1 | 5/2016 |
| EP | 2656816 | B1 | 5/2016 |
| EP | 2680791 | B1 | 5/2016 |
| EP | 2693986 | B1 | 5/2016 |
| EP | 2806805 | B1 | 5/2016 |
| EP | 2866739 | B1 | 5/2016 |
| EP | 2889020 | B1 | 5/2016 |
| EP | 2926767 | B1 | 5/2016 |
| EP | 2949292 | B1 | 5/2016 |
| EP | 3019092 | A1 | 5/2016 |
| EP | 1734902 | B1 | 6/2016 |
| EP | 1906884 | B1 | 6/2016 |
| EP | 2111800 | B1 | 6/2016 |
| EP | 2160156 | B1 | 6/2016 |
| EP | 2190379 | B1 | 6/2016 |
| EP | 2193762 | B1 | 6/2016 |
| EP | 2416739 | B1 | 6/2016 |
| EP | 2453969 | B1 | 6/2016 |
| EP | 2515800 | B1 | 6/2016 |
| EP | 2558031 | B1 | 6/2016 |
| EP | 2563236 | B1 | 6/2016 |
| EP | 2572675 | B1 | 6/2016 |
| EP | 2626040 | B1 | 6/2016 |
| EP | 2704668 | B1 | 6/2016 |
| EP | 2777611 | B1 | 6/2016 |
| EP | 2815724 | B1 | 6/2016 |
| EP | 2854710 | B1 | 6/2016 |
| EP | 2901966 | B1 | 6/2016 |
| EP | 3024527 | A2 | 6/2016 |
| EP | 1605866 | B1 | 7/2016 |
| EP | 1933756 | B1 | 7/2016 |
| EP | 2393452 | B1 | 7/2016 |
| EP | 2410948 | B1 | 7/2016 |

(56) References Cited

FOREIGN PATENT DOCUMENTS

| | | | |
|---|---|---|---|
| EP | 2412397 | B1 | 7/2016 |
| EP | 2724690 | B1 | 7/2016 |
| EP | 2815723 | B1 | 7/2016 |
| EP | 2870945 | B1 | 7/2016 |
| EP | 3038567 | A1 | 7/2016 |
| EP | 3040054 | A1 | 7/2016 |
| EP | 3042635 | A1 | 7/2016 |
| EP | 3043745 | A1 | 7/2016 |
| EP | 3043747 | A1 | 7/2016 |
| EP | 3043755 | A1 | 7/2016 |
| EP | 1401358 | B1 | 8/2016 |
| EP | 1915105 | B1 | 8/2016 |
| EP | 1937186 | B1 | 8/2016 |
| EP | 2292186 | B1 | 8/2016 |
| EP | 2379012 | B1 | 8/2016 |
| EP | 2385809 | B1 | 8/2016 |
| EP | 2536345 | B1 | 8/2016 |
| EP | 2537490 | B1 | 8/2016 |
| EP | 2549954 | B1 | 8/2016 |
| EP | 2618779 | B1 | 8/2016 |
| EP | 2670352 | B1 | 8/2016 |
| EP | 2829235 | B1 | 8/2016 |
| EP | 2853238 | B1 | 8/2016 |
| EP | 2866738 | B1 | 8/2016 |
| EP | 2906150 | B1 | 8/2016 |
| EP | 3052053 | A1 | 8/2016 |
| EP | 3052611 | A1 | 8/2016 |
| EP | 3060171 | A1 | 8/2016 |
| EP | 3060174 | A1 | 8/2016 |
| EP | 3061421 | A1 | 8/2016 |
| EP | 3061422 | A1 | 8/2016 |
| EP | 1156755 | B1 | 9/2016 |
| EP | 1492478 | B1 | 9/2016 |
| EP | 1912697 | B1 | 9/2016 |
| EP | 2393449 | B1 | 9/2016 |
| EP | 2670356 | B1 | 9/2016 |
| EP | 2793969 | B1 | 9/2016 |
| EP | 2809271 | B1 | 9/2016 |
| EP | 2896425 | B1 | 9/2016 |
| EP | 3068345 | A1 | 9/2016 |
| EP | 3068346 | A1 | 9/2016 |
| EP | 3071148 | A1 | 9/2016 |
| EP | 3071149 | A1 | 9/2016 |
| EP | 2023858 | B1 | 10/2016 |
| EP | 2112912 | B1 | 10/2016 |
| EP | 2640319 | B1 | 10/2016 |
| EP | 2663257 | B1 | 10/2016 |
| EP | 2727612 | B1 | 10/2016 |
| EP | 2760384 | B1 | 10/2016 |
| EP | 2806829 | B1 | 10/2016 |
| EP | 2858599 | B1 | 10/2016 |
| EP | 2918250 | B1 | 10/2016 |
| EP | 2922592 | A4 | 10/2016 |
| EP | 2934387 | B1 | 10/2016 |
| EP | 3076901 | A1 | 10/2016 |
| EP | 3079633 | A1 | 10/2016 |
| EP | 1539047 | B1 | 11/2016 |
| EP | 2282700 | B1 | 11/2016 |
| EP | 2400926 | B1 | 11/2016 |
| EP | 2467104 | B1 | 11/2016 |
| EP | 2525743 | B1 | 11/2016 |
| EP | 2549953 | B1 | 11/2016 |
| EP | 2575696 | B1 | 11/2016 |
| EP | 2598045 | B1 | 11/2016 |
| EP | 2670355 | B1 | 11/2016 |
| EP | 2676640 | B1 | 11/2016 |
| EP | 2680792 | B1 | 11/2016 |
| EP | 2707053 | B1 | 11/2016 |
| EP | 2717803 | B1 | 11/2016 |
| EP | 2773297 | B1 | 11/2016 |
| EP | 2801387 | B1 | 11/2016 |
| EP | 2844192 | B1 | 11/2016 |
| EP | 2849679 | B1 | 11/2016 |
| EP | 2877122 | B1 | 11/2016 |
| EP | 2908778 | B1 | 11/2016 |
| EP | 2922500 | B1 | 11/2016 |
| EP | 2922501 | B1 | 11/2016 |
| EP | 2967854 | B1 | 11/2016 |
| EP | 3020365 | B1 | 11/2016 |
| EP | 3090703 | A1 | 11/2016 |
| EP | 3096713 | A1 | 11/2016 |
| EP | 1645244 | B1 | 12/2016 |
| EP | 1667614 | B1 | 12/2016 |
| EP | 1684656 | B1 | 12/2016 |
| EP | 1684670 | B1 | 12/2016 |
| EP | 1750592 | B1 | 12/2016 |
| EP | 1883375 | B1 | 12/2016 |
| EP | 2293739 | B1 | 12/2016 |
| EP | 2339988 | B1 | 12/2016 |
| EP | 2512375 | B1 | 12/2016 |
| EP | 2754417 | B1 | 12/2016 |
| EP | 2754418 | B1 | 12/2016 |
| EP | 2755562 | B1 | 12/2016 |
| EP | 2889019 | B1 | 12/2016 |
| EP | 3010442 | B1 | 12/2016 |
| EP | 3099271 | A1 | 12/2016 |
| EP | 3102150 | | 12/2016 |
| EP | 3107495 | A1 | 12/2016 |
| EP | 3107498 | A2 | 12/2016 |
| EP | 3107500 | A1 | 12/2016 |
| EP | 1893127 | B1 | 1/2017 |
| EP | 1951352 | B1 | 1/2017 |
| EP | 2109419 | B1 | 1/2017 |
| EP | 2185107 | B1 | 1/2017 |
| EP | 2266503 | B1 | 1/2017 |
| EP | 2340055 | B1 | 1/2017 |
| EP | 2395941 | B1 | 1/2017 |
| EP | 2400923 | B1 | 1/2017 |
| EP | 2629699 | B1 | 1/2017 |
| EP | 2645963 | B1 | 1/2017 |
| EP | 2654622 | B1 | 1/2017 |
| EP | 2706952 | B1 | 1/2017 |
| EP | 2760347 | B1 | 1/2017 |
| EP | 2771064 | B1 | 1/2017 |
| EP | 2780077 | B1 | 1/2017 |
| EP | 2809272 | B1 | 1/2017 |
| EP | 2934385 | B1 | 1/2017 |
| EP | 2986255 | B1 | 1/2017 |
| EP | 3119351 | A1 | 1/2017 |
| EP | 1507493 | B1 | 2/2017 |
| EP | 2563238 | B1 | 2/2017 |
| EP | 2752170 | B1 | 2/2017 |
| EP | 2760371 | B1 | 2/2017 |
| EP | 2793709 | B1 | 2/2017 |
| EP | 2793748 | B1 | 2/2017 |
| EP | 2793763 | B1 | 2/2017 |
| EP | 2832317 | B1 | 2/2017 |
| EP | 2921135 | B1 | 2/2017 |
| EP | 2967931 | B1 | 2/2017 |
| EP | 2974693 | B1 | 2/2017 |
| EP | 3025680 | B1 | 2/2017 |
| EP | 3025681 | B1 | 2/2017 |
| EP | 3125826 | A1 | 2/2017 |
| EP | 3125827 | A2 | 2/2017 |
| EP | 3128927 | A1 | 2/2017 |
| EP | 3131502 | A1 | 2/2017 |
| EP | 1845895 | B1 | 3/2017 |
| EP | 2190385 | B1 | 3/2017 |
| EP | 2266504 | B1 | 3/2017 |
| EP | 2341871 | B1 | 3/2017 |
| EP | 2379011 | B1 | 3/2017 |
| EP | 2379013 | B1 | 3/2017 |
| EP | 2640316 | B1 | 3/2017 |
| EP | 2731552 | B1 | 3/2017 |
| EP | 2756109 | B1 | 3/2017 |
| EP | 2773298 | B1 | 3/2017 |
| EP | 2832316 | B1 | 3/2017 |
| EP | 2854718 | B1 | 3/2017 |
| EP | 2881083 | B1 | 3/2017 |
| EP | 2934390 | B1 | 3/2017 |
| EP | 2934391 | B1 | 3/2017 |
| EP | 3010564 | A4 | 3/2017 |
| EP | 3145451 | A2 | 3/2017 |
| EP | 3146938 | A1 | 3/2017 |

(56) References Cited

FOREIGN PATENT DOCUMENTS

| | | |
|---|---|---|
| EP | 2014239 B1 | 4/2017 |
| EP | 2111189 B1 | 4/2017 |
| EP | 2393451 B1 | 4/2017 |
| EP | 2617388 B1 | 4/2017 |
| EP | 2629700 B1 | 4/2017 |
| EP | 2832318 B1 | 4/2017 |
| EP | 2893904 B1 | 4/2017 |
| EP | 2982340 B1 | 4/2017 |
| EP | 3000436 B1 | 4/2017 |
| EP | 3001979 B1 | 4/2017 |
| EP | 3043749 B1 | 4/2017 |
| EP | 3045147 B1 | 4/2017 |
| EP | 3054893 B1 | 4/2017 |
| EP | 3154474 A1 | 4/2017 |
| EP | 3156007 A1 | 4/2017 |
| EP | 3157469 A1 | 4/2017 |
| EP | 3158975 | 4/2017 |
| EP | 1855614 B1 | 5/2017 |
| EP | 2001402 B1 | 5/2017 |
| EP | 2032080 B1 | 5/2017 |
| EP | 2262451 B1 | 5/2017 |
| EP | 2470119 B1 | 5/2017 |
| EP | 2478869 B1 | 5/2017 |
| EP | 2538880 B1 | 5/2017 |
| EP | 2545850 B1 | 5/2017 |
| EP | 2600799 B1 | 5/2017 |
| EP | 2717926 B1 | 5/2017 |
| EP | 2726024 B1 | 5/2017 |
| EP | 2805678 B1 | 5/2017 |
| EP | 2809270 B1 | 5/2017 |
| EP | 2918245 B1 | 5/2017 |
| EP | 2953579 B1 | 5/2017 |
| EP | 2976043 B1 | 5/2017 |
| EP | 2979666 B1 | 5/2017 |
| EP | 3011931 B1 | 5/2017 |
| EP | 3025682 B1 | 5/2017 |
| EP | 3033135 B1 | 5/2017 |
| EP | 3160396 A1 | 5/2017 |
| EP | 3167847 A1 | 5/2017 |
| EP | 3169245 A1 | 5/2017 |
| EP | 3169276 A1 | 5/2017 |
| EP | 2351541 B1 | 6/2017 |
| EP | 2384165 B1 | 6/2017 |
| EP | 2400924 B1 | 6/2017 |
| EP | 2419041 B1 | 6/2017 |
| EP | 2419050 B1 | 6/2017 |
| EP | 2489331 B1 | 6/2017 |
| EP | 2493417 B1 | 6/2017 |
| EP | 2560585 B1 | 6/2017 |
| EP | 2611387 B1 | 6/2017 |
| EP | 2645967 B1 | 6/2017 |
| EP | 2677965 B1 | 6/2017 |
| EP | 2760349 B1 | 6/2017 |
| EP | 2826443 B1 | 6/2017 |
| EP | 2906148 B1 | 6/2017 |
| EP | 2929860 B1 | 6/2017 |
| EP | 2934669 B1 | 6/2017 |
| EP | 2967852 B1 | 6/2017 |
| EP | 3076901 A4 | 6/2017 |
| EP | 3174502 A1 | 6/2017 |
| EP | 3175823 | 6/2017 |
| EP | 3178443 A1 | 6/2017 |
| EP | 3178445 A1 | 6/2017 |
| EP | 3184081 A1 | 6/2017 |
| EP | 1624810 B1 | 7/2017 |
| EP | 2026703 B1 | 7/2017 |
| EP | 2293718 B1 | 7/2017 |
| EP | 2339989 B1 | 7/2017 |
| EP | 2344076 B1 | 7/2017 |
| EP | 2486893 B1 | 7/2017 |
| EP | 2536356 B1 | 7/2017 |
| EP | 2548534 B1 | 7/2017 |
| EP | 2608742 B1 | 7/2017 |
| EP | 2673038 B1 | 7/2017 |
| EP | 2676638 B1 | 7/2017 |
| EP | 2774630 B1 | 7/2017 |
| EP | 2825107 B1 | 7/2017 |
| EP | 2841020 B1 | 7/2017 |
| EP | 2934386 B1 | 7/2017 |
| EP | 2943151 B1 | 7/2017 |
| EP | 3058894 B1 | 7/2017 |
| EP | 3071151 B1 | 7/2017 |
| EP | 3191025 A1 | 7/2017 |
| EP | 3193740 A2 | 7/2017 |
| EP | 3193782 A1 | 7/2017 |
| EP | 1530441 B1 | 8/2017 |
| EP | 1722716 B1 | 8/2017 |
| EP | 1971289 B1 | 8/2017 |
| EP | 2323591 B1 | 8/2017 |
| EP | 2344070 B1 | 8/2017 |
| EP | 2393442 A4 | 8/2017 |
| EP | 2413842 B1 | 8/2017 |
| EP | 2427143 B1 | 8/2017 |
| EP | 2459077 B1 | 8/2017 |
| EP | 2480167 B1 | 8/2017 |
| EP | 2482749 B1 | 8/2017 |
| EP | 2496181 B1 | 8/2017 |
| EP | 2568925 B1 | 8/2017 |
| EP | 2617389 B1 | 8/2017 |
| EP | 2713954 B1 | 8/2017 |
| EP | 2755602 B1 | 8/2017 |
| EP | 2800602 B1 | 8/2017 |
| EP | 2809263 B1 | 8/2017 |
| EP | 2830536 B1 | 8/2017 |
| EP | 2841009 B1 | 8/2017 |
| EP | 2844190 B1 | 8/2017 |
| EP | 2849681 B1 | 8/2017 |
| EP | 2858600 B1 | 8/2017 |
| EP | 2897556 B1 | 8/2017 |
| EP | 2934388 B1 | 8/2017 |
| EP | 2979667 B1 | 8/2017 |
| EP | 3197397 A1 | 8/2017 |
| EP | 3202371 A1 | 8/2017 |
| EP | 3206629 A1 | 8/2017 |
| EP | 3206631 A2 | 8/2017 |
| EP | 1799093 B1 | 9/2017 |
| EP | 2010103 B1 | 9/2017 |
| EP | 2114304 B1 | 9/2017 |
| EP | 2344090 B1 | 9/2017 |
| EP | 2398421 B1 | 9/2017 |
| EP | 2437687 B1 | 9/2017 |
| EP | 2453970 B1 | 9/2017 |
| EP | 2509538 B1 | 9/2017 |
| EP | 2713956 B1 | 9/2017 |
| EP | 2772227 B1 | 9/2017 |
| EP | 2787924 B1 | 9/2017 |
| EP | 2803335 B1 | 9/2017 |
| EP | 2811939 B1 | 9/2017 |
| EP | 2830537 B1 | 9/2017 |
| EP | 2865355 B1 | 9/2017 |
| EP | 2872047 B1 | 9/2017 |
| EP | 2934389 B1 | 9/2017 |
| EP | 3213715 A1 | 9/2017 |
| EP | 3213716 A1 | 9/2017 |
| EP | 3215061 A1 | 9/2017 |
| EP | 3220856 A2 | 9/2017 |
| EP | 3220857 A1 | 9/2017 |
| EP | 1945141 B1 | 10/2017 |
| EP | 2317956 B1 | 10/2017 |
| EP | 2613737 B1 | 10/2017 |
| EP | 2620125 B1 | 10/2017 |
| EP | 2720642 B1 | 10/2017 |
| EP | 2741682 B1 | 10/2017 |
| EP | 2872077 B1 | 10/2017 |
| EP | 3021925 B1 | 10/2017 |
| EP | 3231395 A1 | 10/2017 |
| EP | 3232989 A1 | 10/2017 |
| EP | 1651148 B1 | 11/2017 |
| EP | 1913901 B1 | 11/2017 |
| EP | 2222248 B1 | 11/2017 |
| EP | 2296581 B1 | 11/2017 |
| EP | 2326264 B1 | 11/2017 |
| EP | 2427142 B1 | 11/2017 |
| EP | 2456483 B1 | 11/2017 |

(56) References Cited

FOREIGN PATENT DOCUMENTS

| | | | |
|---|---|---|---|
| EP | 2493423 B1 | 11/2017 |
| EP | 2611391 B1 | 11/2017 |
| EP | 2618780 B1 | 11/2017 |
| EP | 2658480 B1 | 11/2017 |
| EP | 2710978 B1 | 11/2017 |
| EP | 2832315 B1 | 11/2017 |
| EP | 2954875 B1 | 11/2017 |
| EP | 2967861 B1 | 11/2017 |
| EP | 2982338 B1 | 11/2017 |
| EP | 3027144 B1 | 11/2017 |
| EP | 3043746 B1 | 11/2017 |
| EP | 3049026 B1 | 11/2017 |
| EP | 3068311 B1 | 11/2017 |
| EP | 3110368 B1 | 11/2017 |
| EP | 3110369 B1 | 11/2017 |
| EP | 3132773 B1 | 11/2017 |
| EP | 3238662 A1 | 11/2017 |
| EP | 3245980 A1 | 11/2017 |
| EP | 3247312 A1 | 11/2017 |
| EP | 1667603 B1 | 12/2017 |
| EP | 1874954 B1 | 12/2017 |
| EP | 2427145 B1 | 12/2017 |
| EP | 2542185 B1 | 12/2017 |
| EP | 2670351 A4 | 12/2017 |
| EP | 2723274 B1 | 12/2017 |
| EP | 2736455 B1 | 12/2017 |
| EP | 2736457 B1 | 12/2017 |
| EP | 2830534 B1 | 12/2017 |
| EP | 2830535 B1 | 12/2017 |
| EP | 2911592 B1 | 12/2017 |
| EP | 2916772 B1 | 12/2017 |
| EP | 2967922 B1 | 12/2017 |
| EP | 3009105 B1 | 12/2017 |
| EP | 3088037 B1 | 12/2017 |
| EP | 3115023 B1 | 12/2017 |
| EP | 3251633 A1 | 12/2017 |
| EP | 3256074 A1 | 12/2017 |
| EP | 3256076 A1 | 12/2017 |
| EP | 3256178 A1 | 12/2017 |
| EP | 1492458 B1 | 1/2018 |
| EP | 1768604 B1 | 1/2018 |
| EP | 1951154 B1 | 1/2018 |
| EP | 2091465 B1 | 1/2018 |
| EP | 2345380 B1 | 1/2018 |
| EP | 2456363 B1 | 1/2018 |
| EP | 2531143 B1 | 1/2018 |
| EP | 2621407 B1 | 1/2018 |
| EP | 2694123 B1 | 1/2018 |
| EP | 2775962 B1 | 1/2018 |
| EP | 2874568 B1 | 1/2018 |
| EP | 2967863 B1 | 1/2018 |
| EP | 2967869 B1 | 1/2018 |
| EP | 3033047 B1 | 1/2018 |
| EP | 3037065 B1 | 1/2018 |
| EP | 3049025 B1 | 1/2018 |
| EP | 3052052 B1 | 1/2018 |
| EP | 3078350 B1 | 1/2018 |
| EP | 3266417 A1 | 1/2018 |
| EP | 3267946 A1 | 1/2018 |
| EP | 3269331 A1 | 1/2018 |
| EP | 3273911 A1 | 1/2018 |
| EP | 3275404 A1 | 1/2018 |
| EP | 2197512 B1 | 2/2018 |
| EP | 2248486 B1 | 2/2018 |
| EP | 2344066 B1 | 2/2018 |
| EP | 2381854 B1 | 2/2018 |
| EP | 2667823 B1 | 2/2018 |
| EP | 2699169 B1 | 2/2018 |
| EP | 2714177 B1 | 2/2018 |
| EP | 2736544 B1 | 2/2018 |
| EP | 2846736 B1 | 2/2018 |
| EP | 2886082 B1 | 2/2018 |
| EP | 2886084 B1 | 2/2018 |
| EP | 2931178 B1 | 2/2018 |
| EP | 2934392 B1 | 2/2018 |
| EP | 3150173 B1 | 2/2018 |
| EP | 3277221 A1 | 2/2018 |
| EP | 3277222 A1 | 2/2018 |
| EP | 3280358 A1 | 2/2018 |
| EP | 3281608 A1 | 2/2018 |
| EP | 3283011 A1 | 2/2018 |
| EP | 3287099 A1 | 2/2018 |
| EP | 1959864 B1 | 3/2018 |
| EP | 2513200 B1 | 3/2018 |
| EP | 2608815 B1 | 3/2018 |
| EP | 2858711 B1 | 3/2018 |
| EP | 2938292 B1 | 3/2018 |
| EP | 2943132 B1 | 3/2018 |
| EP | 2983620 B1 | 3/2018 |
| EP | 3003219 B1 | 3/2018 |
| EP | 3005979 B1 | 3/2018 |
| EP | 3037064 B1 | 3/2018 |
| EP | 3046511 B1 | 3/2018 |
| EP | 3142603 B1 | 3/2018 |
| EP | 3288479 A1 | 3/2018 |
| EP | 3288491 A1 | 3/2018 |
| EP | 3288494 A1 | 3/2018 |
| EP | 3288497 A2 | 3/2018 |
| EP | 3288498 A1 | 3/2018 |
| EP | 3288499 A1 | 3/2018 |
| EP | 3290004 A1 | 3/2018 |
| EP | 3290007 A1 | 3/2018 |
| EP | 3294214 A1 | 3/2018 |
| EP | 3294215 A1 | 3/2018 |
| EP | 3294218 A1 | 3/2018 |
| EP | 3296979 A1 | 3/2018 |
| EP | 3298970 A1 | 3/2018 |
| EP | 3298987 A1 | 3/2018 |
| EP | 3298988 A1 | 3/2018 |
| EP | 2209440 B1 | 4/2018 |
| EP | 2536357 B1 | 4/2018 |
| EP | 2605725 B1 | 4/2018 |
| EP | 2608743 B1 | 4/2018 |
| EP | 2709561 B1 | 4/2018 |
| EP | 2787925 B1 | 4/2018 |
| EP | 2789314 B1 | 4/2018 |
| EP | 2900150 B1 | 4/2018 |
| EP | 2908779 B1 | 4/2018 |
| EP | 2922502 B1 | 4/2018 |
| EP | 2964441 B1 | 4/2018 |
| EP | 2967868 B1 | 4/2018 |
| EP | 2979665 B1 | 4/2018 |
| EP | 2994073 B1 | 4/2018 |
| EP | 3095394 B1 | 4/2018 |
| EP | 3128927 A4 | 4/2018 |
| EP | 3134033 B1 | 4/2018 |
| EP | 3137146 A4 | 4/2018 |
| EP | 3280482 A4 | 4/2018 |
| EP | 3302362 A1 | 4/2018 |
| EP | 3302367 A1 | 4/2018 |
| EP | 3307208 A1 | 4/2018 |
| EP | 3308745 A1 | 4/2018 |
| EP | 3310301 A1 | 4/2018 |
| EP | 3311775 | 4/2018 |
| EP | 1945112 B1 | 5/2018 |
| EP | 2007313 B1 | 5/2018 |
| EP | 2316381 B2 | 5/2018 |
| EP | 2377469 B1 | 5/2018 |
| EP | 2531115 B1 | 5/2018 |
| EP | 2561831 B1 | 5/2018 |
| EP | 2605724 B1 | 5/2018 |
| EP | 2723277 B1 | 5/2018 |
| EP | 2741711 B1 | 5/2018 |
| EP | 2755573 B1 | 5/2018 |
| EP | 2768429 B1 | 5/2018 |
| EP | 2819618 B1 | 5/2018 |
| EP | 2833836 B1 | 5/2018 |
| EP | 2886083 B1 | 5/2018 |
| EP | 2926840 B1 | 5/2018 |
| EP | 2943157 B1 | 5/2018 |
| EP | 2948099 B1 | 5/2018 |
| EP | 3000437 B1 | 5/2018 |
| EP | 3145448 B1 | 5/2018 |
| EP | 3154475 B1 | 5/2018 |

(56) References Cited

FOREIGN PATENT DOCUMENTS

| | | |
|---|---|---|
| EP | 3316819 A1 | 5/2018 |
| EP | 3316821 A1 | 5/2018 |
| EP | 3322381 A1 | 5/2018 |
| EP | 3322383 A1 | 5/2018 |
| EP | 3323353 A1 | 5/2018 |
| EP | 3323439 A1 | 5/2018 |
| EP | 3324892 A1 | 5/2018 |
| EP | 3326584 A1 | 5/2018 |
| EP | 2150312 B1 | 6/2018 |
| EP | 2379322 B1 | 6/2018 |
| EP | 2400925 B1 | 6/2018 |
| EP | 2552355 B1 | 6/2018 |
| EP | 2560589 B1 | 6/2018 |
| EP | 2563277 B1 | 6/2018 |
| EP | 2661305 B1 | 6/2018 |
| EP | 2736456 B1 | 6/2018 |
| EP | 2782523 B1 | 6/2018 |
| EP | 3056170 B1 | 6/2018 |
| EP | 3062745 B1 | 6/2018 |
| EP | 3130320 B1 | 6/2018 |
| EP | 3187150 B1 | 6/2018 |
| EP | 3334378 A1 | 6/2018 |
| EP | 3334380 A1 | 6/2018 |
| EP | 3334381 A1 | 6/2018 |
| EP | 3337412 A1 | 6/2018 |
| EP | 3337424 A1 | 6/2018 |
| EP | 2478872 B1 | 7/2018 |
| EP | 2563278 B1 | 7/2018 |
| EP | 2616004 B1 | 7/2018 |
| EP | 2779943 B1 | 7/2018 |
| EP | 2802290 B1 | 7/2018 |
| EP | 2816980 B1 | 7/2018 |
| EP | 2938293 B1 | 7/2018 |
| EP | 3107496 B1 | 7/2018 |
| EP | 3178450 B1 | 7/2018 |
| EP | 3212097 B1 | 7/2018 |
| EP | 3340923 A1 | 7/2018 |
| EP | 3340932 A1 | 7/2018 |
| EP | 3340934 A1 | 7/2018 |
| EP | 3340936 A1 | 7/2018 |
| EP | 3340945 A1 | 7/2018 |
| EP | 3342355 A1 | 7/2018 |
| EP | 3342377 A1 | 7/2018 |
| EP | 3344158 | 7/2018 |
| EP | 3346952 A1 | 7/2018 |
| EP | 3347182 A1 | 7/2018 |
| EP | 3348235 A1 | 7/2018 |
| EP | 2536354 B1 | 8/2018 |
| EP | 2616006 B1 | 8/2018 |
| EP | 2797556 B1 | 8/2018 |
| EP | 2822473 B1 | 8/2018 |
| EP | 2854711 B1 | 8/2018 |
| EP | 2866847 B1 | 8/2018 |
| EP | 2918246 B1 | 8/2018 |
| EP | 2967845 B1 | 8/2018 |
| EP | 2999436 B1 | 8/2018 |
| EP | 3013281 B1 | 8/2018 |
| EP | 3060170 B1 | 8/2018 |
| EP | 3104811 B1 | 8/2018 |
| EP | 3143944 B1 | 8/2018 |
| EP | 3157467 B1 | 8/2018 |
| EP | 3193791 B1 | 8/2018 |
| EP | 3241526 B1 | 8/2018 |
| EP | 3355800 A1 | 8/2018 |
| EP | 3360513 A1 | 8/2018 |
| EP | 3360514 A1 | 8/2018 |
| EP | 3361988 A1 | 8/2018 |
| EP | 3361991 | 8/2018 |
| EP | 2114305 B1 | 9/2018 |
| EP | 2155115 B1 | 9/2018 |
| EP | 2601910 B1 | 9/2018 |
| EP | 2617390 B1 | 9/2018 |
| EP | 2734157 B1 | 9/2018 |
| EP | 2968674 B1 | 9/2018 |
| EP | 2999415 B1 | 9/2018 |
| EP | 3106130 B1 | 9/2018 |
| EP | 3151763 B1 | 9/2018 |
| EP | 3213717 B1 | 9/2018 |
| EP | 3245985 B1 | 9/2018 |
| EP | 3367979 A1 | 9/2018 |
| EP | 3370649 A1 | 9/2018 |
| EP | 3370650 A1 | 9/2018 |
| EP | 3377000 A1 | 9/2018 |
| EP | 1827256 B1 | 10/2018 |
| EP | 1850790 B1 | 10/2018 |
| EP | 2063823 B1 | 10/2018 |
| EP | 2124825 B1 | 10/2018 |
| EP | 2249746 B1 | 10/2018 |
| EP | 2254514 B1 | 10/2018 |
| EP | 2285309 B1 | 10/2018 |
| EP | 2455042 B1 | 10/2018 |
| EP | 2571561 B1 | 10/2018 |
| EP | 2616008 B1 | 10/2018 |
| EP | 2647393 B1 | 10/2018 |
| EP | 2739214 B1 | 10/2018 |
| EP | 2739247 B1 | 10/2018 |
| EP | 2776114 B1 | 10/2018 |
| EP | 2836171 B1 | 10/2018 |
| EP | 2842581 B1 | 10/2018 |
| EP | 2870946 B1 | 10/2018 |
| EP | 2923665 B1 | 10/2018 |
| EP | 2964277 B1 | 10/2018 |
| EP | 3001978 B1 | 10/2018 |
| EP | 3010562 B1 | 10/2018 |
| EP | 3072475 B1 | 10/2018 |
| EP | 3081161 B1 | 10/2018 |
| EP | 3081195 B1 | 10/2018 |
| EP | 3099345 B1 | 10/2018 |
| EP | 3120809 B1 | 10/2018 |
| EP | 3238663 B1 | 10/2018 |
| EP | 3275404 A4 | 10/2018 |
| EP | 3384879 A1 | 10/2018 |
| EP | 3388027 A1 | 10/2018 |
| EP | 3389557 A1 | 10/2018 |
| EP | 3390706 A1 | 10/2018 |
| EP | 1708650 B1 | 11/2018 |
| EP | 1945143 B1 | 11/2018 |
| EP | 2205183 B1 | 11/2018 |
| EP | 2663258 B1 | 11/2018 |
| EP | 2790615 B1 | 11/2018 |
| EP | 2854709 B1 | 11/2018 |
| EP | 2898859 B1 | 11/2018 |
| EP | 2921139 B1 | 11/2018 |
| EP | 2928538 B1 | 11/2018 |
| EP | 3075354 B1 | 11/2018 |
| EP | 3082949 B1 | 11/2018 |
| EP | 3145452 B1 | 11/2018 |
| EP | 3216424 B1 | 11/2018 |
| EP | 3260084 B1 | 11/2018 |
| EP | 3397206 A1 | 11/2018 |
| EP | 3398562 A1 | 11/2018 |
| EP | 3400908 A1 | 11/2018 |
| EP | 3403616 A1 | 11/2018 |
| EP | 3405139 A1 | 11/2018 |
| EP | 1858450 B1 | 12/2018 |
| EP | 2150208 B1 | 12/2018 |
| EP | 2326261 B1 | 12/2018 |
| EP | 2344075 B1 | 12/2018 |
| EP | 2370028 B1 | 12/2018 |
| EP | 2555709 B1 | 12/2018 |
| EP | 2564812 B1 | 12/2018 |
| EP | 2777618 B1 | 12/2018 |
| EP | 2814427 B1 | 12/2018 |
| EP | 2829240 B1 | 12/2018 |
| EP | 2911594 B1 | 12/2018 |
| EP | 2911729 B1 | 12/2018 |
| EP | 2954876 B1 | 12/2018 |
| EP | 2958520 B1 | 12/2018 |
| EP | 2958605 B1 | 12/2018 |
| EP | 3010446 B1 | 12/2018 |
| EP | 3064174 B1 | 12/2018 |
| EP | 3206628 B1 | 12/2018 |
| EP | 3242629 B1 | 12/2018 |
| EP | 3260085 B1 | 12/2018 |

(56) References Cited

FOREIGN PATENT DOCUMENTS

| | | | |
|---|---|---|---|
| EP | 3266416 | B1 | 12/2018 |
| EP | 3326583 | B1 | 12/2018 |
| EP | 3407834 | A1 | 12/2018 |
| EP | 3410984 | | 12/2018 |
| EP | 3410987 | A1 | 12/2018 |
| EP | 3415120 | A1 | 12/2018 |
| EP | 3417813 | A1 | 12/2018 |
| EP | 2129332 | B1 | 1/2019 |
| EP | 2196159 | B1 | 1/2019 |
| EP | 2370025 | B1 | 1/2019 |
| EP | 2549957 | B1 | 1/2019 |
| EP | 2819619 | B1 | 1/2019 |
| EP | 2849680 | B1 | 1/2019 |
| EP | 2856972 | B1 | 1/2019 |
| EP | 2866742 | B1 | 1/2019 |
| EP | 2884946 | B1 | 1/2019 |
| EP | 2948102 | B1 | 1/2019 |
| EP | 2979664 | B1 | 1/2019 |
| EP | 3043748 | B1 | 1/2019 |
| EP | 3145449 | B1 | 1/2019 |
| EP | 3288491 | A4 | 1/2019 |
| EP | 3332743 | B1 | 1/2019 |
| EP | 3427695 | | 1/2019 |
| EP | 3429507 | A1 | 1/2019 |
| EP | 3432832 | A1 | 1/2019 |
| EP | 3432834 | A1 | 1/2019 |
| EP | 1895943 | B1 | 2/2019 |
| EP | 2070490 | B1 | 2/2019 |
| EP | 2308425 | B1 | 2/2019 |
| EP | 2379009 | B1 | 2/2019 |
| EP | 2575685 | B1 | 2/2019 |
| EP | 2688562 | B1 | 2/2019 |
| EP | 2714068 | B1 | 2/2019 |
| EP | 2720641 | B1 | 2/2019 |
| EP | 2760375 | B1 | 2/2019 |
| EP | 2862590 | B1 | 2/2019 |
| EP | 2925259 | B1 | 2/2019 |
| EP | 2931179 | B1 | 2/2019 |
| EP | 3005983 | B1 | 2/2019 |
| EP | 3023117 | B1 | 2/2019 |
| EP | 3184083 | B1 | 2/2019 |
| EP | 3202333 | B1 | 2/2019 |
| EP | 3261583 | B1 | 2/2019 |
| EP | 3278832 | B1 | 2/2019 |
| EP | 3409454 | | 2/2019 |
| EP | 3435919 | A1 | 2/2019 |
| EP | 3441045 | A1 | 2/2019 |
| EP | 3442469 | A1 | 2/2019 |
| EP | 3443937 | | 2/2019 |
| EP | 1771132 | B1 | 3/2019 |
| EP | 1959866 | B1 | 3/2019 |
| EP | 2120794 | B1 | 3/2019 |
| EP | 2259728 | B1 | 3/2019 |
| EP | 2344074 | B1 | 3/2019 |
| EP | 2552356 | B1 | 3/2019 |
| EP | 2598044 | B1 | 3/2019 |
| EP | 2659861 | B1 | 3/2019 |
| EP | 2670357 | B1 | 3/2019 |
| EP | 2898902 | B1 | 3/2019 |
| EP | 2948098 | B1 | 3/2019 |
| EP | 2948101 | B1 | 3/2019 |
| EP | 2967865 | B1 | 3/2019 |
| EP | 2974695 | B1 | 3/2019 |
| EP | 3027243 | B1 | 3/2019 |
| EP | 3116446 | B1 | 3/2019 |
| EP | 3145445 | B1 | 3/2019 |
| EP | 3151783 | B1 | 3/2019 |
| EP | 3151784 | B1 | 3/2019 |
| EP | 3278768 | B1 | 3/2019 |
| EP | 3320943 | B1 | 3/2019 |
| EP | 3448314 | A1 | 3/2019 |
| EP | 3448315 | A1 | 3/2019 |
| EP | 3449969 | A1 | 3/2019 |
| EP | 3454785 | A1 | 3/2019 |
| EP | 3454786 | A1 | 3/2019 |
| EP | 3454789 | A1 | 3/2019 |
| EP | 3454794 | A1 | 3/2019 |
| EP | 3454795 | A1 | 3/2019 |
| EP | 3457987 | A1 | 3/2019 |
| EP | 3457988 | A1 | 3/2019 |
| EP | 3457990 | A1 | 3/2019 |
| EP | 3458136 | A2 | 3/2019 |
| EP | 3459499 | A2 | 3/2019 |
| EP | 1793745 | B1 | 4/2019 |
| EP | 1855623 | B1 | 4/2019 |
| EP | 2129333 | B1 | 4/2019 |
| EP | 2149349 | B1 | 4/2019 |
| EP | 2438888 | B1 | 4/2019 |
| EP | 2484309 | B1 | 4/2019 |
| EP | 2519268 | B1 | 4/2019 |
| EP | 2528545 | B1 | 4/2019 |
| EP | 2536358 | B1 | 4/2019 |
| EP | 2661239 | B1 | 4/2019 |
| EP | 2709563 | B1 | 4/2019 |
| EP | 2736451 | B1 | 4/2019 |
| EP | 2810619 | B1 | 4/2019 |
| EP | 2810622 | B1 | 4/2019 |
| EP | 2879589 | B1 | 4/2019 |
| EP | 2921198 | B1 | 4/2019 |
| EP | 2986256 | B1 | 4/2019 |
| EP | 3090704 | B1 | 4/2019 |
| EP | 3116445 | B1 | 4/2019 |
| EP | 3141217 | B1 | 4/2019 |
| EP | 3193745 | B1 | 4/2019 |
| EP | 3241525 | B1 | 4/2019 |
| EP | 3344167 | A4 | 4/2019 |
| EP | 3461531 | A1 | 4/2019 |
| EP | 3463120 | A1 | 4/2019 |
| EP | 3466373 | A1 | 4/2019 |
| EP | 3471662 | A1 | 4/2019 |
| EP | 1703870 | B1 | 5/2019 |
| EP | 1708642 | B1 | 5/2019 |
| EP | 2240121 | B1 | 5/2019 |
| EP | 2663259 | B1 | 5/2019 |
| EP | 2695586 | B1 | 5/2019 |
| EP | 2726018 | B1 | 5/2019 |
| EP | 2954872 | B1 | 5/2019 |
| EP | 3071150 | B1 | 5/2019 |
| EP | 3110370 | B1 | 5/2019 |
| EP | 3111890 | B1 | 5/2019 |
| EP | 3182932 | B1 | 5/2019 |
| EP | 3192472 | B1 | 5/2019 |
| EP | 3238661 | B1 | 5/2019 |
| EP | 3284503 | B1 | 5/2019 |
| EP | 3302364 | B1 | 5/2019 |
| EP | 3315094 | B1 | 5/2019 |
| EP | 3316818 | B1 | 5/2019 |
| EP | 3474778 | A1 | 5/2019 |
| EP | 3476366 | A1 | 5/2019 |
| EP | 3476424 | A1 | 5/2019 |
| EP | 3478224 | A1 | 5/2019 |
| EP | 3479797 | A1 | 5/2019 |
| EP | 3481335 | A1 | 5/2019 |
| EP | 3481336 | A1 | 5/2019 |
| EP | 3481338 | A1 | 5/2019 |
| EP | 3481339 | A1 | 5/2019 |
| EP | 3482718 | A1 | 5/2019 |
| EP | 3484412 | A1 | 5/2019 |
| EP | 3485847 | A1 | 5/2019 |
| EP | 3485848 | A1 | 5/2019 |
| EP | 3485933 | A1 | 5/2019 |
| EP | 3487420 | A1 | 5/2019 |
| EP | 3487452 | A1 | 5/2019 |
| EP | 3488822 | A1 | 5/2019 |
| EP | 1624792 | B1 | 6/2019 |
| EP | 1737394 | B1 | 6/2019 |
| EP | 1858451 | B1 | 6/2019 |
| EP | 1895944 | B1 | 6/2019 |
| EP | 1968487 | B1 | 6/2019 |
| EP | 2004095 | B1 | 6/2019 |
| EP | 2010102 | B1 | 6/2019 |
| EP | 2131788 | B1 | 6/2019 |
| EP | 2560580 | B1 | 6/2019 |
| EP | 2618782 | B1 | 6/2019 |

(56) References Cited

FOREIGN PATENT DOCUMENTS

| | | | |
|---|---|---|---|
| EP | 2868296 B1 | 6/2019 |
| EP | 2961358 B1 | 6/2019 |
| EP | 2967847 B1 | 6/2019 |
| EP | 2985006 B1 | 6/2019 |
| EP | 3033048 B1 | 6/2019 |
| EP | 3119451 B1 | 6/2019 |
| EP | 3131503 B1 | 6/2019 |
| EP | 3213718 B1 | 6/2019 |
| EP | 3275390 B1 | 6/2019 |
| EP | 3300692 B1 | 6/2019 |
| EP | 3326585 B1 | 6/2019 |
| EP | 3338737 B1 | 6/2019 |
| EP | 3357457 B1 | 6/2019 |
| EP | 3372198 B1 | 6/2019 |
| EP | 3490465 A1 | 6/2019 |
| EP | 3490500 A1 | 6/2019 |
| EP | 3490657 A1 | 6/2019 |
| EP | 3490659 A1 | 6/2019 |
| EP | 3496626 A1 | 6/2019 |
| EP | 3496664 A1 | 6/2019 |
| EP | 3498224 A1 | 6/2019 |
| EP | 3501454 A1 | 6/2019 |
| EP | 1659981 B1 | 7/2019 |
| EP | 1924223 B1 | 7/2019 |
| EP | 2249745 B1 | 7/2019 |
| EP | 2296744 B1 | 7/2019 |
| EP | 2331019 B1 | 7/2019 |
| EP | 2368527 B1 | 7/2019 |
| EP | 2509542 B1 | 7/2019 |
| EP | 2555710 B1 | 7/2019 |
| EP | 2575682 B1 | 7/2019 |
| EP | 2575683 B1 | 7/2019 |
| EP | 2640431 B1 | 7/2019 |
| EP | 2641572 B1 | 7/2019 |
| EP | 2649964 B1 | 7/2019 |
| EP | 2767260 B1 | 7/2019 |
| EP | 2777615 B1 | 7/2019 |
| EP | 2838476 B1 | 7/2019 |
| EP | 2861186 B1 | 7/2019 |
| EP | 2877124 B1 | 7/2019 |
| EP | 2877132 B1 | 7/2019 |
| EP | 2921565 B1 | 7/2019 |
| EP | 2938291 B1 | 7/2019 |
| EP | 2999433 B1 | 7/2019 |
| EP | 3145450 B1 | 7/2019 |
| EP | 3254644 B1 | 7/2019 |
| EP | 3315093 B1 | 7/2019 |
| EP | 3344189 B1 | 7/2019 |
| EP | 3503813 A1 | 7/2019 |
| EP | 3503846 A1 | 7/2019 |
| EP | 3503847 A1 | 7/2019 |
| EP | 3503848 A1 | 7/2019 |
| EP | 3505077 A1 | 7/2019 |
| EP | 3512465 A1 | 7/2019 |
| EP | 3515365 A1 | 7/2019 |
| EP | 3517075 A1 | 7/2019 |
| EP | 1861043 B1 | 8/2019 |
| EP | 2303190 B1 | 8/2019 |
| EP | 2593171 B1 | 8/2019 |
| EP | 2632393 B1 | 8/2019 |
| EP | 2663355 B1 | 8/2019 |
| EP | 2665509 B1 | 8/2019 |
| EP | 2688525 B1 | 8/2019 |
| EP | 2699201 B1 | 8/2019 |
| EP | 2755564 B1 | 8/2019 |
| EP | 2769681 B1 | 8/2019 |
| EP | 2793751 B1 | 8/2019 |
| EP | 2900177 B1 | 8/2019 |
| EP | 2967536 B1 | 8/2019 |
| EP | 3050541 B1 | 8/2019 |
| EP | 3102152 B1 | 8/2019 |
| EP | 3157607 B1 | 8/2019 |
| EP | 3231392 B1 | 8/2019 |
| EP | 3284411 B1 | 8/2019 |
| EP | 3328318 B1 | 8/2019 |
| EP | 3348233 B1 | 8/2019 |
| EP | 3366262 B1 | 8/2019 |
| EP | 3527170 A1 | 8/2019 |
| EP | 3530236 A1 | 8/2019 |
| EP | 2358297 B1 | 9/2019 |
| EP | 2368525 B1 | 9/2019 |
| EP | 2542186 B1 | 9/2019 |
| EP | 2656863 B1 | 9/2019 |
| EP | 3003221 B1 | 9/2019 |
| EP | 3003452 B1 | 9/2019 |
| EP | 3220971 B1 | 9/2019 |
| EP | 3223874 B1 | 9/2019 |
| EP | 3288495 B1 | 9/2019 |
| EP | 3311776 B1 | 9/2019 |
| EP | 3334379 B1 | 9/2019 |
| EP | 3531975 A1 | 9/2019 |
| EP | 3534840 A1 | 9/2019 |
| EP | 3534841 A1 | 9/2019 |
| EP | 3534845 A2 | 9/2019 |
| EP | 3535010 A1 | 9/2019 |
| EP | 3538026 A1 | 9/2019 |
| EP | 3538027 A1 | 9/2019 |
| EP | 3539508 A1 | 9/2019 |
| EP | 3539509 A1 | 9/2019 |
| EP | 3541316 A1 | 9/2019 |
| EP | 3541325 A1 | 9/2019 |
| EP | 3541328 A1 | 9/2019 |
| EP | 3542758 A1 | 9/2019 |
| EP | 1740265 B1 | 10/2019 |
| EP | 2039756 B1 | 10/2019 |
| EP | 2456506 B1 | 10/2019 |
| EP | 2470122 B1 | 10/2019 |
| EP | 2613738 B1 | 10/2019 |
| EP | 2637607 B1 | 10/2019 |
| EP | 2674174 B1 | 10/2019 |
| EP | 2811923 B1 | 10/2019 |
| EP | 2901967 B1 | 10/2019 |
| EP | 3010431 B1 | 10/2019 |
| EP | 3019091 B1 | 10/2019 |
| EP | 3019123 B1 | 10/2019 |
| EP | 3057522 B1 | 10/2019 |
| EP | 3067075 B1 | 10/2019 |
| EP | 3146937 B1 | 10/2019 |
| EP | 3238777 B1 | 10/2019 |
| EP | 3359211 B1 | 10/2019 |
| EP | 3388026 B1 | 10/2019 |
| EP | 3432806 B1 | 10/2019 |
| EP | 3496626 A4 | 10/2019 |
| EP | 3544548 A1 | 10/2019 |
| EP | 3545905 A1 | 10/2019 |
| EP | 3547936 A1 | 10/2019 |
| EP | 3547966 A1 | 10/2019 |
| EP | 3549555 A1 | 10/2019 |
| EP | 3549556 A1 | 10/2019 |
| EP | 3552585 A1 | 10/2019 |
| EP | 3554424 A1 | 10/2019 |
| EP | 3556323 A1 | 10/2019 |
| EP | 3558165 A1 | 10/2019 |
| EP | 3558168 A1 | 10/2019 |
| EP | 3558169 A2 | 10/2019 |
| EP | 2043559 B1 | 11/2019 |
| EP | 2358308 B1 | 11/2019 |
| EP | 2405863 B1 | 11/2019 |
| EP | 2701633 B1 | 11/2019 |
| EP | 2898857 B1 | 11/2019 |
| EP | 2967853 B1 | 11/2019 |
| EP | 3009104 B1 | 11/2019 |
| EP | 3021792 B1 | 11/2019 |
| EP | 3076900 B1 | 11/2019 |
| EP | 3111889 B1 | 11/2019 |
| EP | 3142607 B1 | 11/2019 |
| EP | 3167850 B1 | 11/2019 |
| EP | 3397205 B1 | 11/2019 |
| EP | 3563799 | 11/2019 |
| EP | 3563806 A1 | 11/2019 |
| EP | 3570779 A1 | 11/2019 |
| EP | 3572045 A1 | 11/2019 |
| EP | 3572117 A1 | 11/2019 |
| EP | 3479800 A4 | 12/2019 |

(56) References Cited

FOREIGN PATENT DOCUMENTS

| | | | |
|---|---|---|---|
| EP | 3576677 | A1 | 12/2019 |
| EP | 3579761 | A2 | 12/2019 |
| EP | 3579788 | A1 | 12/2019 |
| EP | 3582697 | A1 | 12/2019 |
| EP | 3583922 | A1 | 12/2019 |
| EP | 3445443 | A4 | 1/2020 |
| EP | 3590471 | A1 | 1/2020 |
| EP | 3590472 | A1 | 1/2020 |
| EP | 3592284 | A1 | 1/2020 |
| EP | 3592288 | A1 | 1/2020 |
| EP | 3592289 | A1 | 1/2020 |
| EP | 3593763 | A1 | 1/2020 |
| EP | 3595588 | A1 | 1/2020 |
| EP | 3600156 | | 2/2020 |
| EP | 3600159 | A1 | 2/2020 |
| EP | 3606443 | | 2/2020 |
| EP | 3606472 | A1 | 2/2020 |
| EP | 2241287 | B2 | 3/2020 |
| EP | 2376013 | B1 | 3/2020 |
| EP | 2911593 | B1 | 3/2020 |
| EP | 2995279 | B1 | 3/2020 |
| EP | 3009103 | B1 | 3/2020 |
| EP | 3038664 | B1 | 3/2020 |
| EP | 3167848 | B1 | 3/2020 |
| EP | 3175822 | B1 | 3/2020 |
| EP | 3179960 | B1 | 3/2020 |
| EP | 3280479 | B1 | 3/2020 |
| EP | 3616651 | A1 | 3/2020 |
| EP | 3619136 | A1 | 3/2020 |
| EP | 3626208 | A1 | 3/2020 |
| EP | 1667614 | B2 | 4/2020 |
| EP | 2119417 | B2 | 4/2020 |
| EP | 2155114 | B1 | 4/2020 |
| EP | 2299937 | B1 | 4/2020 |
| EP | 2331016 | B1 | 4/2020 |
| EP | 2376013 | B8 | 4/2020 |
| EP | 2413843 | B1 | 4/2020 |
| EP | 2854705 | B1 | 4/2020 |
| EP | 2918249 | B1 | 4/2020 |
| EP | 2922593 | B1 | 4/2020 |
| EP | 2950753 | B1 | 4/2020 |
| EP | 2967810 | B1 | 4/2020 |
| EP | 3110367 | B1 | 4/2020 |
| EP | 3111888 | B1 | 4/2020 |
| EP | 3128927 | B1 | 4/2020 |
| EP | 3134032 | B1 | 4/2020 |
| EP | 3142606 | B1 | 4/2020 |
| EP | 3270825 | B1 | 4/2020 |
| EP | 3300696 | B1 | 4/2020 |
| EP | 3316823 | B1 | 4/2020 |
| EP | 3334487 | B1 | 4/2020 |
| EP | 3342355 | B1 | 4/2020 |
| EP | 3373863 | B1 | 4/2020 |
| EP | 3459498 | B1 | 4/2020 |
| EP | 3470105 | B1 | 4/2020 |
| EP | 3628274 | A1 | 4/2020 |
| EP | 3632338 | A1 | 4/2020 |
| EP | 3636312 | A1 | 4/2020 |
| EP | 3639792 | A1 | 4/2020 |
| EP | 3639888 | A1 | 4/2020 |
| EP | 3643273 | A1 | 4/2020 |
| EP | 1895942 | B1 | 5/2020 |
| EP | 2120821 | B1 | 5/2020 |
| EP | 2437688 | B1 | 5/2020 |
| EP | 2785281 | B1 | 5/2020 |
| EP | 2852354 | B1 | 5/2020 |
| EP | 2884906 | B1 | 5/2020 |
| EP | 2999412 | B1 | 5/2020 |
| EP | 3060174 | B1 | 5/2020 |
| EP | 3071147 | B1 | 5/2020 |
| EP | 3104812 | B1 | 5/2020 |
| EP | 3139861 | B1 | 5/2020 |
| EP | 3232989 | B1 | 5/2020 |
| EP | 3294219 | B1 | 5/2020 |
| EP | 3298970 | B1 | 5/2020 |
| EP | 3302366 | B1 | 5/2020 |
| EP | 3323389 | B1 | 5/2020 |
| EP | 3332744 | B1 | 5/2020 |
| EP | 3402440 | B1 | 5/2020 |
| EP | 3417813 | B1 | 5/2020 |
| EP | 3417831 | B1 | 5/2020 |
| EP | 3457987 | B1 | 5/2020 |
| EP | 3484413 | B1 | 5/2020 |
| EP | 3531975 | B1 | 5/2020 |
| EP | 3644866 | A1 | 5/2020 |
| EP | 3646822 | A1 | 5/2020 |
| EP | 3646824 | A1 | 5/2020 |
| EP | 3646825 | A1 | 5/2020 |
| EP | 3648706 | A1 | 5/2020 |
| EP | 3648709 | A1 | 5/2020 |
| EP | 3656354 | A1 | 5/2020 |
| EP | 2072027 | B1 | 6/2020 |
| EP | 2331016 | B8 | 6/2020 |
| EP | 2616007 | B1 | 6/2020 |
| EP | 2967856 | B1 | 6/2020 |
| EP | 3042635 | B1 | 6/2020 |
| EP | 3060165 | B1 | 6/2020 |
| EP | 3280338 | B1 | 6/2020 |
| EP | 3283010 | B1 | 6/2020 |
| EP | 3400908 | B1 | 6/2020 |
| EP | 3494928 | B1 | 6/2020 |
| EP | 3498225 | B1 | 6/2020 |
| EP | 3583920 | B1 | 6/2020 |
| EP | 3659553 | A1 | 6/2020 |
| EP | 3661429 | | 6/2020 |
| EP | 3661436 | A1 | 6/2020 |
| EP | 3668450 | A1 | 6/2020 |
| EP | 3668452 | A1 | 6/2020 |
| EP | 3669828 | A1 | 6/2020 |
| EP | 3669829 | A1 | 6/2020 |
| EP | 164833982 | | 6/2020 |
| EP | 2271284 | B1 | 7/2020 |
| EP | 2291145 | B1 | 7/2020 |
| EP | 2512952 | B1 | 7/2020 |
| EP | 2558029 | B1 | 7/2020 |
| EP | 2693985 | B1 | 7/2020 |
| EP | 2858708 | B1 | 7/2020 |
| EP | 2862546 | B1 | 7/2020 |
| EP | 2967807 | B1 | 7/2020 |
| EP | 2967866 | B1 | 7/2020 |
| EP | 3061421 | B1 | 7/2020 |
| EP | 3107497 | B1 | 7/2020 |
| EP | 3139862 | B1 | 7/2020 |
| EP | 3423000 | B1 | 7/2020 |
| EP | 3441045 | B1 | 7/2020 |
| EP | 3451972 | B1 | 7/2020 |
| EP | 3501454 | B1 | 7/2020 |
| EP | 3512466 | B1 | 7/2020 |
| EP | 3616652 | B1 | 7/2020 |
| EP | 3672528 | A1 | 7/2020 |
| EP | 3672529 | A1 | 7/2020 |
| EP | 3672532 | A1 | 7/2020 |
| EP | 3673925 | A1 | 7/2020 |
| EP | 3679894 | A1 | 7/2020 |
| EP | 3681439 | A1 | 7/2020 |
| EP | 3681441 | A1 | 7/2020 |
| EP | 3682852 | A1 | 7/2020 |
| EP | 3682854 | A1 | 7/2020 |
| EP | 3685802 | A1 | 7/2020 |
| EP | 2367505 | B1 | 8/2020 |
| EP | 2497445 | B1 | 8/2020 |
| EP | 2537486 | B1 | 8/2020 |
| EP | 2777616 | B1 | 8/2020 |
| EP | 3007651 | B1 | 8/2020 |
| EP | 3052053 | B1 | 8/2020 |
| EP | 3237033 | B1 | 8/2020 |
| EP | 3388005 | B1 | 8/2020 |
| EP | 3410986 | B1 | 8/2020 |
| EP | 3451974 | B1 | 8/2020 |
| EP | 3463192 | B1 | 8/2020 |
| EP | 3554423 | B1 | 8/2020 |
| EP | 3568089 | A4 | 8/2020 |
| EP | 3573544 | B1 | 8/2020 |
| EP | 3634255 | B1 | 8/2020 |

(56) References Cited

FOREIGN PATENT DOCUMENTS

| | | | |
|---|---|---|---|
| EP | 3689299 | A1 | 8/2020 |
| EP | 3691567 | A1 | 8/2020 |
| EP | 3695810 | A1 | 8/2020 |
| EP | 3697342 | A1 | 8/2020 |
| EP | 3697346 | A1 | 8/2020 |
| EP | 2485795 | B1 | 9/2020 |
| EP | 3125777 | B1 | 9/2020 |
| EP | 3182930 | B1 | 9/2020 |
| EP | 3285690 | B1 | 9/2020 |
| EP | 3459500 | B1 | 9/2020 |
| EP | 3570782 | B1 | 9/2020 |
| EP | 3700467 | A1 | 9/2020 |
| EP | 3711711 | A1 | 9/2020 |
| EP | 3714936 | A1 | 9/2020 |
| EP | 2979667 | B2 | 10/2020 |
| EP | 3193783 | B1 | 10/2020 |
| EP | 3490501 | B1 | 10/2020 |
| EP | 3718509 | A1 | 10/2020 |
| EP | 3720363 | A1 | 10/2020 |
| EP | 3721811 | A1 | 10/2020 |
| EP | 2387973 | B1 | 11/2020 |
| EP | 2427144 | B1 | 11/2020 |
| EP | 2506777 | B1 | 11/2020 |
| EP | 2793743 | B1 | 11/2020 |
| EP | 2825203 | B1 | 11/2020 |
| EP | 2863842 | B1 | 11/2020 |
| EP | 2967700 | B1 | 11/2020 |
| EP | 2977026 | B1 | 11/2020 |
| EP | 3139864 | B1 | 11/2020 |
| EP | 3145451 | B1 | 11/2020 |
| EP | 3156007 | B1 | 11/2020 |
| EP | 3244834 | B1 | 11/2020 |
| EP | 3298987 | B1 | 11/2020 |
| EP | 3302362 | B1 | 11/2020 |
| EP | 3311777 | B1 | 11/2020 |
| EP | 3316819 | B1 | 11/2020 |
| EP | 3361988 | B1 | 11/2020 |
| EP | 3503813 | B1 | 11/2020 |
| EP | 3527170 | B1 | 11/2020 |
| EP | 3530236 | B1 | 11/2020 |
| EP | 3590471 | B1 | 11/2020 |
| EP | 3593762 | B1 | 11/2020 |
| EP | 3737336 | A1 | 11/2020 |
| EP | 3740162 | A1 | 11/2020 |
| EP | 2370138 | B1 | 12/2020 |
| EP | 2445450 | B1 | 12/2020 |
| EP | 2739250 | B1 | 12/2020 |
| EP | 2877123 | B1 | 12/2020 |
| EP | 2967834 | B1 | 12/2020 |
| EP | 2996632 | B1 | 12/2020 |
| EP | 3090703 | B1 | 12/2020 |
| EP | 3191025 | B1 | 12/2020 |
| EP | 3202371 | B1 | 12/2020 |
| EP | 3316822 | B1 | 12/2020 |
| EP | 3334382 | B1 | 12/2020 |
| EP | 3337424 | B1 | 12/2020 |
| EP | 3367896 | B1 | 12/2020 |
| EP | 3368582 | B1 | 12/2020 |
| EP | 3397208 | B1 | 12/2020 |
| EP | 3476366 | B1 | 12/2020 |
| EP | 3481303 | B1 | 12/2020 |
| EP | 3538028 | B1 | 12/2020 |
| EP | 3539510 | B1 | 12/2020 |
| EP | 3544548 | B1 | 12/2020 |
| EP | 3545906 | B1 | 12/2020 |
| EP | 3572117 | B1 | 12/2020 |
| EP | 3593763 | B1 | 12/2020 |
| EP | 3744291 | A1 | 12/2020 |
| EP | 3749254 | A1 | 12/2020 |
| EP | 3753535 | A1 | 12/2020 |
| EP | 3756623 | A1 | 12/2020 |
| EP | 2334261 | B1 | 1/2021 |
| EP | 2349096 | B1 | 1/2021 |
| EP | 2568924 | B1 | 1/2021 |
| EP | 2699202 | B1 | 1/2021 |
| EP | 2713894 | B1 | 1/2021 |
| EP | 2835112 | B1 | 1/2021 |
| EP | 3040054 | B1 | 1/2021 |
| EP | 3131502 | B1 | 1/2021 |
| EP | 3197397 | B1 | 1/2021 |
| EP | 3256178 | B1 | 1/2021 |
| EP | 3290007 | B1 | 1/2021 |
| EP | 3316821 | B1 | 1/2021 |
| EP | 3337412 | B1 | 1/2021 |
| EP | 3432834 | B1 | 1/2021 |
| EP | 3454786 | B1 | 1/2021 |
| EP | 3474778 | B1 | 1/2021 |
| EP | 3528748 | B1 | 1/2021 |
| EP | 3547966 | B1 | 1/2021 |
| EP | 3603576 | B1 | 1/2021 |
| EP | 3758651 | A1 | 1/2021 |
| EP | 3760164 | A1 | 1/2021 |
| EP | 3763331 | A1 | 1/2021 |
| EP | 3769721 | A1 | 1/2021 |
| EP | 190688381 | | 1/2021 |
| EP | 2273951 | B1 | 2/2021 |
| EP | 2379008 | B1 | 2/2021 |
| EP | 2996641 | B1 | 2/2021 |
| EP | 3043747 | B1 | 2/2021 |
| EP | 3340936 | B1 | 2/2021 |
| EP | 3457985 | B1 | 2/2021 |
| EP | 3503847 | B1 | 2/2021 |
| EP | 3538027 | B1 | 2/2021 |
| EP | 3558168 | B1 | 2/2021 |
| EP | 3581232 | B1 | 2/2021 |
| EP | 3656354 | B1 | 2/2021 |
| EP | 3697324 | B1 | 2/2021 |
| EP | 3773271 | A1 | 2/2021 |
| EP | 3773329 | A1 | 2/2021 |
| EP | 2299938 | B1 | 3/2021 |
| EP | 2470121 | B1 | 3/2021 |
| EP | 2564811 | B1 | 3/2021 |
| EP | 2679198 | B1 | 3/2021 |
| EP | 3068346 | B1 | 3/2021 |
| EP | 3160394 | B1 | 3/2021 |
| EP | 3169245 | B1 | 3/2021 |
| EP | 3178443 | B1 | 3/2021 |
| EP | 3184081 | B1 | 3/2021 |
| EP | 3226956 | B1 | 3/2021 |
| EP | 3324892 | B1 | 3/2021 |
| EP | 3334354 | B1 | 3/2021 |
| EP | 3402446 | B1 | 3/2021 |
| EP | 3442469 | B1 | 3/2021 |
| EP | 3503851 | B1 | 3/2021 |
| EP | 3506855 | B1 | 3/2021 |
| EP | 3531979 | B1 | 3/2021 |
| EP | 3535010 | B1 | 3/2021 |
| EP | 3581151 | B1 | 3/2021 |
| EP | 3590472 | B1 | 3/2021 |
| EP | 3593760 | B1 | 3/2021 |
| EP | 3646825 | B1 | 3/2021 |
| EP | 3649985 | B1 | 3/2021 |
| EP | 3787561 | A1 | 3/2021 |
| EP | 3790501 | A1 | 3/2021 |
| EP | 3791795 | A1 | 3/2021 |
| EP | 3791828 | A1 | 3/2021 |
| EP | 3796872 | A1 | 3/2021 |
| EP | 3796873 | A1 | 3/2021 |
| EP | 3796875 | A1 | 3/2021 |
| EP | 3796876 | A1 | 3/2021 |
| EP | 1734872 | B1 | 4/2021 |
| EP | 2594230 | B1 | 4/2021 |
| EP | 2624785 | B1 | 4/2021 |
| EP | 2670349 | B1 | 4/2021 |
| EP | 2793752 | B1 | 4/2021 |
| EP | 2823769 | B1 | 4/2021 |
| EP | 2964152 | B1 | 4/2021 |
| EP | 3253331 | B1 | 4/2021 |
| EP | 3290004 | B1 | 4/2021 |
| EP | 3311778 | B1 | 4/2021 |
| EP | 3367979 | B1 | 4/2021 |
| EP | 3454794 | B1 | 4/2021 |
| EP | 3487420 | B1 | 4/2021 |
| EP | 3558165 | B1 | 4/2021 |

(56) References Cited

FOREIGN PATENT DOCUMENTS

| | | | |
|---|---|---|---|
| EP | 3616651 | B1 | 4/2021 |
| EP | 3619136 | B1 | 4/2021 |
| EP | 3626208 | B1 | 4/2021 |
| EP | 3632379 | B1 | 4/2021 |
| EP | 3646823 | B1 | 4/2021 |
| EP | 3646824 | B1 | 4/2021 |
| EP | 3653173 | B1 | 4/2021 |
| EP | 1951155 | B1 | 5/2021 |
| EP | 2073755 | B1 | 5/2021 |
| EP | 2948100 | B1 | 5/2021 |
| EP | 3099270 | B1 | 5/2021 |
| EP | 3150172 | B1 | 5/2021 |
| EP | 3178445 | B1 | 5/2021 |
| EP | 3310301 | B1 | 5/2021 |
| EP | 3582697 | B1 | 5/2021 |
| EP | 3592295 | B1 | 5/2021 |
| EP | 3639888 | B1 | 5/2021 |
| EP | 3669828 | B1 | 5/2021 |
| EP | 2471492 | B1 | 6/2021 |
| EP | 2486894 | B1 | 6/2021 |
| EP | 2750630 | B1 | 6/2021 |
| EP | 3247312 | B1 | 6/2021 |
| EP | 3294215 | B1 | 6/2021 |
| EP | 3323353 | B1 | 6/2021 |
| EP | 3360513 | B1 | 6/2021 |
| EP | 3488821 | B1 | 6/2021 |
| EP | 3549555 | B1 | 6/2021 |
| EP | 3576677 | B1 | 6/2021 |
| EP | 3632338 | B1 | 6/2021 |
| EP | 3834879 | A1 | 6/2021 |
| EP | 2381895 | B1 | 7/2021 |
| EP | 2611389 | B1 | 7/2021 |
| EP | 2779945 | B1 | 7/2021 |
| EP | 3193740 | B1 | 7/2021 |
| EP | 3206629 | B1 | 7/2021 |
| EP | 3277222 | B1 | 7/2021 |
| EP | 3400907 | B1 | 7/2021 |
| EP | 3435919 | B1 | 7/2021 |
| EP | 3522800 | B1 | 7/2021 |
| EP | 3539508 | B1 | 7/2021 |
| EP | 3539509 | B1 | 7/2021 |
| EP | 3572044 | B1 | 7/2021 |
| EP | 3592289 | B1 | 7/2021 |
| EP | 3668450 | B1 | 7/2021 |
| EP | 3681439 | B1 | 7/2021 |
| EP | 3691567 | B1 | 7/2021 |
| EP | 3789077 | A4 | 7/2021 |
| EP | 3846740 | A1 | 7/2021 |
| EP | 3849472 | A1 | 7/2021 |
| EP | 2558032 | B1 | 8/2021 |
| EP | 2992857 | B1 | 8/2021 |
| EP | 2994075 | B1 | 8/2021 |
| EP | 3038539 | B1 | 8/2021 |
| EP | 3287099 | B1 | 8/2021 |
| EP | 3348235 | B1 | 8/2021 |
| EP | 3643273 | B1 | 8/2021 |
| EP | 3646822 | B1 | 8/2021 |
| EP | 3658215 | B1 | 8/2021 |
| EP | 3659553 | B1 | 8/2021 |
| EP | 3723665 | B1 | 8/2021 |
| EP | 3744290 | B1 | 8/2021 |
| EP | 3860530 | A1 | 8/2021 |
| EP | 3863567 | A1 | 8/2021 |
| EP | 2040645 | B1 | 9/2021 |
| EP | 2329796 | B1 | 9/2021 |
| EP | 3125827 | B1 | 9/2021 |
| EP | 3137146 | B1 | 9/2021 |
| EP | 3288494 | B1 | 9/2021 |
| EP | 3288497 | B1 | 9/2021 |
| EP | 3446660 | B1 | 9/2021 |
| EP | 3454784 | B1 | 9/2021 |
| EP | 3456293 | B1 | 9/2021 |
| EP | 3457989 | B1 | 9/2021 |
| EP | 3496664 | B1 | 9/2021 |
| EP | 3503848 | B1 | 9/2021 |
| EP | 3512465 | B1 | 9/2021 |
| EP | 3544664 | B1 | 9/2021 |
| EP | 3568089 | B1 | 9/2021 |
| EP | 3592288 | B1 | 9/2021 |
| EP | 3606472 | B1 | 9/2021 |
| EP | 3669829 | B1 | 9/2021 |
| EP | 3672528 | B1 | 9/2021 |
| EP | 3833302 | A4 | 9/2021 |
| EP | 3870110 | A1 | 9/2021 |
| EP | 2249711 | B1 | 10/2021 |
| EP | 2538883 | B1 | 10/2021 |
| EP | 2723273 | B1 | 10/2021 |
| EP | 3119351 | B1 | 10/2021 |
| EP | 3267946 | B1 | 10/2021 |
| EP | 3275404 | B1 | 10/2021 |
| EP | 3280482 | B1 | 10/2021 |
| EP | 3334381 | B1 | 10/2021 |
| EP | 3639792 | B1 | 10/2021 |
| EP | 3886762 | A1 | 10/2021 |
| EP | 3886763 | A1 | 10/2021 |
| EP | 3892240 | A1 | 10/2021 |
| EP | 3897454 | A1 | 10/2021 |
| EP | 3900679 | A1 | 10/2021 |
| EP | 2331018 | B1 | 11/2021 |
| EP | 2429455 | B1 | 11/2021 |
| EP | 2538878 | B1 | 11/2021 |
| EP | 2699302 | B1 | 11/2021 |
| EP | 2706958 | B1 | 11/2021 |
| EP | 2892467 | B1 | 11/2021 |
| EP | 2999434 | B1 | 11/2021 |
| EP | 3024527 | B1 | 11/2021 |
| EP | 3061422 | B1 | 11/2021 |
| EP | 3107500 | B1 | 11/2021 |
| EP | 3110468 | B1 | 11/2021 |
| EP | 3154474 | B1 | 11/2021 |
| EP | 3213715 | B1 | 11/2021 |
| EP | 3256076 | B1 | 11/2021 |
| EP | 3288499 | B1 | 11/2021 |
| EP | 3360514 | B1 | 11/2021 |
| EP | 3429507 | B1 | 11/2021 |
| EP | 3445443 | B1 | 11/2021 |
| EP | 3454785 | B1 | 11/2021 |
| EP | 3505077 | B1 | 11/2021 |
| EP | 3672529 | B1 | 11/2021 |
| EP | 3760164 | B1 | 11/2021 |
| EP | 3908228 | A1 | 11/2021 |
| EP | 3912595 | A1 | 11/2021 |
| EP | 3912596 | A1 | 11/2021 |
| EP | 2358307 | B1 | 12/2021 |
| EP | 2765954 | B1 | 12/2021 |
| EP | 2991584 | B1 | 12/2021 |
| EP | 3283011 | B1 | 12/2021 |
| EP | 3288479 | B1 | 12/2021 |
| EP | 3344167 | B1 | 12/2021 |
| EP | 3410987 | B1 | 12/2021 |
| EP | 3481339 | B1 | 12/2021 |
| EP | 3482718 | B1 | 12/2021 |
| EP | 3490465 | B1 | 12/2021 |
| EP | 3498224 | B1 | 12/2021 |
| EP | 3503846 | B1 | 12/2021 |
| EP | 3592284 | B1 | 12/2021 |
| EP | 3749254 | B1 | 12/2021 |
| EP | 3914191 | A1 | 12/2021 |
| EP | 3915493 | A1 | 12/2021 |
| EP | 3740162 | B1 | 1/2022 |
| EP | 3294218 | B1 | 2/2022 |
| EP | 3457988 | B1 | 2/2022 |
| EP | 3481336 | B1 | 2/2022 |
| EP | 3673925 | B1 | 2/2022 |
| EP | 3689299 | B1 | 2/2022 |
| EP | 3753535 | B1 | 2/2022 |
| EP | 3860530 | B1 | 2/2022 |
| EP | 2520249 | B1 | 3/2022 |
| EP | 2558033 | B1 | 3/2022 |
| EP | 2623068 | B1 | 3/2022 |
| EP | 2866737 | B1 | 3/2022 |
| EP | 3107495 | B1 | 3/2022 |
| EP | 3160396 | B1 | 3/2022 |
| EP | 3193782 | B1 | 3/2022 |

(56) References Cited

FOREIGN PATENT DOCUMENTS

| | | | |
|---|---|---|---|
| EP | 3334380 | B1 | 3/2022 |
| EP | 3355800 | B1 | 3/2022 |
| EP | 3479797 | B1 | 3/2022 |
| EP | 3479800 | B1 | 3/2022 |
| EP | 3547936 | B1 | 3/2022 |
| EP | 3628274 | B1 | 3/2022 |
| EP | 3679894 | B1 | 3/2022 |
| EP | 3711711 | B1 | 3/2022 |
| EP | 3714936 | B1 | 3/2022 |
| EP | 3787561 | B1 | 3/2022 |
| EP | 3791795 | B1 | 3/2022 |
| EP | 3962415 | A1 | 3/2022 |
| EP | 2488126 | B1 | 4/2022 |
| EP | 2536360 | B1 | 4/2022 |
| EP | 2611388 | B1 | 4/2022 |
| EP | 2651336 | B1 | 4/2022 |
| EP | 2699200 | B1 | 4/2022 |
| EP | 2916781 | B1 | 4/2022 |
| EP | 3174502 | B1 | 4/2022 |
| EP | 3209221 | B1 | 4/2022 |
| EP | 3302297 | B1 | 4/2022 |
| EP | 3349693 | B1 | 4/2022 |
| EP | 3487451 | B1 | 4/2022 |
| EP | 3500184 | B1 | 4/2022 |
| EP | 3600159 | B1 | 4/2022 |
| EP | 3628239 | B1 | 4/2022 |
| EP | 3644866 | B1 | 4/2022 |
| EP | 3681441 | B1 | 4/2022 |
| EP | 3796873 | B1 | 4/2022 |
| EP | 2268231 | B1 | 5/2022 |
| EP | 2856973 | B1 | 5/2022 |
| EP | 2962664 | B1 | 5/2022 |
| EP | 3311774 | B1 | 5/2022 |
| EP | 3335670 | B1 | 5/2022 |
| EP | 3403616 | B1 | 5/2022 |
| EP | 3445290 | B1 | 5/2022 |
| EP | 3541316 | B1 | 5/2022 |
| EP | 3648709 | B1 | 5/2022 |
| EP | 3695810 | B1 | 5/2022 |
| EP | 3721811 | B1 | 5/2022 |
| EP | 3773271 | B1 | 5/2022 |
| EP | 2538893 | B1 | 6/2022 |
| EP | 2575681 | B1 | 6/2022 |
| EP | 2583640 | B1 | 6/2022 |
| EP | 3071149 | B1 | 6/2022 |
| EP | 3253332 | B1 | 6/2022 |
| EP | 3283009 | B1 | 6/2022 |
| EP | 3296979 | B1 | 6/2022 |
| EP | 3298988 | B1 | 6/2022 |
| EP | 3342377 | B1 | 6/2022 |
| EP | 3365349 | B1 | 6/2022 |
| EP | 3397206 | B1 | 6/2022 |
| EP | 3426194 | B1 | 6/2022 |
| EP | 3595588 | B1 | 6/2022 |
| EP | 3636312 | B1 | 6/2022 |
| EP | 3661436 | B1 | 6/2022 |
| EP | 3790501 | B1 | 6/2022 |
| EP | 3846740 | B1 | 6/2022 |
| EP | 3849472 | B1 | 6/2022 |
| EP | 3897454 | B1 | 6/2022 |
| EP | 4014928 | | 6/2022 |
| EP | 2621409 | B1 | 7/2022 |
| EP | 2787926 | B1 | 7/2022 |
| EP | 2838473 | B1 | 7/2022 |
| EP | 2950752 | B1 | 7/2022 |
| EP | 3060171 | B1 | 7/2022 |
| EP | 3206631 | B1 | 7/2022 |
| EP | 3245980 | B1 | 7/2022 |
| EP | 3256073 | B1 | 7/2022 |
| EP | 3311783 | B1 | 7/2022 |
| EP | 3347182 | B1 | 7/2022 |
| EP | 3389557 | B1 | 7/2022 |
| EP | 3463120 | B1 | 7/2022 |
| EP | 3579788 | B1 | 7/2022 |
| EP | 3756623 | B1 | 7/2022 |
| EP | 3796872 | B1 | 7/2022 |
| EP | 3796876 | B1 | 7/2022 |
| EP | 2313152 | B1 | 8/2022 |
| EP | 2688516 | B1 | 8/2022 |
| EP | 2849678 | B1 | 8/2022 |
| EP | 2950751 | B1 | 8/2022 |
| EP | 2964153 | B1 | 8/2022 |
| EP | 3019092 | B1 | 8/2022 |
| EP | 3184082 | B1 | 8/2022 |
| EP | 3231395 | B1 | 8/2022 |
| EP | 3266417 | B1 | 8/2022 |
| EP | 3407834 | B1 | 8/2022 |
| EP | 3458136 | B1 | 8/2022 |
| EP | 3459499 | B1 | 8/2022 |
| EP | 3471662 | B1 | 8/2022 |
| EP | 3484412 | B1 | 8/2022 |
| EP | 3534841 | B1 | 8/2022 |
| EP | 3541328 | B1 | 8/2022 |
| EP | 3672532 | B1 | 8/2022 |
| EP | 3718509 | B1 | 8/2022 |
| EP | 3769721 | B1 | 8/2022 |
| EP | 3789077 | B1 | 8/2022 |
| EP | 3908228 | B1 | 8/2022 |
| EP | 3915493 | B1 | 8/2022 |
| EP | 3967274 | B1 | 8/2022 |
| EP | 2670351 | B1 | 9/2022 |
| EP | 2777617 | B1 | 9/2022 |
| EP | 2810620 | B1 | 9/2022 |
| EP | 2922592 | B1 | 9/2022 |
| EP | 3038567 | B1 | 9/2022 |
| EP | 3096713 | B1 | 9/2022 |
| EP | 3220857 | B1 | 9/2022 |
| EP | 3448315 | B1 | 9/2022 |
| EP | 3481335 | B1 | 9/2022 |
| EP | 3520715 | B1 | 9/2022 |
| EP | 3645065 | B1 | 9/2022 |
| EP | 3737336 | B1 | 9/2022 |
| EP | 2104470 | B1 | 10/2022 |
| EP | 2536353 | B1 | 10/2022 |
| EP | 2991588 | B1 | 10/2022 |
| EP | 3043755 | B1 | 10/2022 |
| EP | 3288491 | B1 | 10/2022 |
| EP | 3466373 | B1 | 10/2022 |
| EP | 3552585 | B1 | 10/2022 |
| EP | 3791828 | B1 | 10/2022 |
| EP | 3914191 | B1 | 10/2022 |
| EP | 2538882 | | 11/2022 |
| EP | 2698129 | | 11/2022 |
| EP | 2959866 | | 11/2022 |
| EP | 3175823 | | 11/2022 |
| EP | 3280358 | | 11/2022 |
| EP | 3340923 | | 11/2022 |
| EP | 3478224 | | 11/2022 |
| EP | 3490659 | | 11/2022 |
| EP | 3744291 | | 11/2022 |
| FR | 2815844 | B1 | 1/2003 |
| FR | 2826863 | B1 | 9/2003 |
| FR | 2828091 | B1 | 11/2003 |
| FR | 2847800 | B1 | 10/2005 |
| FR | 2858543 | B1 | 2/2006 |
| FR | 2828263 | B1 | 5/2007 |
| FR | 2874812 | B1 | 6/2007 |
| FR | 2874813 | B1 | 6/2007 |
| FR | 2883721 | B1 | 6/2007 |
| FR | 2894131 | B1 | 12/2008 |
| FR | 2899096 | B1 | 12/2008 |
| FR | 2910269 | B1 | 2/2009 |
| FR | 2909857 | B1 | 3/2009 |
| FR | 2906454 | B1 | 4/2009 |
| FR | 2906998 | B1 | 4/2009 |
| FR | 2913879 | B1 | 6/2009 |
| FR | 2916959 | B1 | 9/2009 |
| FR | 2892939 | B1 | 1/2010 |
| FR | 2915678 | B1 | 4/2010 |
| FR | 2930137 | B1 | 4/2010 |
| FR | 2915903 | B1 | 6/2010 |
| FR | 2916627 | B1 | 9/2010 |
| FR | 2920664 | B1 | 9/2010 |
| FR | 2932376 | B1 | 4/2011 |

(56) References Cited

FOREIGN PATENT DOCUMENTS

| | | |
|---|---|---|
| FR | 2947716 B1 | 9/2011 |
| FR | 2945440 B1 | 12/2012 |
| FR | 2951549 B1 | 8/2013 |
| FR | 2964855 B1 | 10/2013 |
| FR | 2977792 B1 | 10/2013 |
| FR | 2980968 B1 | 12/2013 |
| FR | 2986149 B1 | 12/2014 |
| FR | 2997288 B1 | 1/2015 |
| FR | 2998167 B1 | 1/2015 |
| FR | 2996747 B1 | 2/2015 |
| FR | 2996748 B1 | 2/2015 |
| FR | 3004638 B1 | 5/2015 |
| FR | 2982763 B1 | 7/2015 |
| FR | 2991162 B1 | 7/2015 |
| FR | 3006582 B1 | 7/2015 |
| FR | 3001121 B1 | 1/2016 |
| FR | 2998166 B1 | 2/2016 |
| FR | 3021862 B1 | 5/2016 |
| FR | 3004917 B1 | 6/2016 |
| FR | 3006884 B1 | 6/2016 |
| FR | 3023704 B1 | 8/2016 |
| FR | 3008885 B1 | 12/2016 |
| FR | 3033494 B1 | 3/2017 |
| FR | 3057154 B1 | 10/2018 |
| FR | 3058631 B1 | 1/2019 |
| FR | 3058632 B1 | 1/2019 |
| FR | 3060292 B1 | 1/2019 |
| FR | 3063631 B1 | 3/2019 |
| FR | 3020265 B1 | 9/2019 |
| FR | 3072013 B1 | 9/2019 |
| GB | 243370 A | 8/1926 |
| GB | 2407146 B | 4/2006 |
| GB | 2398245 B | 3/2007 |
| GB | 2433700 B | 12/2007 |
| GB | 2478498 B | 7/2012 |
| GB | 2530487 B | 12/2016 |
| GB | 2517609 B | 5/2017 |
| GB | 2538749 B | 8/2017 |
| GB | 2538072 B | 11/2017 |
| GB | 2536538 B | 7/2018 |
| GB | 2548891 B | 7/2018 |
| WO | WO-0236048 A1 | 5/2002 |
| WO | WO-2006097931 A2 | 9/2006 |
| WO | WO-2006113906 A1 | 10/2006 |
| WO | WO-2006097931 A3 | 7/2007 |
| WO | WO-2007097983 A2 | 8/2007 |
| WO | WO-2007122459 A2 | 11/2007 |
| WO | WO-2007122459 A3 | 1/2008 |
| WO | WO-2008013915 A2 | 1/2008 |
| WO | WO-2007097983 A3 | 3/2008 |
| WO | WO-2008013915 A3 | 7/2008 |
| WO | WO-2008103722 A2 | 8/2008 |
| WO | WO-2008103722 A3 | 10/2008 |
| WO | WO-2009033469 A1 | 3/2009 |
| WO | WO-2009108615 A1 | 9/2009 |
| WO | WO-2009134701 A2 | 11/2009 |
| WO | WO-2010004546 A1 | 1/2010 |
| WO | WO-2009134701 A3 | 2/2010 |
| WO | WO-2010037141 A1 | 4/2010 |
| WO | WO-2010045297 A2 | 4/2010 |
| WO | WO-2011072084 A2 | 6/2011 |
| WO | WO-2011126758 A1 | 10/2011 |
| WO | WO-2013056898 A1 | 4/2013 |
| WO | WO-2013075215 A1 | 5/2013 |
| WO | WO-2015038875 A1 | 3/2015 |
| WO | WO-2017100927 A1 | 6/2017 |
| WO | WO-2020185597 A1 | 9/2020 |
| WO | WO-2020236931 A1 | 11/2020 |

OTHER PUBLICATIONS

"U.S. Appl. No. 13/096,572, Examiner Interview Summary dated Sep. 6, 2013", 3 pgs.
"U.S. Appl. No. 13/096,572, Non Final Office Action dated Jun. 4, 2013", 11 pgs.
"U.S. Appl. No. 13/096,572, Notice of Allowance dated Sep. 26, 2013", 8 pgs.
"U.S. Appl. No. 13/096,572, Preliminary Amendment filed Sep. 9, 2011", 15 pgs.
"U.S. Appl. No. 13/096,572, Response filed Mar. 25, 2013 to Restriction Requirement dated Mar. 4, 2018", 2 pgs.
"U.S. Appl. No. 13/096,572, Response filed Aug. 30, 2013 to Non Final Office Action dated Jun. 4, 2013", 11 pgs.
"U.S. Appl. No. 13/096,572, Restriction Requirement dated Mar. 4, 2013", 10 pgs.
"U.S. Appl. No. 15/379,748, Corrected Notice of Allowability dated Feb. 10, 2020", 6 pgs.
"U.S. Appl. No. 15/379,748, Corrected Notice of Allowability dated Apr. 1, 2020", 4 pgs.
"U.S. Appl. No. 15/379,748, Non Final Office Action dated Jun. 13, 2019", 18 pgs.
"U.S. Appl. No. 15/379,748, Notice of Allowance dated Dec. 13, 2019", 12 pgs.
"U.S. Appl. No. 15/379,748, Response filed Apr. 3, 2019 to Restriction Requirement dated Oct. 3, 2018", 9 pgs.
"U.S. Appl. No. 15/379,748, Response filed Sep. 25, 2019 to Non-Final Office Action dated Jun. 25, 2019", 12 pgs.
"U.S. Appl. No. 15/379,748, Restriction Requirement dated Oct. 3, 2018", 6 pgs.
"U.S. Appl. No. 16/812,865, Preliminary Amendment filed Sep. 22, 2020", 6 pgs.
"CardiAQ Valve Technologies", Medical Devices Today, [Online], Retrieved from the Internet: <http://www.medicaldevicestoday.com/2009/07/medical-device-start-up-cardiaq-valve-technologies-percutaneous-mitral-valve-replacement.html> Accessed: Mar. 8, 2012, (Jul. 17, 2009), 2 pgs.
"*CardiAQ Valve Technologies* v *NeoVasc*", Case 1:14-cv-12405-NMG. Document 31-main, (Aug. 19, 2014), 3 pgs.
"*CardiAQ Valve Technologies* v *NeoVasc*", Case 1:14-cv-12405-NMG. Document 32-main, (Aug. 19, 2014), 4 pgs.
"*CardiAQ Valve Technologies* v *NeoVasc*", Case 1:14-cv-12405-NMG. Document 34-main, (Aug. 20, 2014), 3 pgs.
"*CardiAQ Valve Technologies* v *NeoVasc*", Case 1:14-cv-12405-NMG. Document 35-main, (Aug. 20, 2014), 6 pgs.
"*CardiAQ Valve Technologies* v *NeoVasc*", Case 1:14-cv-12405-NMG. Document 36-main, (Aug. 20, 2014), 2 pgs.
"*CardiAQ Valve Technologies* v *NeoVasc*", Case 1:14-cv-12405-NMG. Document 38-main, (Aug. 28, 2014), 3 pgs.
"*CardiAQ Valve Technologies* v *NeoVasc*", Case 1:14-cv-12405-NMG. Document 39-main, (Aug. 28, 2014), 28 pgs.
"*CardiAQ Valve Technologies* v *NeoVasc*", Case 1:14-cv-12405-NMG. Document 40-main, (Sep. 11, 2014), 4 pgs.
"*CardiAQ Valve Technologies* v *NeoVasc*", Case 1:14-cv-12405-NMG. Document 41-main, (Sep. 11, 2014), 17 pgs.
"*CardiAQ Valve Technologies* v *NeoVasc*", Case 1:14-cv-12405-NMG. Document 42-main, (Oct. 3, 2014), 6 pgs.
"*CardiAQ Valve Technologies* v *NeoVasc*", Case 1:14-cv-12405-NMG. Document 43-main, (Oct. 7, 2014), 1 pg.
"*CardiAQ Valve Technologies* v *NeoVasc*", Case 1:14-cv-12405-ADB. Document 583, (Oct. 31, 2016), 40 pgs.
"*CardiAQ Valve Technologies* v *NeoVasc*", Case 1:14-cv-12405-NMG. Document 01-1, (Jun. 6, 2014), 1 pg.
"*CardiAQ Valve Technologies* v *NeoVasc*", Case 1:14-cv-12405-NMG. Document 01-2, (Jun. 6, 2014), 1 pg.
"*CardiAQ Valve Technologies* v *NeoVasc*", Case 1:14-cv-12405-NMG. Document 01-main, (Jun. 6, 2014), 20 pgs.
"*CardiAQ Valve Technologies* v *NeoVasc*", Case 1:14-cv-12405-NMG. Document 02-main, (Jun. 6, 2014), 2 pgs.
"*CardiAQ Valve Technologies* v *NeoVasc*", Case 1:14-cv-12405-NMG. Document 03-1, (Jun. 6, 2014), 1 pg.
"*CardiAQ Valve Technologies* v *NeoVasc*", Case 1:14-cv-12405-NMG. Document 03-2, (Jun. 6, 2014), 3 pgs.
"*CardiAQ Valve Technologies* v *NeoVasc*", Case 1:14-cv-12405-NMG. Document 03-3, (Jun. 6, 2014), 1 pg.
"*CardiAQ Valve Technologies* v *NeoVasc*", Case 1:14-cv-12405-NMG. Document 03-4, (Jun. 6, 2014), 1 pg.

(56) References Cited

OTHER PUBLICATIONS

"CardiAQ Valve Technologies v NeoVasc", Case 1:14-cv-12405-NMG. Document 03-5, (Jun. 6, 2014), 2 pgs.
"CardiAQ Valve Technologies v NeoVasc", Case 1:14-cv-12405-NMG. Document 03-main, (Jun. 6, 2014), 20 pgs.
"CardiAQ Valve Technologies v NeoVasc", Case 1:14-cv-12405-NMG. Document 05-main, (Jun. 6, 2014), 2 pgs.
"CardiAQ Valve Technologies v NeoVasc", Case 1:14-cv-12405-NMG. Document 06-main, (Jul. 21, 2014), 3 pgs.
"CardiAQ Valve Technologies v NeoVasc", Case 1:14-cv-12405-NMG. Document 07-main, (Jul. 21, 2014), 3 pgs.
"CardiAQ Valve Technologies v NeoVasc", Case 1:14-cv-12405-NMG. Document 08-1, (Jul. 25, 2014), 3 pgs.
"CardiAQ Valve Technologies v NeoVasc", Case 1:14-cv-12405-NMG. Document 08-main, (Jul. 25, 2014), 2 pgs.
"CardiAQ Valve Technologies v NeoVasc", Case 1:14-cv-12405-NMG. Document 09-1, (Jul. 25, 2014), 3 pgs.
"CardiAQ Valve Technologies v NeoVasc", Case 1:14-cv-12405-NMG. Document 09-main, (Jul. 25, 2014), 2 pgs.
"CardiAQ Valve Technologies v NeoVasc", Case 1:14-cv-12405-NMG. Document 11-1, (Jul. 28, 2014), 3 pgs.
"CardiAQ Valve Technologies v NeoVasc", Case 1:14-cv-12405-NMG. Document 11-main, (Jul. 28, 2014), 2 pgs.
"CardiAQ Valve Technologies v NeoVasc", Case 1:14-cv-12405-NMG. Document 13-1, (Jul. 29, 2014), 3 pgs.
"CardiAQ Valve Technologies v NeoVasc", Case 1:14-cv-12405-NMG. Document 13-2, (Jul. 29, 2014), 1 pg.
"CardiAQ Valve Technologies v NeoVasc", Case 1:14-cv-12405-NMG. Document 13-main, (Jul. 29, 2014), 3 pgs.
"CardiAQ Valve Technologies v NeoVasc", Case 1:14-cv-12405-NMG. Document 14-1, (Jul. 29, 2014), 3 pgs.
"CardiAQ Valve Technologies v NeoVasc", Case 1:14-cv-12405-NMG. Document 14-2, (Jul. 29, 2014), 1 pg.
"CardiAQ Valve Technologies v NeoVasc", Case 1:14-cv-12405-NMG. Document 14-main, (Jul. 29, 2014), 3 pgs.
"CardiAQ Valve Technologies v NeoVasc", Case 1:14-cv-12405-NMG. Document 15-1, (Jul. 29, 2014), 3 pgs.
"CardiAQ Valve Technologies v NeoVasc", Case 1:14-cv-12405-NMG. Document 15-2, (Jul. 29, 2014), 2 pgs.
"CardiAQ Valve Technologies v NeoVasc", Case 1:14-cv-12405-NMG. Document 15-main, (Jul. 29, 2014), 3 pgs.
"CardiAQ Valve Technologies v NeoVasc", Case 1:14-cv-12405-NMG. Document 16-1, (Jul. 29, 2014), 4 pgs.
"CardiAQ Valve Technologies v NeoVasc", Case 1:14-cv-12405-NMG. Document 16-2, (Jul. 29, 2014), 1 pg.
"CardiAQ Valve Technologies v NeoVasc", Case 1:14-cv-12405-NMG. Document 16-main, (Jul. 29, 2014), 3 pgs.
"CardiAQ Valve Technologies v NeoVasc", Case 1:14-cv-12405-NMG. Document 17-1, (Jul. 29, 2014), 3 pg.
"CardiAQ Valve Technologies v NeoVasc", Case 1:14-cv-12405-NMG. Document 17-main, (Jul. 29, 2014), 2 pgs.
"CardiAQ Valve Technologies v NeoVasc", Case 1:14-cv-12405-NMG. Document 18-main, (Jul. 29, 2014), 27 pgs.
"CardiAQ Valve Technologies v NeoVasc", Case 1:14-cv-12405-NMG. Document 19-1, (Jul. 29, 2014), 1 pg.
"CardiAQ Valve Technologies v NeoVasc", Case 1:14-cv-12405-NMG. Document 19-main, (Jul. 29, 2014), 2 pgs.
"CardiAQ Valve Technologies v NeoVasc", Case 1:14-cv-12405-NMG. Document 20-main, (Jul. 29, 2014), 25 pgs.
"CardiAQ Valve Technologies v NeoVasc", Case 1:14-cv-12405-NMG. Document 21-main, (Jul. 29, 2014), 5 pgs.
"CardiAQ Valve Technologies v NeoVasc", Case 1:14-cv-12405-NMG. Document 22-1, (Jul. 29, 2014), 89 pgs.
"CardiAQ Valve Technologies v NeoVasc", Case 1:14-cv-12405-NMG. Document 22-main, (Jul. 29, 2014), 4 pgs.
"CardiAQ Valve Technologies v NeoVasc", Case 1:14-cv-12405-NMG. Document 24-1, (Aug. 12, 2014), 17 pgs.
"CardiAQ Valve Technologies v NeoVasc", Case 1:14-cv-12405-NMG. Document 24-2, (Aug. 12, 2014), 4 pgs.
"CardiAQ Valve Technologies v NeoVasc", Case 1:14-cv-12405-NMG. Document 24-3, (Aug. 12, 2014), 2 pgs.
"CardiAQ Valve Technologies v NeoVasc", Case 1:14-cv-12405-NMG. Document 24-4, (Aug. 12, 2014), 2 pgs.
"CardiAQ Valve Technologies v NeoVasc", Case 1:14-cv-12405-NMG. Document 24-5, (Aug. 12, 2014), 3 pgs.
"CardiAQ Valve Technologies v NeoVasc", Case 1:14-cv-12405-NMG. Document 24-main, (Aug. 12, 2014), 21 pgs.
"CardiAQ Valve Technologies v NeoVasc", Case 1:14-cv-12405-NMG. Document 25-main, (Aug. 12, 2014), 15 pgs.
"CardiAQ Valve Technologies v NeoVasc", Case 1:14-cv-12405-NMG. Document 26-main, (Aug. 12, 2014), 4 pgs.
"CardiAQ Valve Technologies v NeoVasc", Case 1:14-cv-12405-NMG. Document 27-1, (Aug. 12, 2014), 28 pgs.
"CardiAQ Valve Technologies v NeoVasc", Case 1:14-cv-12405-NMG. Document 27-2, (Aug. 12, 2014), 51 pgs.
"CardiAQ Valve Technologies v NeoVasc", Case 1:14-cv-12405-NMG. Document 27-3, (Aug. 12, 2014), 3 pgs.
"CardiAQ Valve Technologies v NeoVasc", Case 1:14-cv-12405-NMG. Document 27-main, (Aug. 12, 2014), 4 pgs.
"CardiAQ Valve Technologies v NeoVasc", Case 1:14-cv-12405-NMG. Document 28-main, (Aug. 12, 2014), 16 pgs.
"CardiAQ Valve Technologies v NeoVasc", Case 1:14-cv-12405-NMG. Document 29-main, (Aug. 13, 2014), 2 pgs.
"CardiAQ Valve Technologies v NeoVasc", Case 1:14-cv-12405-NMG. Document 30-main, (Aug. 19, 2014), 2 pgs.
"CardiAQ Valve Technologies v NeoVasc", Case 1:14-cv-12405-NMG. Document 31-1, (Aug. 19, 2014), 6 pgs.
"CardiAQ Valve Technologies v NeoVasc", Case 1:14-cv-12405-NMG. Document 31-2, (Aug. 19, 2014), 2 pgs.
"CardiAQ Valve Technologies: Percutaneous Mitral Valve Replacement", Start Up Windhover Review of Emerging Medical Ventures, vol. 14. No. 6, (Jun. 2009), 48-49.
"Chinese Application Serial No. 201680081812.0, Office Action dated Oct. 31, 2019", w/English Translation, 22 pgs.
"Chinese Application Serial No. 201680081812.0, Response filed Mar. 11, 2020 to Office Action dated Oct. 31, 2019", w/English Claims, 18 pgs.
"Chinese Application Serial No. 2016800818120, Office Action dated Jun. 29, 2020", with English translation of claims, 14 pgs.
"Chinese Application Serial No. 2016800818120, Response filed Sep. 8, 2020 to Office Action dated Jun. 29, 2020", w/ English Claims, 12 pgs.
"European Application Serial No. 11777065.1, Extended European Search Report dated Dec. 10, 2013", 6 pgs.
"European Application Serial No. 16874205.4, Communication Pursuant to Article 94(3) EPC dated Mar. 2, 2020", 5 pgs.
"European Application Serial No. 168/4205,4, Extended European Search Report dated Jul. 5, 2019", 9 pgs.
"European Application Serial No. 16874205.4, Response filed Feb. 3, 2020 to Extended European Search Report dated Jul. 5, 2019", 17 pgs.
"European Application Serial No. 16874205.4, Response filed Jul. 13, 2020 to Communication Pursuant to Article 94(3) EPC dated Mar. 2, 2020", 89 pgs.
"International Application Serial No. PCT/CA2011/000662, International Search Report dated Sep. 27, 2011", 5 pgs.
"International Application Serial No. PCT/CA2011/000662, Written Opinion dated Sep. 27, 2011", 6 pgs.
"International Application Serial No. PCT/CA2016/051482, International Preliminary Report on Patentability dated Jun. 28, 2018", 10 pgs.
"International Application Serial No. PCT/CA2016/051482, International Search Report dated Feb. 27, 2017", 8 pgs.
"International Application Serial No. PCT/CA2016/051482, Written Opinion dated Feb. 27, 2017", 8 pgs.
"International Application Serial No. PCT/US2020/021493, International Search Report dated Jul. 6, 2020", 4 pgs.
"International Application Serial No. PCT/US2020/021493, Invitation to Pay Additional Fees dated May 14, 2020", 2 pgs.
"International Application Serial No. PCT/US2020/021493, Written Opinion dated Jul. 6, 2020", 6 pgs.

(56) References Cited

OTHER PUBLICATIONS

"International Application Serial No. PCT/US2020/033798, International Search Report dated Aug. 26, 2020", 2 pgs.

"International Application Serial No. PCT/US2020/033798, Written Opinion dated Aug. 26, 2020", 7 pgs.

Bavaria, "CardiAQ Valve Technologies (CVT) discloses successful results of acute in vivo study of its novel transcatheter mitral valve implantation (TMVI) system", [Online], Retrieved from the Internet: <http://eon.businesswire.com/news/eon/20090928005120/en/CardiAQ-Valve-Technologies/Heart/heart-failure>, (Sep. 28, 2009), 2 pgs.

Bavaria, "CardiAQ Valve Technologies. TCT Company Overview", Transcatheter Cardiovascular Therapeutics Conference. San Francisco, CA, (Sep. 21-25, 2009), 11 pgs.

Carpentier-Edwards, "Why compromise in the mitral position?", Edwards Lifesciences, (2004), 4 pgs.

Fitzgerald, "Tomorrow's technology: percutaneous mitral valve replacement, chordal shortening and beyond", Transcatheter Valve Therapies (TVT) Conference. Seattle, WA, (Jun. 7, 2010), 8 pgs.

Mack, "Advantages and limitations of surgical mitral valve replacement; lessons for the transcatheter approach", Texas Cardiovascular Innovative Ventures (TCIV) Conference. Dallas, TX, (Jun. 7, 2010), 32 pgs.

Ostrovsky, "Transcatheter mitral valve implantation technology from CardiAQ", [Online], Retrieved from the Internet: <http://medgadget.com/2010/01/transcatheter__mitral_valveimplantation__technologyfrom__cardiaq.html>, Accessed Jun. 27, 2012 from, (Jan. 15, 2010), 2 pgs.

Ratz, "CardiAQ Valve Technologies. Innovations in heartvalve therapy", IN3 San Francisco PowerPoint presentation in 19 slides, (Jun. 18, 2008), 19 pgs.

Ruiz, "Overview of novel transcatheter valve technologies", Glimpse into the future. New transcatheter mitral valve treatment. Euro PCR. Paris, France, (May 27, 2010), 14 pgs.

"International Application Serial No. PCT/US2020/033798, International Preliminary Report on Patentability dated Dec. 2, 2021", 9 pgs.

"Australian Application Serial No. 2020279750, First Examination Report dated Aug. 26, 2022", 3 pgs.

"European Application Serial No. 20809875.6 Response filed Jul. 4, 2022 to Communication pursuant to Rules 161(2) and 162 EPC dated Jan. 5, 2022", 12 pgs.

"Canadian Application Serial No. 3,140,925, Examiners Rule 86(2) Requisition dated Jan. 13, 2023", 4 pgs.

"Chinese Application Serial No. 202080047634.6, Office Action dated May 18, 2023", w English translation, 17 pgs.

"European Application Serial No. 20809875.6, Extended European Search Report dated May 8, 2023", 5 pgs.

"Australian Application Serial No. 2020279750, Response filed Jun. 21, 2023 to First Examination Report dated Aug. 26, 2022", 23 pgs.

\* cited by examiner

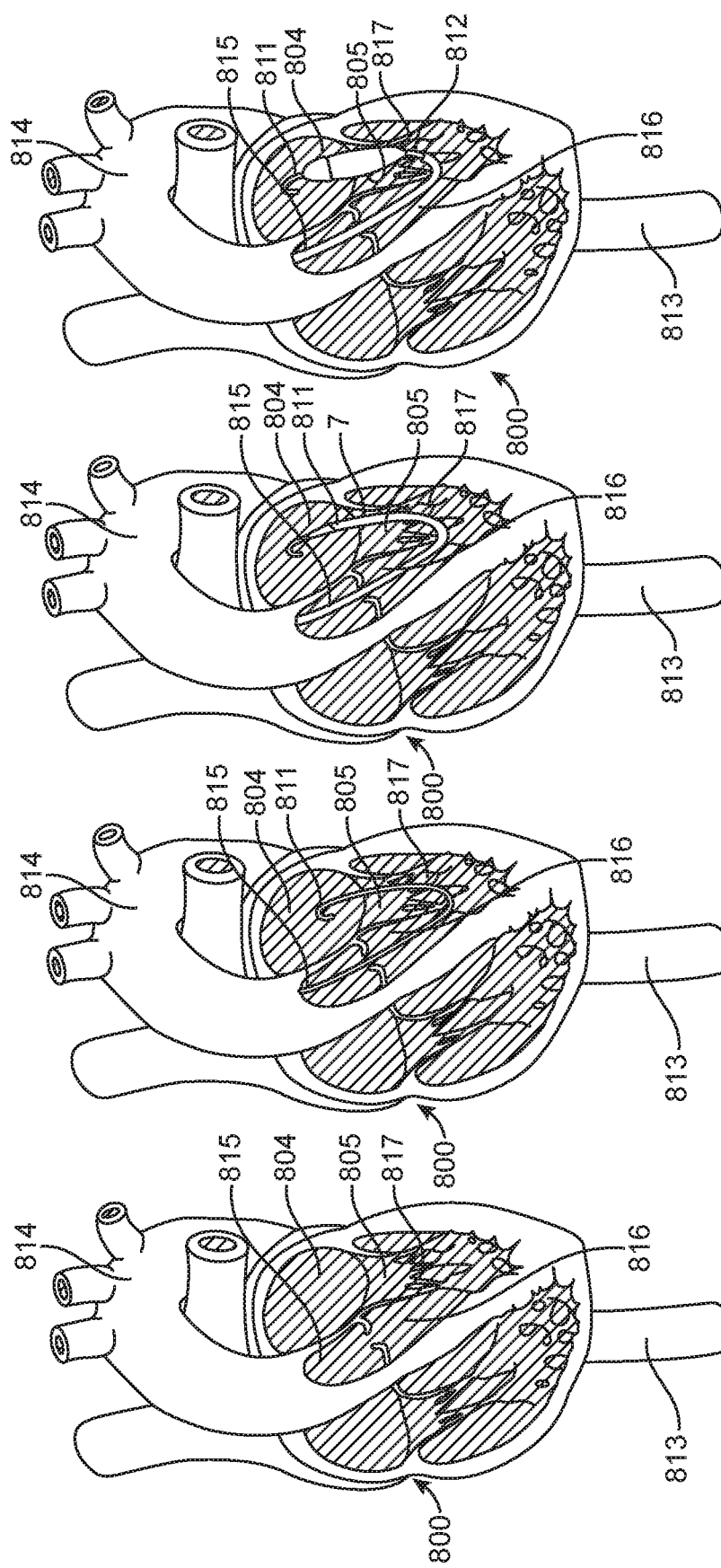

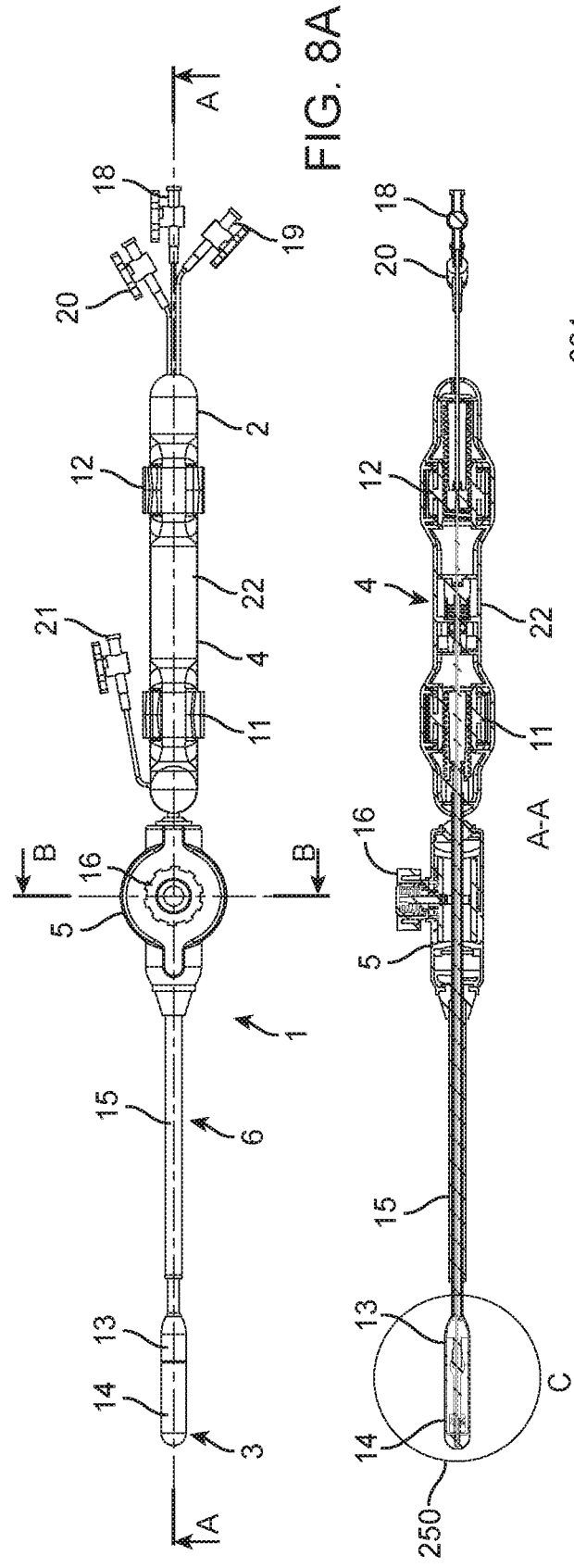
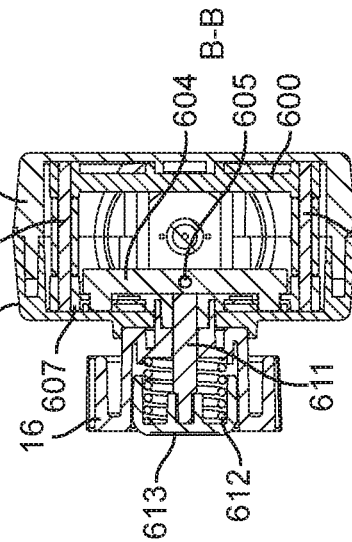
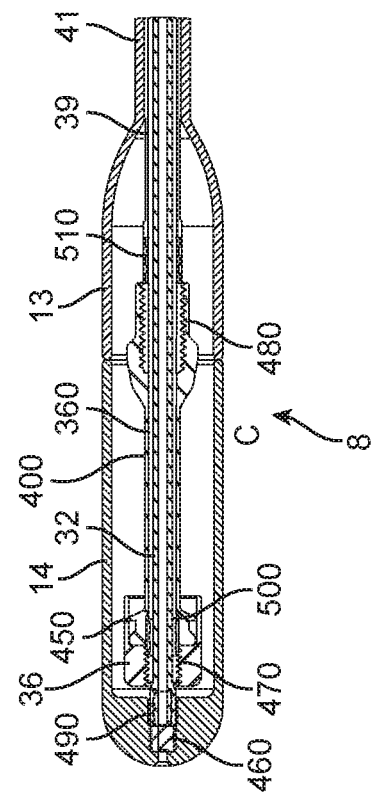
FIG. 8A
FIG. 8B
FIG. 8C
FIG. 8D

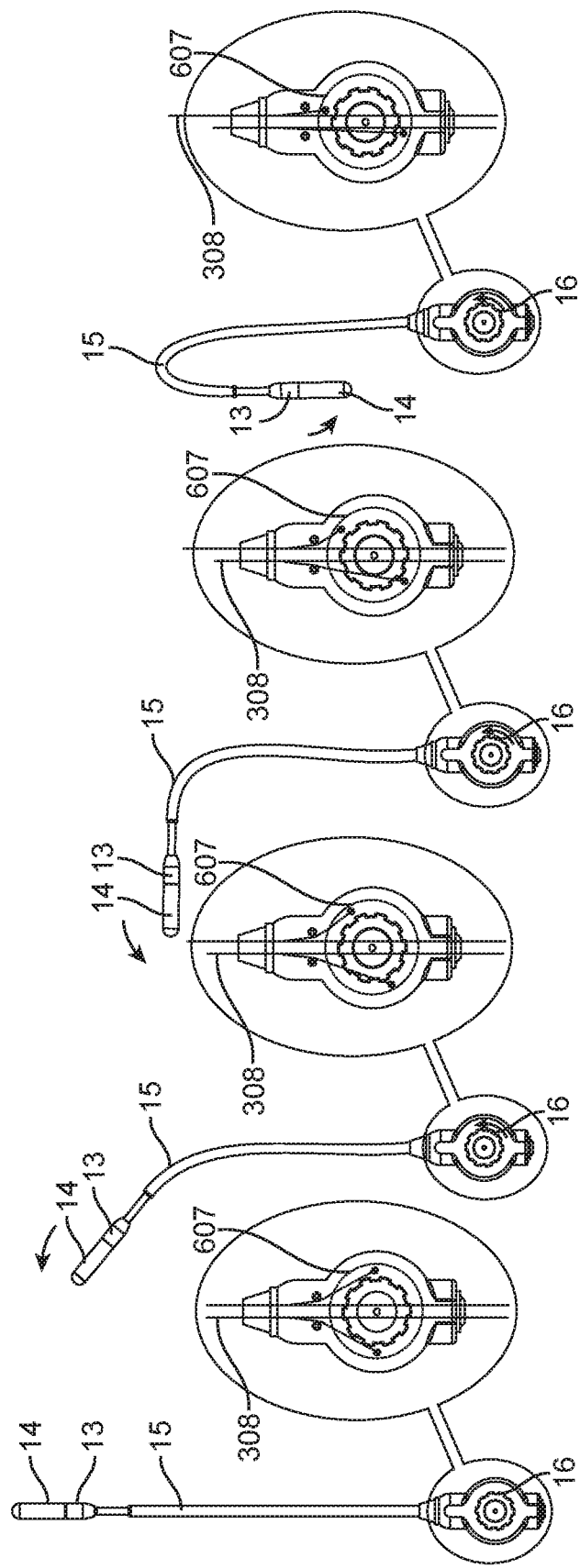

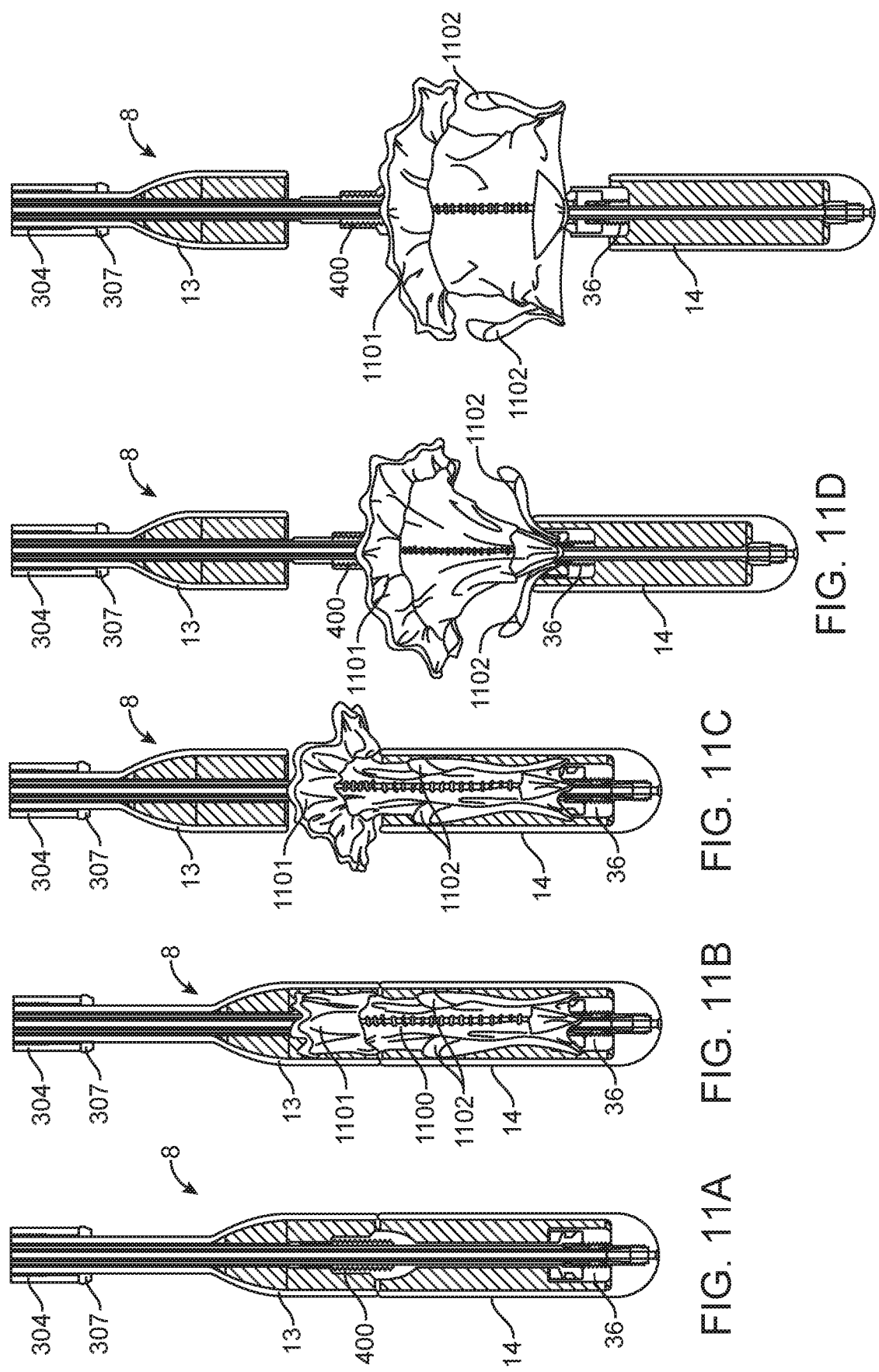

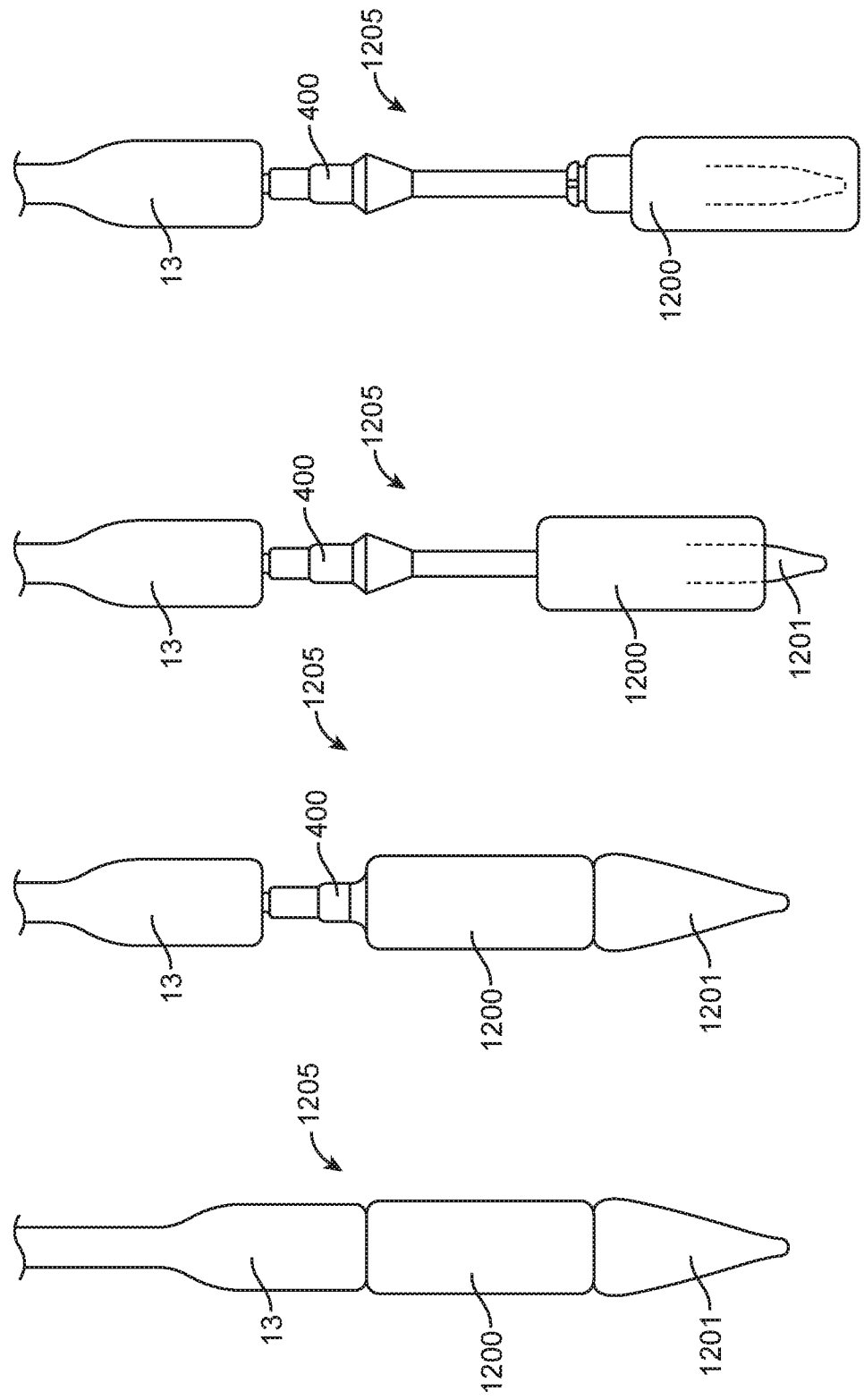

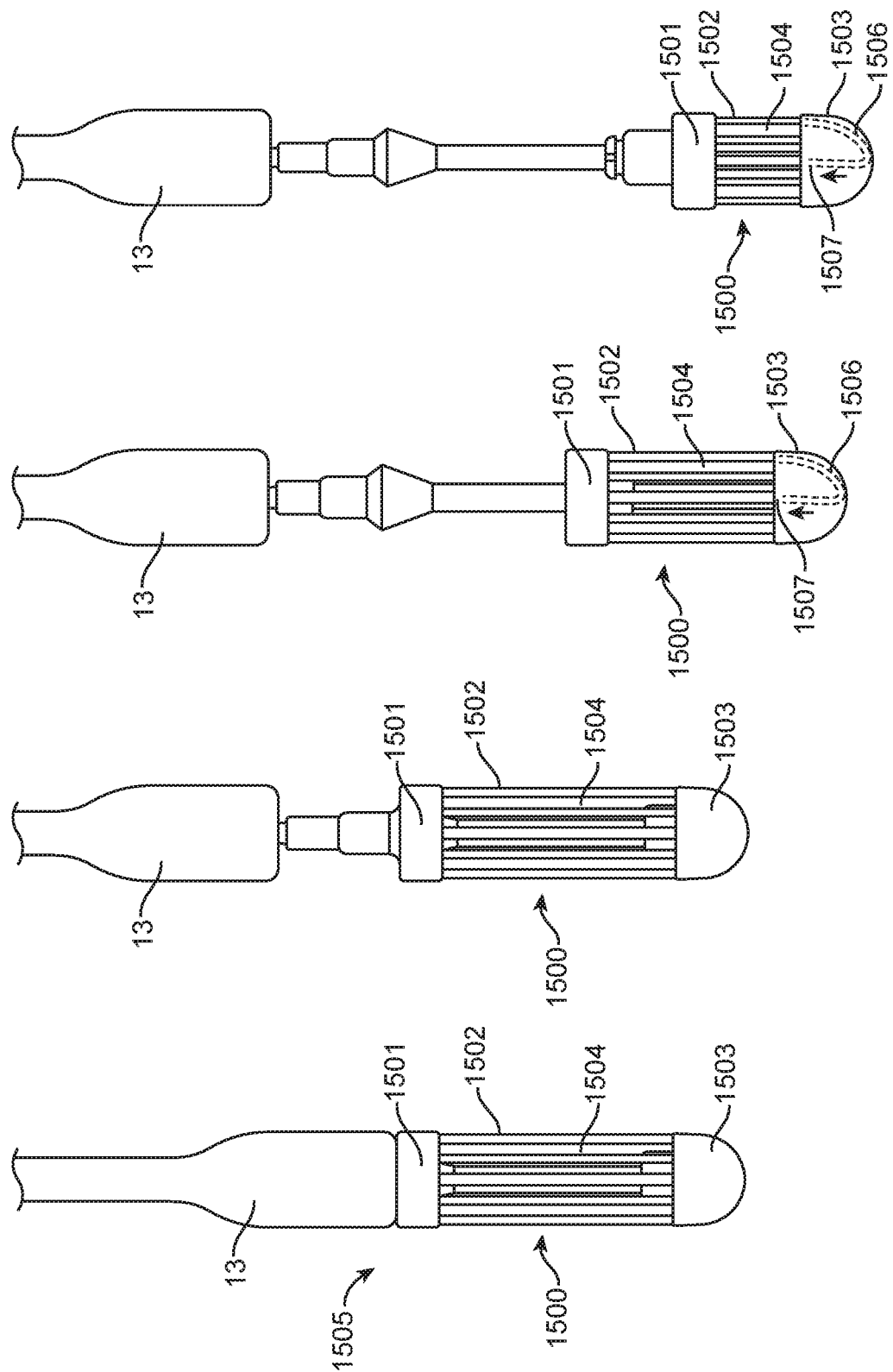

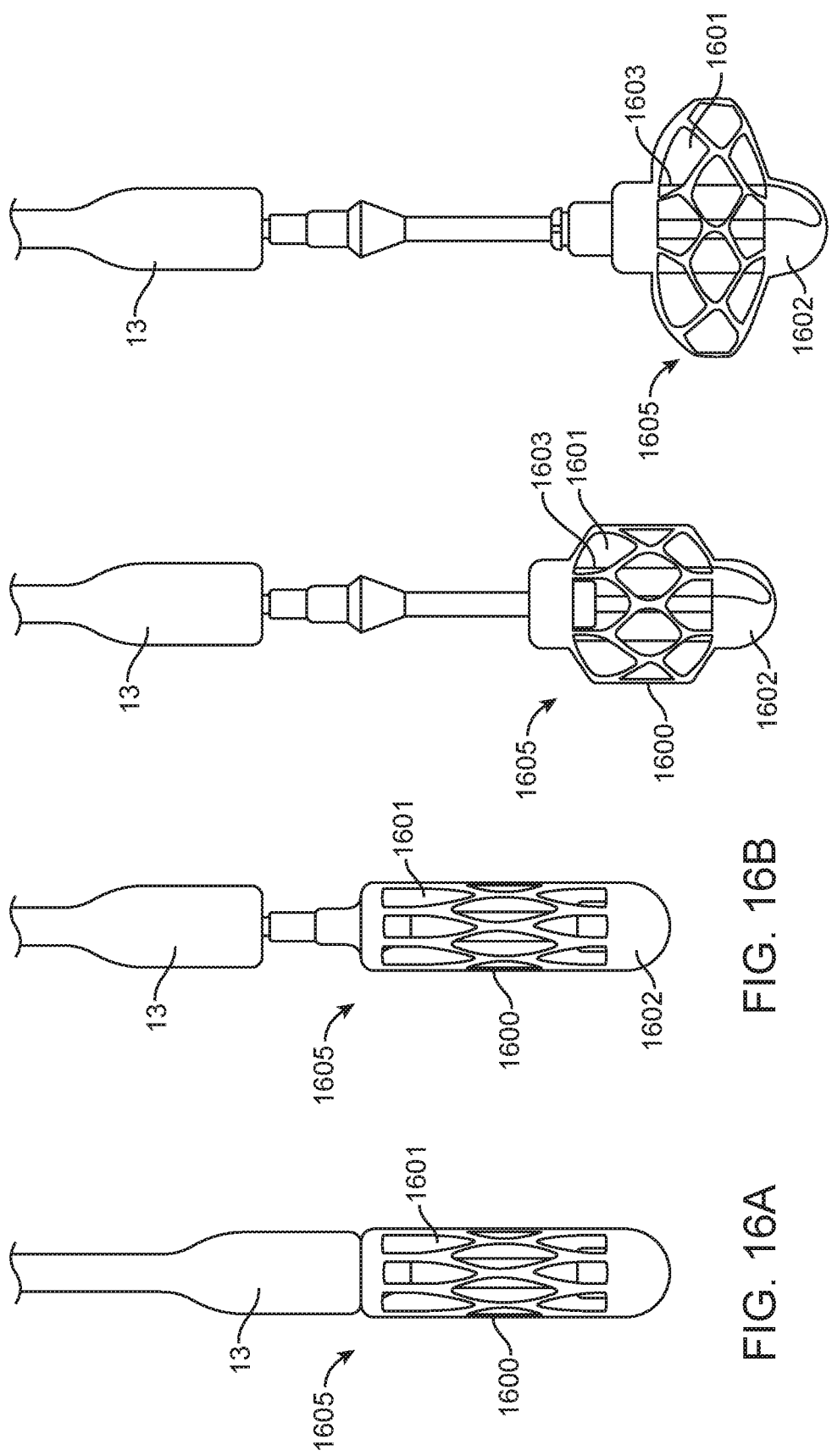

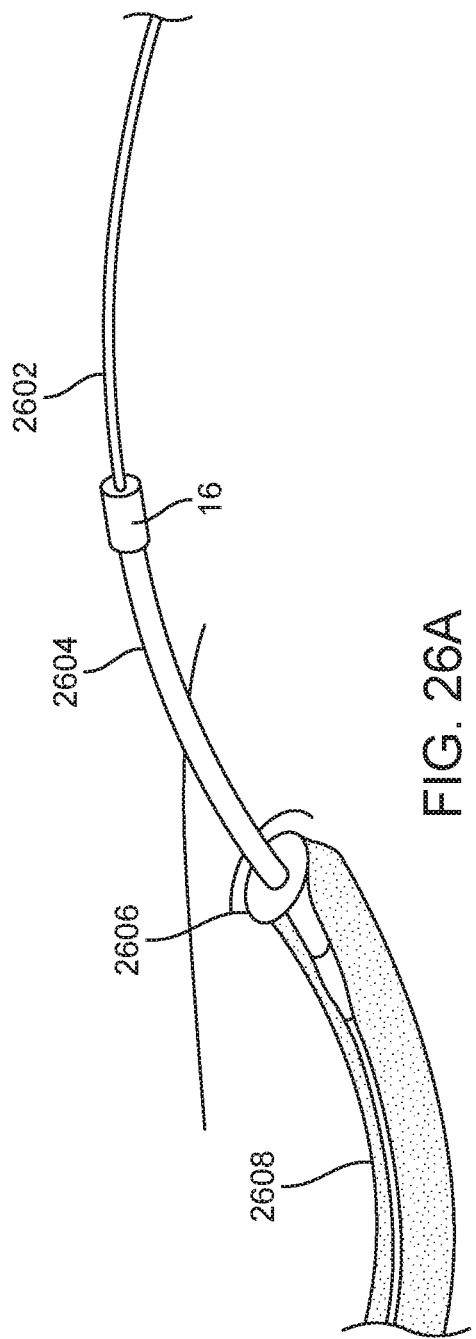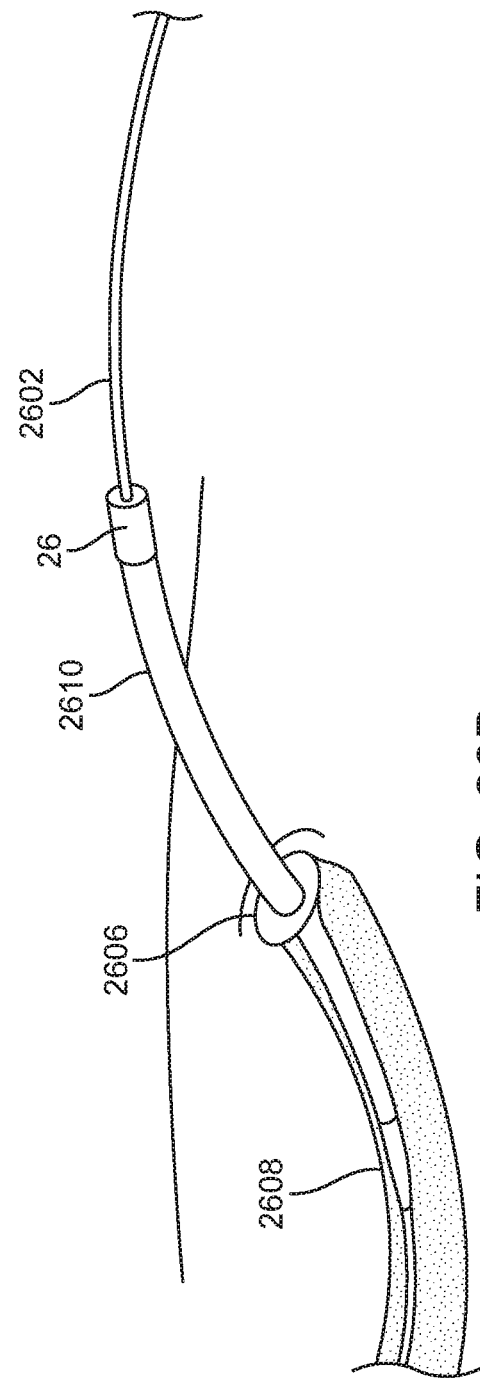

INTRODUCER WITH HEMOSTASIS MECHANISM

CLAIM OF PRIORITY

The present application is a non-provisional of, and claims the benefit of U.S. Provisional Patent Application No. 62/850,179 filed on May 20, 2019; the entire contents of which are incorporated herein by reference.

CROSS-REFERENCE TO RELATED PATENT DOCUMENTS

The present application is related to U.S. patent application Ser. No. 16/812,865 filed Mar. 9, 2020; the entire contents of which are incorporated herein by reference.

BACKGROUND

Less invasive vascular procedures typically involve the use of an introducer sheath which provides access to a vessel such as a vein or artery so that a catheter or other instrument may be easily inserted into the vessel and advanced to a target treatment location.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIGS. 3A-3D are sequential views of the procedural pathway traversed by the prosthesis during a transaortic implantation procedure.

FIG. 8A is a side view of the delivery system in FIG. 1.

FIG. 8B is a cross-sectional view of the delivery system taken along line A-A in FIG. 8A.

FIGS. 8C-8D show other cross-sections of the delivery system.

FIGS. 10A-10D are sequential views of the steering handle portion of the delivery system of FIG. 1.

FIGS. 11A-11E are sequential cross-sectional views of the valve capsule portion taken along the line A-A in FIG. 8A.

FIGS. 12A-12D are sequential partial views of an alternative example of the valve capsule portion of the delivery system of FIG. 1.

FIGS. 15A-15D are sequential partial views of an alternative example of the valve capsule portion of the delivery system of FIG. 1.

FIGS. 16A-16D are sequential partial views of an alternative example of the valve capsule portion of the delivery system of FIG. 1.

FIGS. 26A-26D illustrate an example of a method for inserting an introducer sheath into a patient.

DETAILED DESCRIPTION

Less invasive vascular procedures typically involve the use of an introducer sheath which provides access to a vessel such as a vein or artery so that a catheter or other instrument may be easily inserted into the vessel and advanced to a target treatment location. While many commercially available introducer sheaths perform well, in some circumstances the introducer sheaths may leak blood, may be complex to operate, or may have a profile (e.g. diameter) that is larger than desired. It would therefore be desirable to provide improved introducer sheaths that overcome at least some of these challenges.

Specific examples of the disclosed device, delivery system, and method will now be described with reference to the drawings. Nothing in this detailed description is intended to imply that any particular component, feature, or step is essential to the invention.

Delivery System

Figure 1:
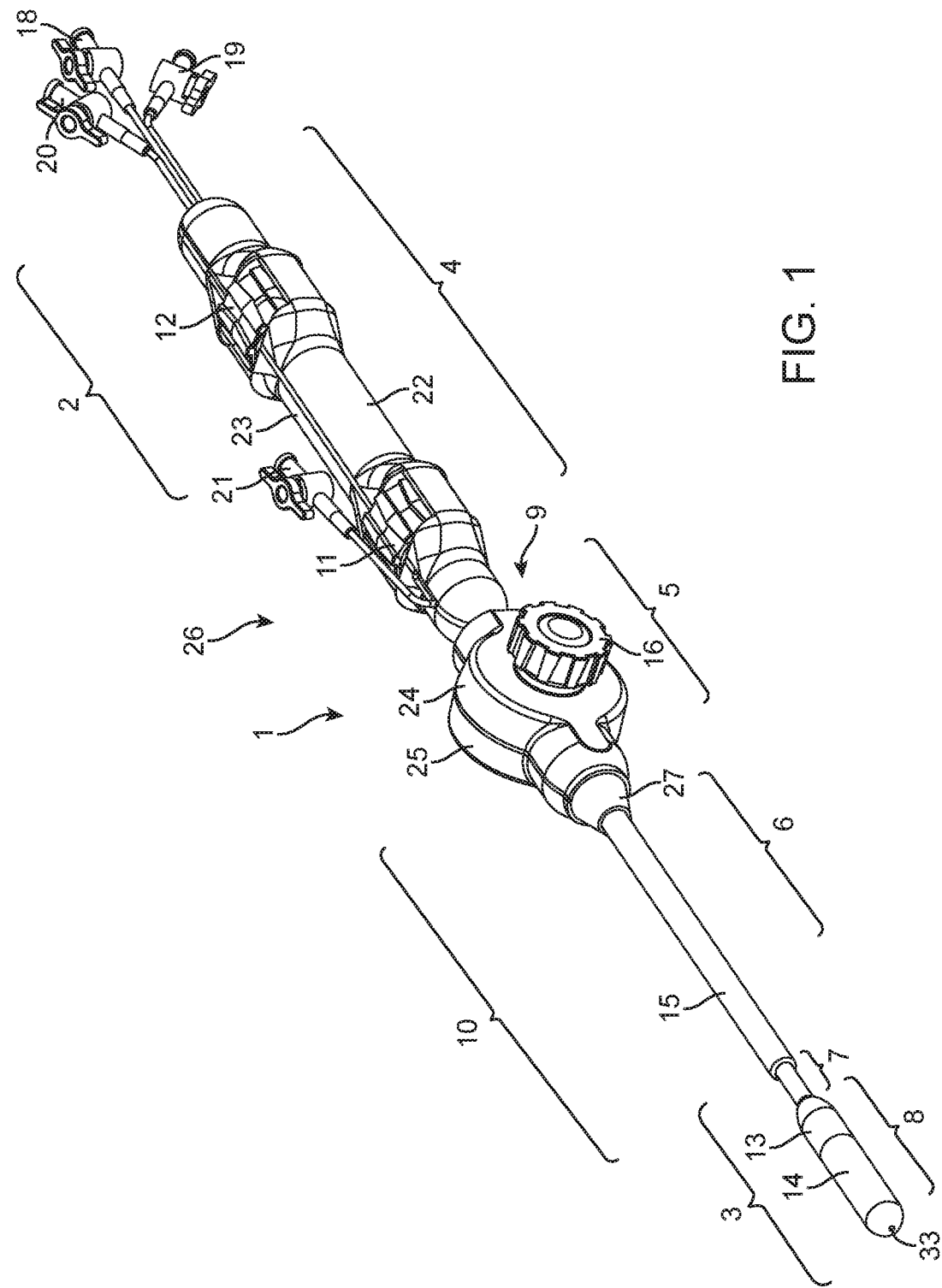
FIG. 1 is a perspective view of a trans-septal delivery system for a prosthetic heart valve.

Referring initially to FIG. 1, one example of a transseptal delivery system for transcatheter heart valve delivery is depicted generally as 1. In the drawings and in the description, which follows, the term "proximal" will refer to the end 2 of the delivery system that is closest to the user, while the term "distal" will refer to the end 3 that is farthest from the user. The transseptal delivery system 1 can comprise a prosthesis such as a prosthesis capsule or valve capsule assembly 8, a delivery catheter assembly 7, a steering guide 10, a delivery handle assembly 4, and an interface 9 between the delivery handle 4 and steering handle 5. The steering guide 10 can be comprised of a steerable catheter assembly 6 and a steering handle 5. The valve capsule assembly 8 can be in operable communication with the delivery handle assembly 4 by way of the delivery catheter assembly 7 which extends therebetween. The translational position and angular attitude of the prosthesis or valve capsule assembly 8 can be operably controlled by the steering handle 5 and in communication by way of the steerable catheter assembly 6 which extends therebetween. The interface 9 can be comprised of a slidable seal, such as an O-ring type seal. The interface 9 can further function to allow the delivery handle or delivery catheter to translate within the steering handle while maintaining some stiction, thus preventing blood or other fluid from seeping out of the steering handle should such blood or fluid make its way up the steering catheter assembly.

Further details of a transcatheter mitral valve or any prosthesis that may be used with any of the delivery devices described herein, along with other related delivery catheters are described in U.S. Pat. No. 8,579,964 to Lane et. al., the entire contents of which are incorporated by reference herein.

Generally, delivery handle assembly 4 includes a distal actuator such as a thumbwheel 11 and a proximal actuator such as a thumbwheel 12, both of which are integrally associated with the delivery handle assembly 4, which is comprised of an A-side delivery handle housing 22, and a B-side delivery handle housing 23. Distal thumbwheel 11 and proximal thumbwheel 12 are also rotatably positionable with respect to the delivery handle assembly 4, serving as actuators by way of internal threads (not shown) and enabling translational control of various catheters within the delivery catheter assembly 7, further evidence of which will be detailed in a later section. The delivery handle assembly 4 is operatively coupled to the valve capsule assembly 8 via the delivery catheter assembly 7, which functions in one aspect as a motion translation agent. In some examples, the delivery handle assembly 4, delivery catheter assembly 7 and valve capsule assembly 8 can form a delivery system 26. In some examples, the steering handle 5 and steerable catheter assembly 7 can form a steering guide 10, which provides a path through which the delivery system 26 can translate and rotate, and from which it may take its shape in order to traverse tortuous vasculature during implantation. Taken altogether, the delivery system 26 and steering guide 10 can form the transseptal delivery system 1.

Figure 17A:
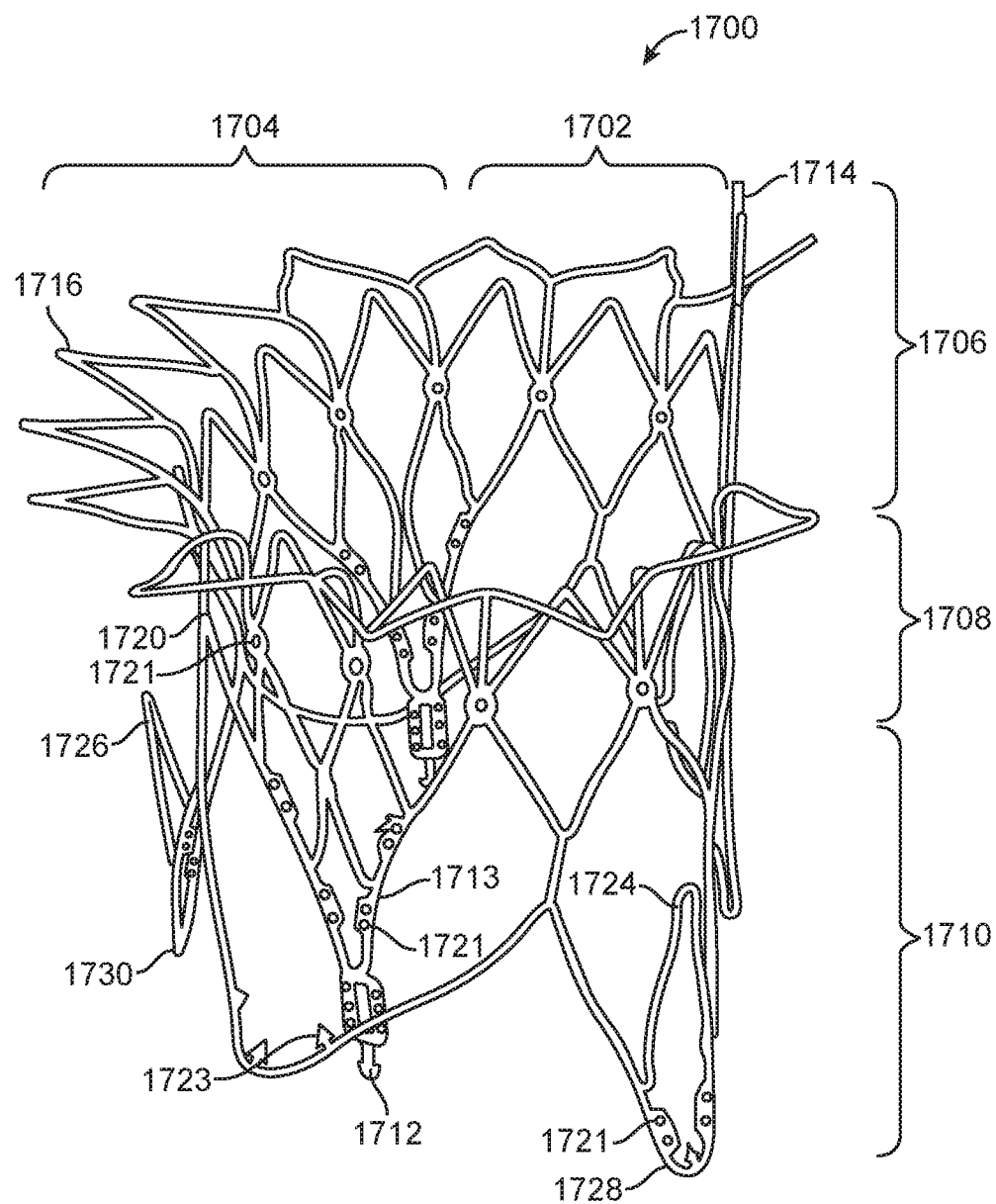
FIG. 17A is a perspective view of a prosthetic mitral valve.
Figure 17B:
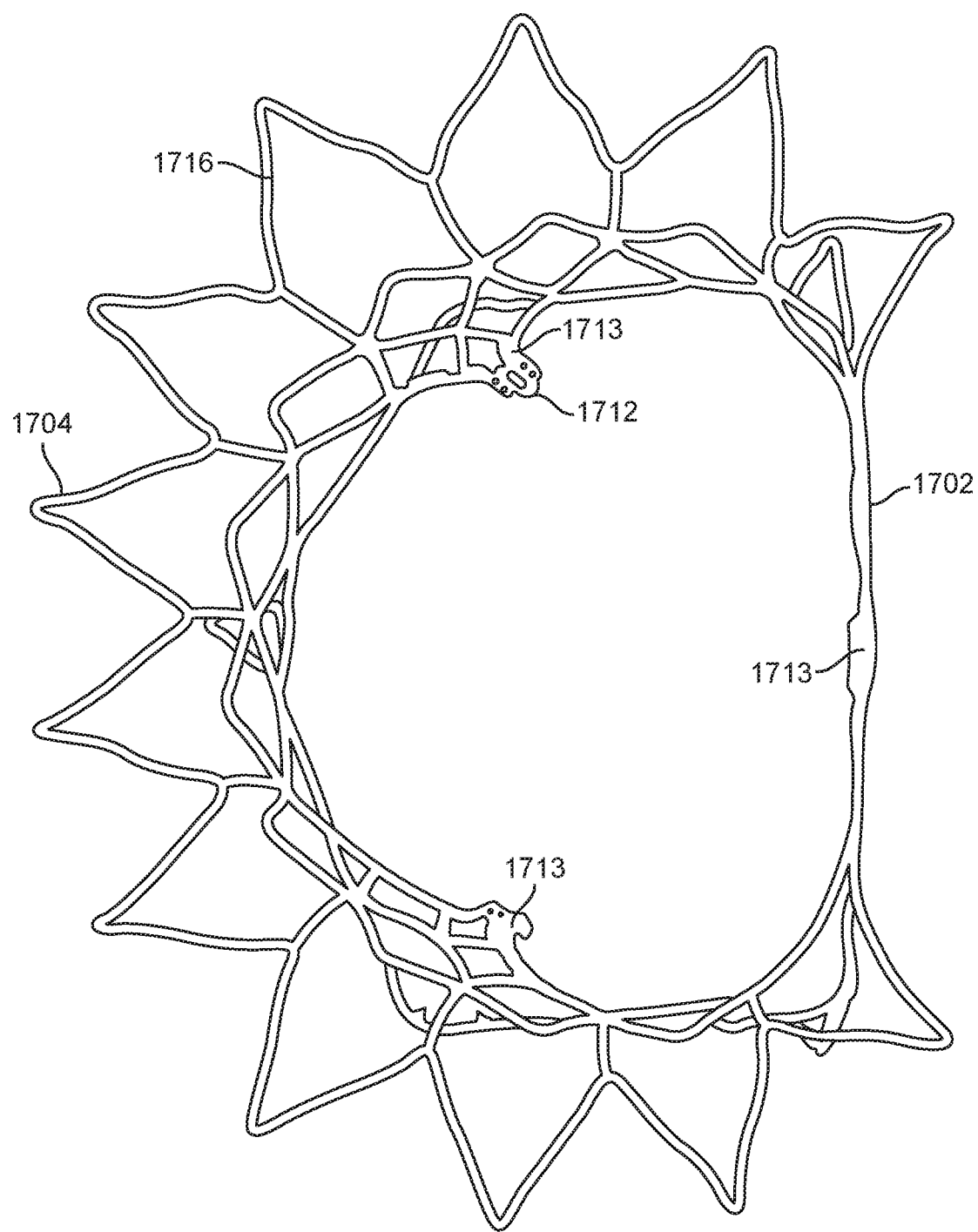
FIG. 17B is a top view of the prosthetic valve in FIG. 17A.
Figure 18A:
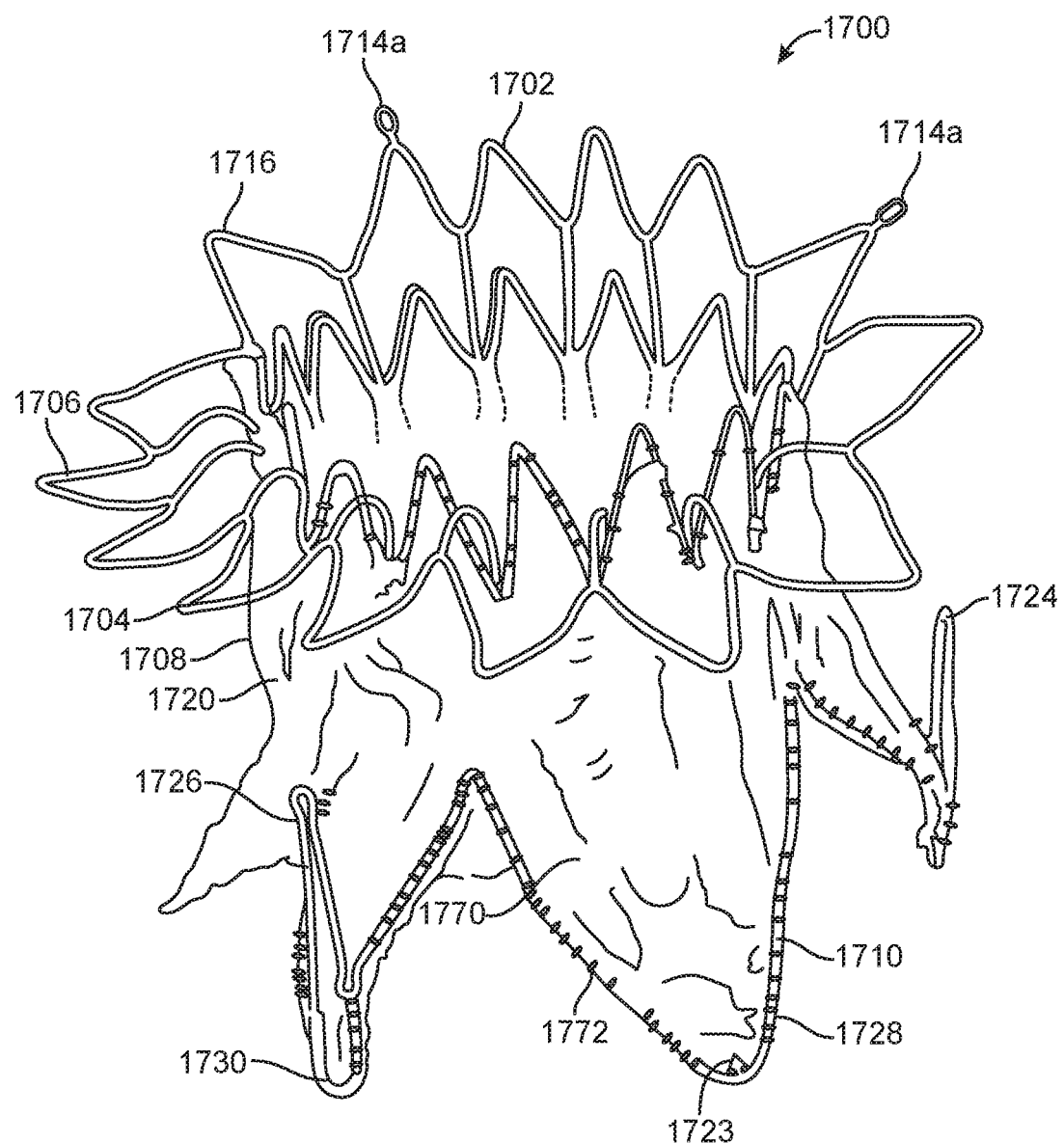
FIG. 18A illustrates a perspective view of the prosthetic valve in FIG. 17A.

Valve capsule assembly 8 may exhibit various constructions. For example, the distal capsule 14 and proximal capsule 13 may be formed from substantially rigid, stainless steel, polymer, metal or otherwise rigid tubing, from collapsible, flexible tubing, or from shape-settable exotic metal alloys which exhibit shape memory characteristics and are actuated by temperature gradients inherent to the human physiology, such as nitinol. Presently, portions of the valve capsule assembly 8 can be translatably controlled by the turning of either the distal thumbwheel 11, or the proximal thumbwheel 12, located in the delivery handle assembly 4. By rotating the distal thumbwheel 11, the proximal capsule 14 can be translatably positioned along the axis of the capsule assembly 8 in order to reveal certain portions of the prosthesis such as a prosthetic mitral valve for example, as shown in FIGS. 17A-17B and 18A-A8B, that is entrained within. By rotating the proximal thumbwheel 12, the proximal capsule 13 can be translatably positioned along the axis of the valve capsule assembly 8, revealing and releasing certain portions of the prosthetic valve (not shown). Capsule variations will be described in detail in a later section.

Figure 7:
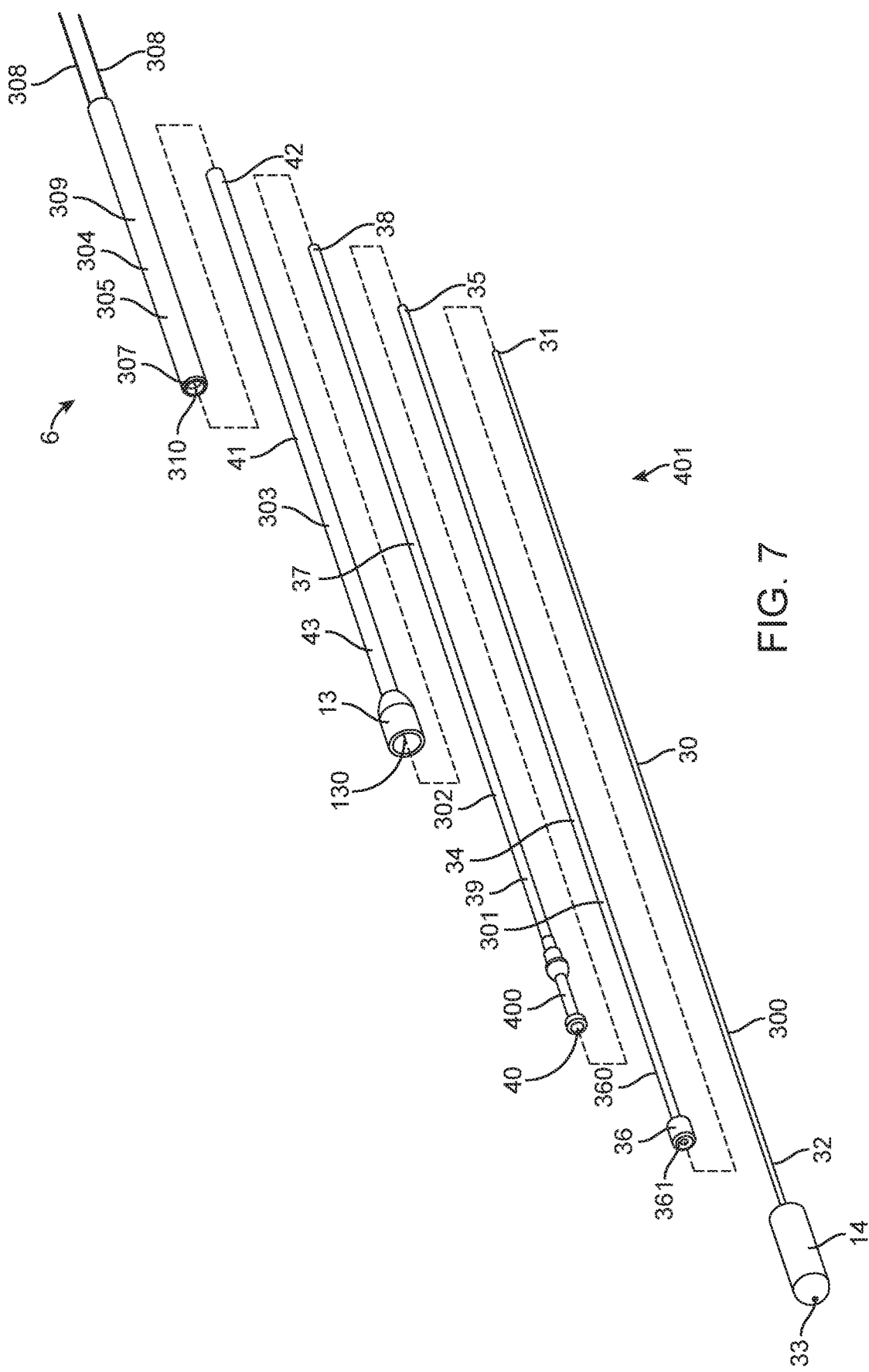
FIG. 7 is an assembly view of the delivery catheter portion of the delivery system seen in FIG. 1.

With reference to FIG. 7, the delivery catheter assembly 7 is generally comprised of a family of nested catheters concentrically and slidably disposed over one another. The innermost catheter in the family of nested catheters is the guidewire catheter 30 which has a distal section 32 that is coupled to the distal capsule 14, and a proximal section 31, with a guidewire lumen 33 that is generally sized to accept a guidewire running therebetween. The guidewire catheter 30 has a constant outer diameter and a constant inner diameter throughout its entire length, as well as a flexible section 300 which allows for articulation. The guidewire catheter 30 is generally configured to be able to fit inside of and translate slidably with respect to the bell catheter 34. The bell catheter 34 has a distal section 360 that is coupled to a bell 36, wherein the bell can be generally cylindrically shaped having a diameter larger than the bell catheter, and a proximal section 35, with an inner lumen 361 that is generally sized to accept the guidewire catheter 30 running therebetween. The bell catheter 34 has a constant outer diameter and a constant inner diameter throughout its entire length, as well as a flexible section 301 which allows for articulation. The bell catheter 34 is generally configured to be able to fit inside of and slidably translate with respect to the anchoring catheter 37. The anchoring catheter 37 has a distal section 39 that is coupled to an anchor 400, wherein the anchor can be generally cylindrically shaped and have a plurality of anchoring slots circumferentially positioned to receive valve commissure anchoring portions (not shown), and a proximal section 38, with an inner lumen 40 that is generally sized to accept the bell catheter 34 running therebetween. The anchoring catheter 37 has a constant outer diameter and a constant inner diameter throughout its entire length, as well as a flexible section 302 which allows for articulation. The anchoring catheter 37 is generally configured to be able to fit inside of and translate with respect to the sheath catheter 41. The sheath catheter 41 has a distal section 43 that is coupled to the proximal capsule 13, wherein the proximal capsule can have a cylindrical portion terminating in a cap portion, and wherein the cap portion can have a rounded dome-like surface, and a proximal section 42, with an inner lumen 130 that is generally sized to accept the anchoring catheter 37 running therebetween. The sheath catheter 41 has a constant outer diameter and a constant inner diameter throughout its entire length, as well as a flexible section 303 which allows for articulation. The sheath catheter 41 is generally configured to be able to fit inside of and slidably translate with respect to the steering catheter assembly 6. The steering catheter assembly 6 is comprised of a steerable catheter 309, a pull ring 307, wherein the pull ring can have a circular ring-like shape located at the distal section 305 of the catheter, a plurality of pull wires 308 located at the proximal section of the catheter, a flexible section 304 that allows for articulation, and an inner lumen 310 running throughout the entire length. For each pull wire 308 there is a corresponding lumen (not shown) that runs the entirety of the steerable catheter 309.

Generally, the steering guide 10 includes an interface section 9 that is comprised of an O-ring type interface of cylindrical shape similar to a gasket, which is embedded within A and B side steering handle housings 24 and 25 respectively, the A-side steering handle housing 24, the B-side steering handle housing 25, an actuator such as a steering thumbwheel 16, wherein the steering thumbwheel can have a generally cylindrical shape, a catheter strain relief 27, and a steerable catheter assembly 6. The steering thumbwheel can additionally include one or more protrusions separated by one or more recesses or slots to provide a surface to facilitate grasping and turning the wheel. In some examples, the steering thumbwheel can have a textured surface with ribs to facilitate grasping and turning the wheel. The interface section 9 provides a dynamic seal between the steering handle 5 and the delivery catheter assembly 7 thus allowing for slidably sealed catheter translation thereby; the delivery catheter assembly thus may traverse therethrough and exit towards the distal end of the steering guide 10 at the terminal, articulated end 15 of the steerable catheter assembly 6. While the interface section 9 provides a dynamic seal, the delivery catheter assembly 7 may still translate and rotate within the steering guide 10, in order to define accurate positioning within a patient, at the target implant site. Detail regarding the implant procedure and target implant site will be discussed in a later section. In order to actuate the steerable portion of the steering catheter assembly 6, the steering thumbwheel 16 must be turned. When the steering thumbwheel 16 is turned, the articulated end 15 of the steerable catheter assembly 6 will bend in the same direction as the direction of thumbwheel turning. This motion translation is achieved through the use of internal pull wires 308, as depicted for example in FIG. 7, that are distally in mated connection (such as a welded connection, or using fasteners, or adhesives, or any suitable method of fastening) with a pull ring 307, and proximally connectably communicate with the internal mechanisms which are inherent to the steering handle 5 and will be described in further detail in a later section.

Figures 2A, 2B, 2C:
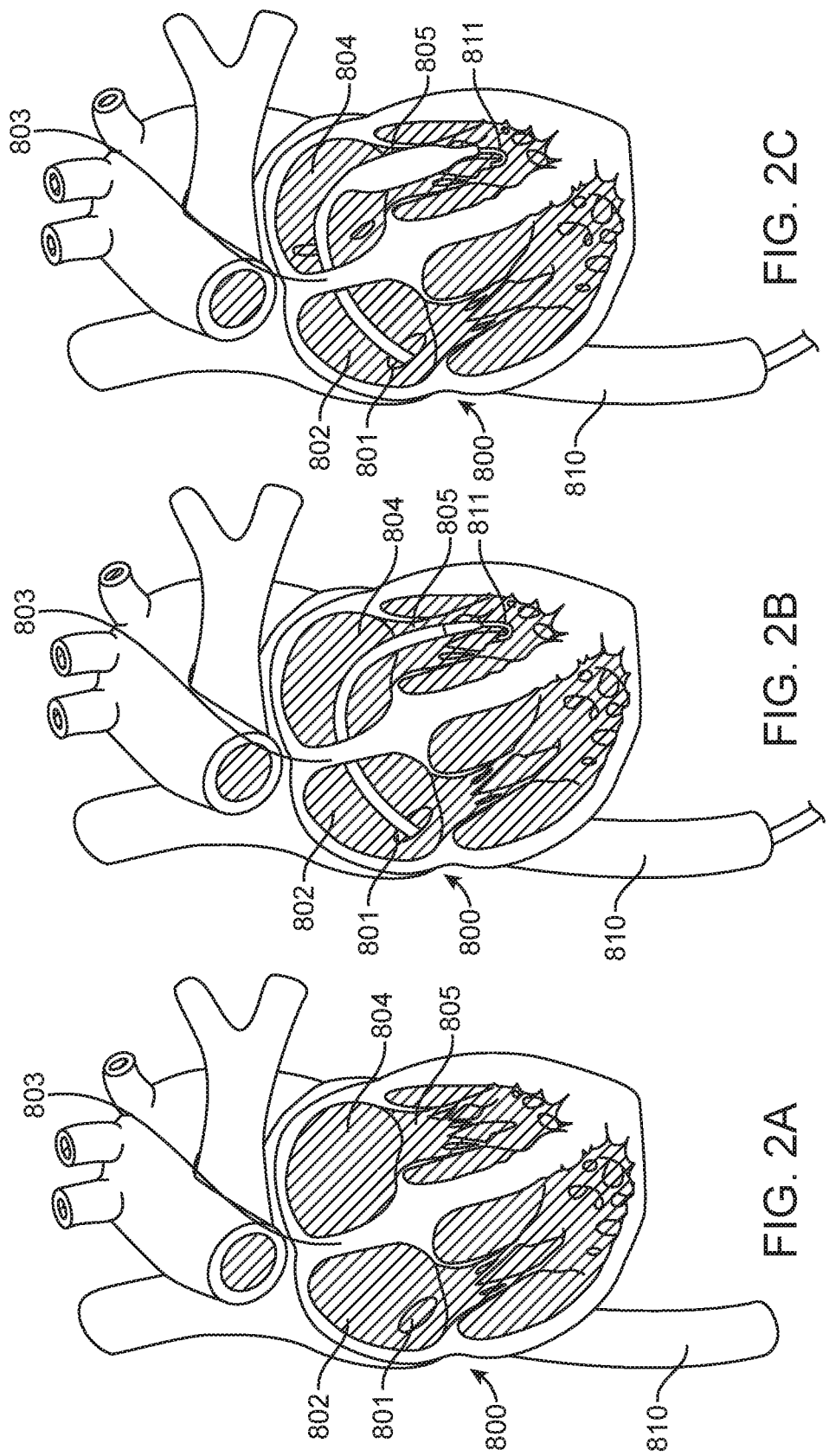
FIGS. 2A-2F are sequential views of the procedural pathway traversed by the prosthesis during a transseptal implantation procedure.
Figures 2D, 2E, 2F:
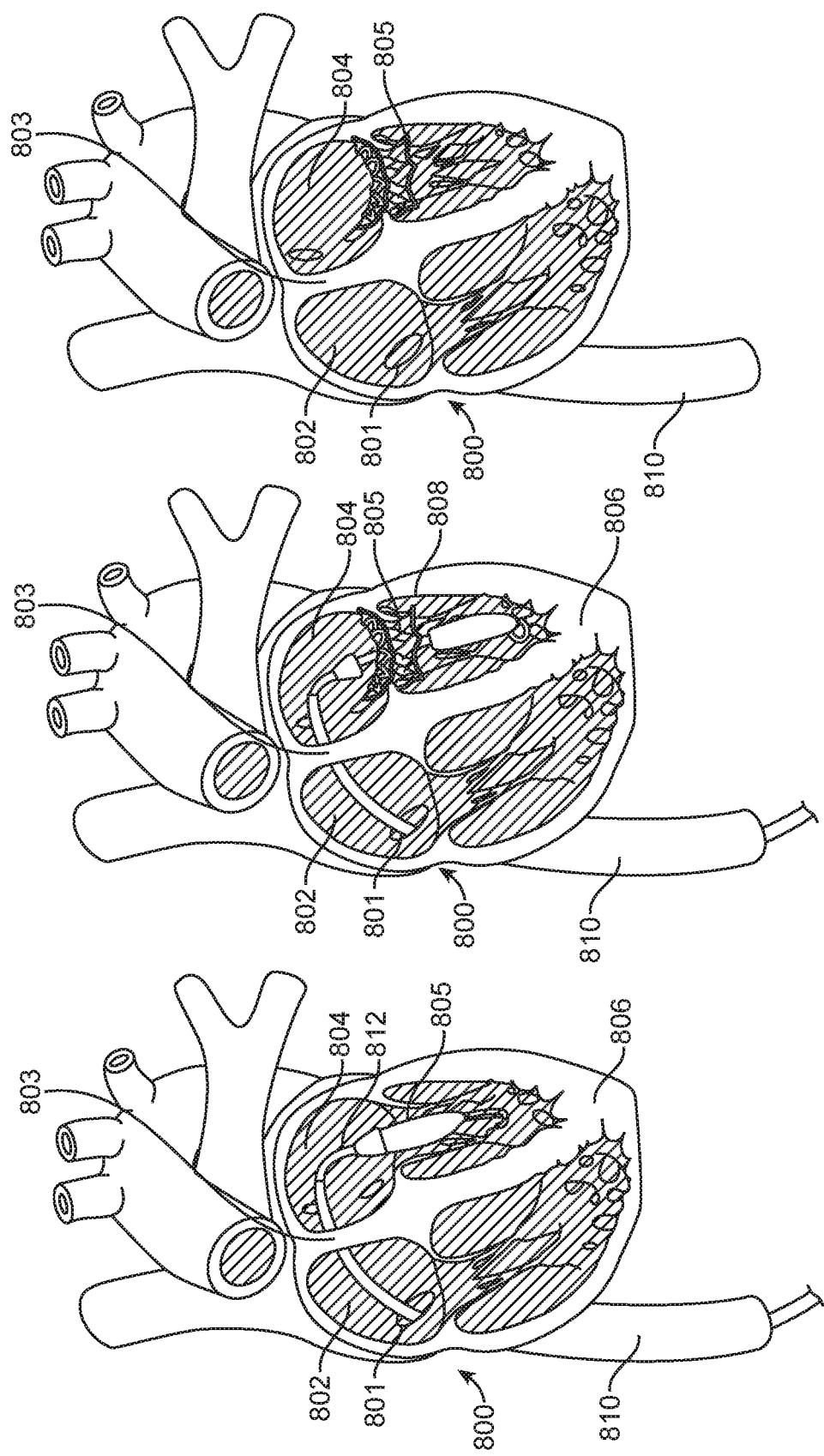

Turning now to FIGS. 2A-2F, the sequence of steps generally followed during a transseptal valve implantation are incorporated for reference. FIG. 2A describes a general depiction of a partial view (with anterior ventricular surface, pulmonary trunk, and aorta removed) of a human heart 800. The steering guide 7 will follow a guidewire 811 that has previously been placed in order to provide a path that leads to the target implant site. During a typical procedure, the steering guide 7 will enter the inferior vena cava 810 by way of the descending inferior vena cava (not shown) and first an incision at the femoral vein near the groin (not shown). The steering guide 7 will then exit the inferior vena cava 810 through a caval foramen 801 which acts as an inlet to the right atrium 802 (FIG. 2B). Once in the right atrium 802, the steering guide 10 will then penetrate the foramen ovale 803 in the septal wall and gain access to the left atrium 804. At the left atrium 804 (FIG. 2C), the steering guide 10 will be aimed towards the mitral annulus 805 in order to provide a direct channel towards the implant site (mitral annulus 805) for the delivery catheter 812 (FIG. 2D) to operate within. Once at the target implant site (FIG. 2E), the delivery catheter 812 will operate to deploy the prosthetic valve 808. Once the valve 808 has been deployed, the delivery catheter 812 can be fully removed (FIG. 2F).

Again turning, now to FIGS. 3A-3D, the sequence of steps generally followed during a transaortic valve implantation are incorporated for reference. FIG. 3A describes a general depiction of a partial view (with anterior ventricular surface, pulmonary trunk, and aortic root surface removed) of a human heart 800. The steering guide 7 will again follow a guidewire 811 that has previously been placed in order to provide a path that leads to the target implant site. During a typical procedure, the steering guide 7 will enter the descending aorta 813 by way of an incision at the femoral artery near the groin (not shown). The steering guide 7 will then continue up the descending aorta 813 and cross the aortic arch 814 before passing through the aortic valve 815 and descending into the left ventricular outflow tract 816 (LVOT). After emerging from the LVOT 816, and entering the left ventricle 817, the steering guide 7 must then make a sharp turn and point upward and towards the mitral annulus 805. At this point, the delivery catheter 812 may be advanced within the steering guide 7 in order to approach the target implant site (mitral annulus 805). Once at the target implant site (FIG. 2E), the delivery catheter 812 will operate to deploy the prosthetic valve 808. Once the valve 808 has been deployed, the delivery catheter 812 can be fully removed (FIG. 2F).

Figure 4:
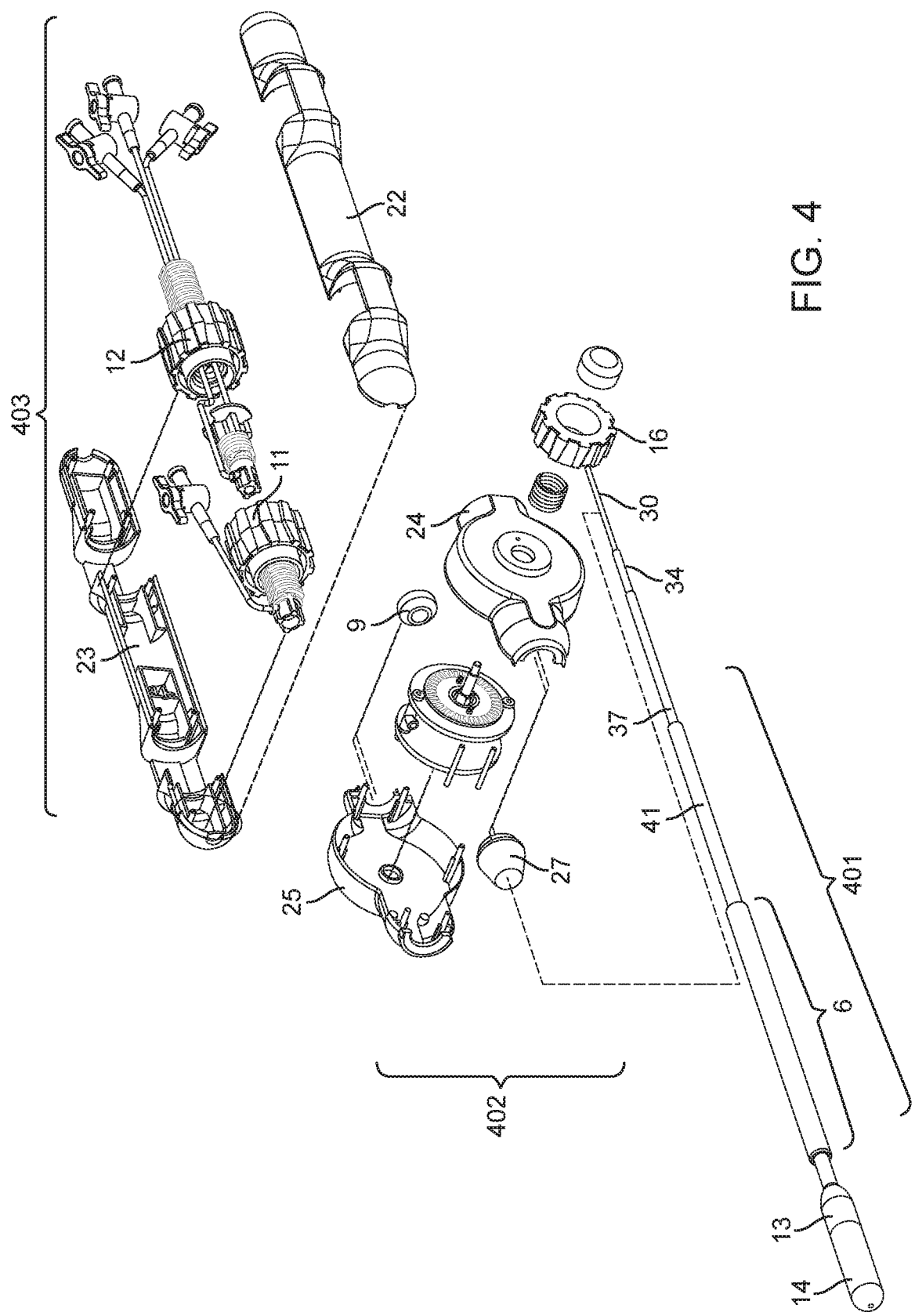
FIG. 4 is an assembly view of the delivery system seen in FIG. 1.

With particular reference to FIGS. 4-7, the internal mechanisms of the transseptal delivery system 1 that permit functionality will be described. Specifically, FIG. 4 illustrates an example of an assembly of a transseptal delivery system 1 shown in exploded view. The transseptal delivery system 1 is displayed in sections in order to make description of the internal parts more easily understood. Delivery handle section 403 will be described in further detail below with reference to FIG. 5. Steering handle section 402 will be described in further detail below with reference to FIG. 6. Finally, delivery catheter section 401 has previously been described above with reference to FIG. 7.

Figure 5:
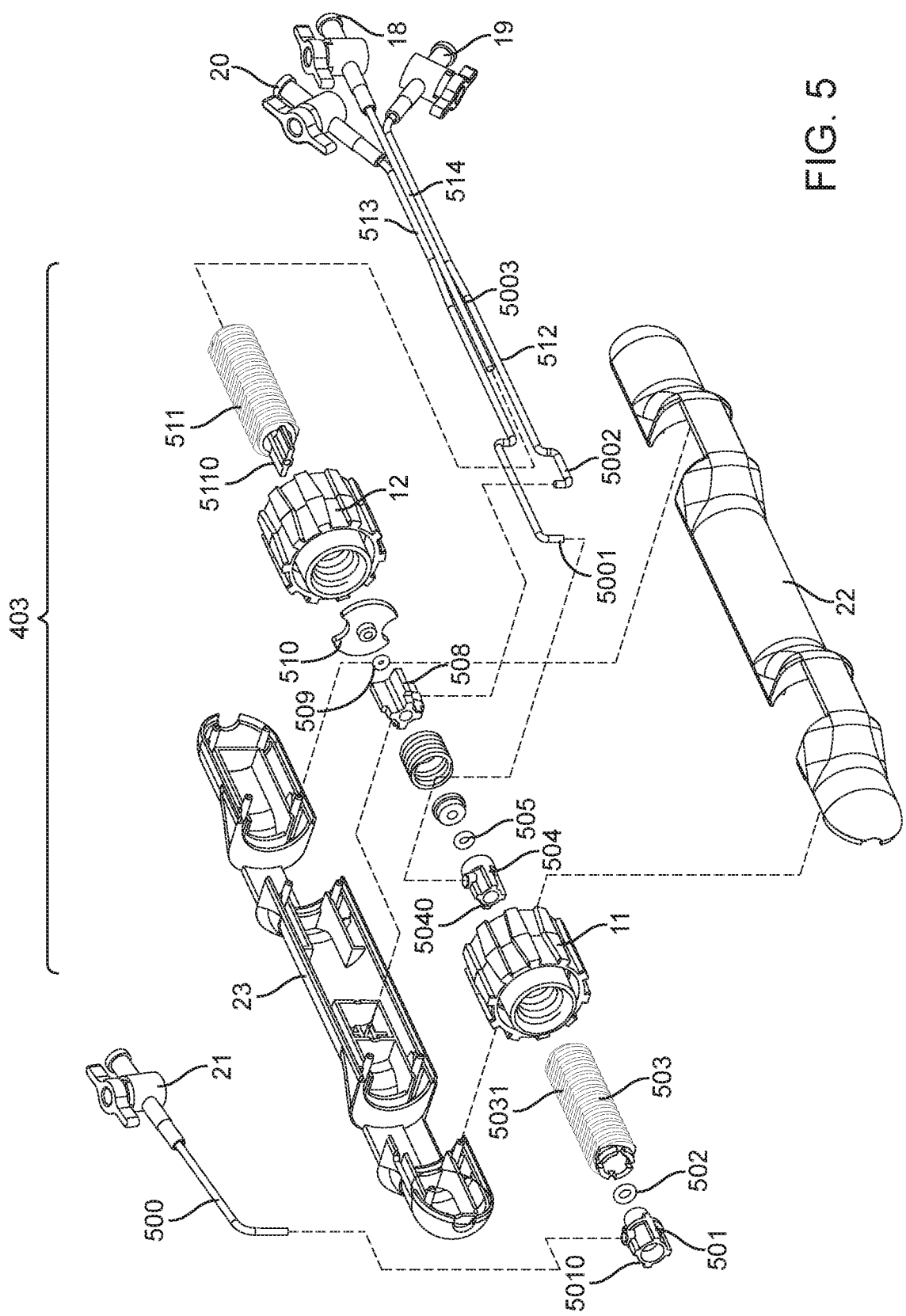
FIG. 5 is an assembly view of the delivery handle portion of the delivery system seen in FIG. 1.

Referring now to FIG. 5, the delivery handle section 403 is generally comprised of an A-side delivery handle housing 22 that is in mating connection with a B-side delivery handle housing 23, actuators such as a plurality of thumbwheels (distal thumbwheel 11 and proximal thumbwheel 12), a plurality of force transferring leadscrews (distal leadscrew 503 and proximal leadscrew 511) that may translate proximally or distally depending on the rotation of the thumbwheel within said plurality of thumbwheels, a plurality of hemostatic ports and related tubing (hemo-port A 21, hemo-port B 20, hemo-port C 18 and hemo-port D 19) which provide the ability to remove entrained air boluses from concentrically nested catheters within the system, and various other components and fasteners that shall be described in further detail. Referring specifically to the motion transferring elements of the delivery handle section 403, a distal leadscrew 503 is in threaded connection with a distal thumbwheel 11 and by turning said distal thumbwheel 11, translational motion is imparted upon the distal leadscrew 503. The motion of the distal leadscrew 503 is transferred to the sheath catheter 41 by way of a connection between the proximal end 42 of the sheath catheter 41 and the distal end 5010 of the distal leadscrew cap 501, which itself is mated with adhesive (medical grade UV cure adhesive, or medical grade cyanoacrylate adhesive, or any suitable medical grade adhesive for plastics or polymers, etc.) to the distal leadscrew 503. The distal leadscrew cap 501 also permits the ejection of air by way of a sealed interface (distal O-ring 502) between the sheath catheter 41 and the anchoring catheter 37, and an outlet hemo-port A 21. A stationary screw cap 504 is entrained within the A and B side handle housings 22, 23 respectively, and provides location and retention for the anchoring catheter 37, whereby the proximal end 38 of the anchoring catheter 37 is in mated connection (medical grade UV cure adhesive, or medical grade cyanoacrylate adhesive, or any suitable medical grade adhesive for plastics or polymers, or by way of fastening mechanical threads) with the distal end 5040 of the stationary screw cap 504. The stationary screw cap 504 also permits the ejection of air by way of a sealed interface (medial O-ring 505) between the anchoring catheter 37 and the bell catheter 34, and an outlet hemo port B 20. A proximal leadscrew 511 is in threaded connection with a proximal thumbwheel 12 and by turning said proximal thumbwheel 12, translational motion is imparted upon the proximal leadscrew 511. The motion of the proximal leadscrew 511 is transferred to the guidewire catheter 30 by way of a connection between the proximal end 31 of the guidewire catheter 30 and the distal end 5110 of the proximal leadscrew 511. Proximal leadscrew 511 motion is also transferred to the bell catheter 34 by way of a slidable interference between the distal end 5110 of the proximal leadscrew 511 and the proximal leadscrew plate 510, whereby the proximal leadscrew plate 510 is in mated connection with the proximal leadscrew cap 508, and the proximal leadscrew cap 508 houses the proximal end 35 of the bell catheter 34. The proximal leadscrew cap 508 also permits the ejection of air by way of a sealed interface (proximal O-ring 509) between the bell catheter 34 and the guidewire catheter 30, and an outlet hemo-port C 19. The proximal leadscrew 511 permits the ejection of air by way of an outlet hemo-port D 18 which is in mated connection with the proximal leadscrew 511.

Figure 6:
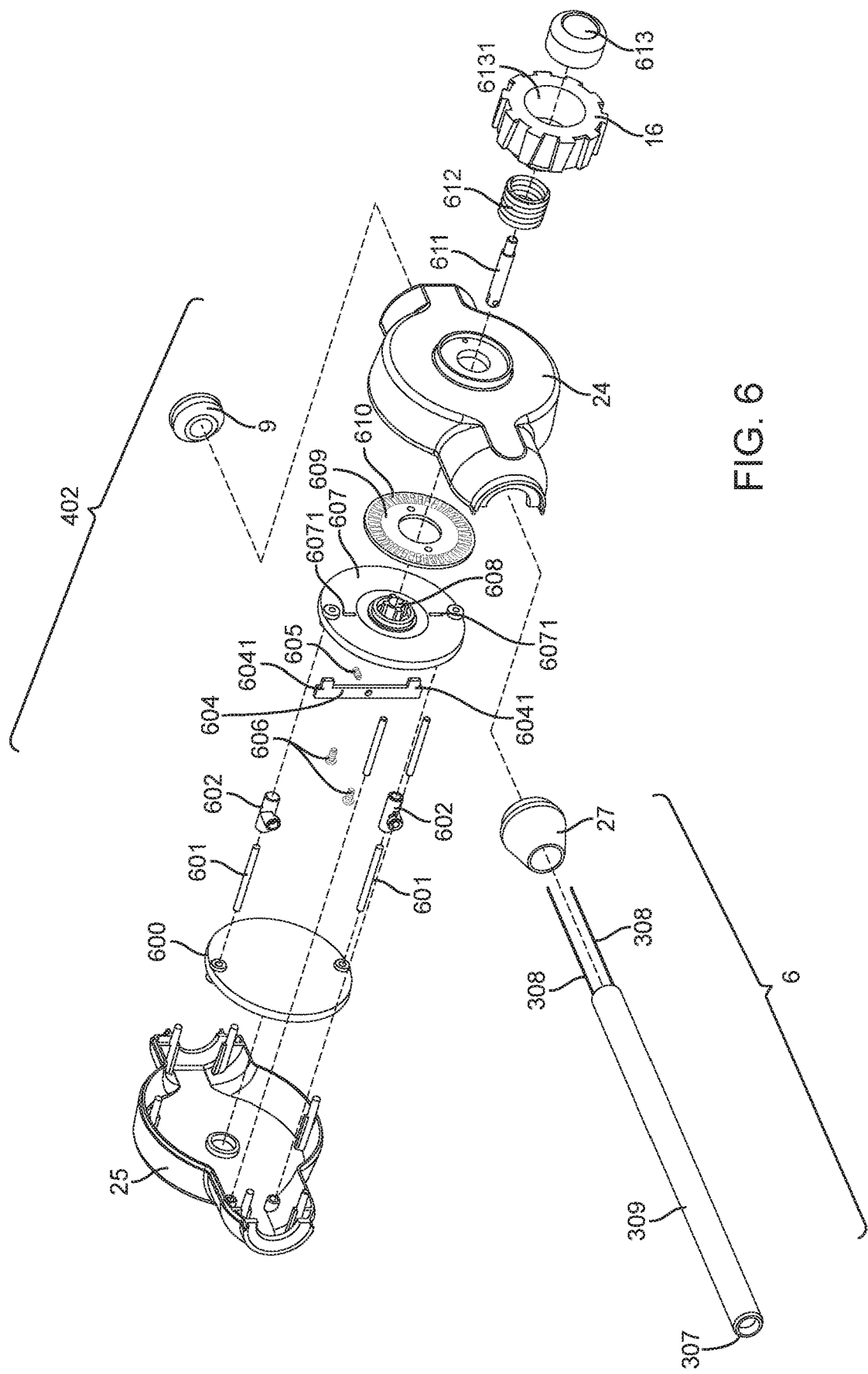
FIG. 6 is an assembly view of the steering guide portion of the delivery system seen in FIG. 1.

Referring now to FIG. 6, the steering handle section 402 is generally comprised of an A-side steering handle housing 24 that is in mating connection with a B-side steering handle housing 25, a steerable catheter assembly 6 that is in mating connection with a catheter strain relief 27, an interface 9, a plurality of rotatable disks (B-side rotatable disk 600 and A-side rotatable disk 607), a steering thumbwheel 16, a push button 613, and various other components and fasteners that shall be described in further detail. Referring specifically to the steering elements of the steering handle section 402, a steering thumbwheel 16 is in mating connection with a locking hub 608 that is centered within the A-side rotatable disk 607. The A-side rotatable disk 607 and B-side rotatable disk 600 are coupled together by way of a plurality of carrier rods 601, and work mechanically to spin within the handle housing that is comprised of the A-side steering handle housing 24 and B-side steering handle housing 25. Since the A-side rotatable disk 607 is connected to the steering thumbwheel 16, rotation of the steering thumbwheel 16 causes rotation of the A-side rotatable disk 607. A specific function of the plurality of rotatable disks (B-side rotatable disk 600 and A-side rotatable disk 607) is to actuate the plurality of pull wires 308 by way of tensioning hinges 602 that may spin freely on the carrier rods 601 and that are also connected to the pull wires 308 and also apply tension to them when turned. Referring now specifically to the locking elements of the steering handle section 402, a push button 613 is in threaded connection with a push button pin 611 that acts as a shaft. The push button 613 is located within a cavity 6131 that allows for direct translation when the button is depressed. A push button spring 612 is housed between the inside surface of the push button 613, and the bottom of the cavity 6131 and provides return force for when the depressed push button 613 is released. Motion from the push button 613 is transferred along the push button pin 611 directly to a cross bar 604 that is fastened to the push button pin 611 by way of a setscrew 605. When the push button pin 611 translates as the push button 613 is depressed, the cross bar 604 also translates and a plurality of cross bar pegs 6041 that are located on the ends of the cross bar 604 thus translate as well. When in an undepressed state, the cross-bar pegs 6041 are seated within a plurality of slots 6071 that appear on the periphery of the A-side rotatable disk 607. The cross bar pegs 6041 then also project through the slots 6071 and may rest within any of the circumferential slits 610 that appear in an array about the periphery of a position disk 609 that is mounted to the inside surface of the A-side steering handle housing 24 by threaded fasteners 606. When in a depressed state, the cross bar pegs 6041 are moved away from the circumferential slits 610 until clearance is achieved, and the locking mechanism enables free rotation of the cross bar 604, as well as all aspects that are directly connected to the A-side rotatable disk 607. Further detail regarding the mechanics behind the locking mechanism can be seen in FIG. 9.

By way of cross-sectional illustration, FIGS. 8A-8D show specific internal features of the devices described herein, and will now be relied upon to reveal further detail. FIG. 8A depicts the entire transseptal delivery system 1 comprised of a distal end 3, a steerable catheter assembly 6, a steering handle 5, and a delivery handle assembly 4 therebetween the distal end 3 and the proximal end 2. At the distal end 3 of the transseptal delivery system 1 is located the distal 14 and proximal 13 capsules, which entrain a prosthetic valve therein. An articulated end 15 of the steerable catheter assembly 6 is in mating connection with the distal-most portion of the steering handle 5, which locates and controls it thereby. The steering thumbwheel 16 provides actuation control of the articulated end 15 of the steerable catheter assembly 6. Continuing proximally, the delivery handle assembly 4 is depicted, which houses the distal 11 and proximal 12 thumbwheels, each being responsible for the translation of the proximal 13 and distal 14 capsules, respectively. A hemo-port A 21 is provided and housed by the A-side delivery handle housing 22 and B-side delivery handle housing 23 (not shown). Further hemo-ports B, C, and D (20, 19, and 18 respectively) are also provided, the functions of which being described in greater detail in previous sections.

FIG. 8B introduces a cross-sectional view AA of the aforementioned depiction in FIG. 8A, which reveals the internal mechanisms of the distal end 3, the steering handle 5, and the delivery handle assembly 4. Cross-section AA of FIG. 8B shows the internal surfaces of the distal capsule 14, and the proximal capsule 13, as well as the articulated end 15 of the steerable catheter assembly 6, all of whose mechanical interactions have been described previously above. Also depicted is an internal view of the steering handle 5, and the delivery handle assembly 4 which displays the elements distal 11 and proximal 12 thumbwheels, and A-side delivery handle housing 22. A detail section C 250 is provided, whereby the enlarged illustration of the contents of detail section C 250 appear in FIG. 8C.

As mentioned, FIG. 8C is the enlarged illustration of the contents of detail section C 250 of FIG. 8B, and further detail of the internal features of the valve capsule assembly 8 are hereby provided. It can be seen that the distal capsule 14 is internally threaded at a threaded portion 460, which provides mating means for a guidewire catheter threaded insert 490 that is embedded near the distal end 32 of the guidewire catheter 30. Similarly, the bell 36 is internally threaded at a threaded portion 470, which provides mating means for a bell catheter threaded insert 500 that is embedded near the distal end 360 of the bell catheter 34. Similarly, the anchor 400 is internally threaded at a threaded portion 480, which provides mating means for an anchoring catheter threaded insert 510 that is embedded near the distal end 39 of the anchoring catheter 37. Further regarding the bell 36, it can be seen that the bell 36 is shown in position and concentrically oriented to the distal-most portion 450 of the anchor 400, over which it may translate when actuated accordingly by the delivery handle assembly 4 (not shown). It should be apparent that the connected pair that is comprised of the distal capsule 14 and guidewire catheter 30 may move in tandem concentrically within the similarly connected pair that is comprised of the bell 36 and bell catheter 34, which may also move in tandem concentrically within the similarly connected pair that is comprised of the anchor 400 and anchoring catheter 37 which are stationary, but inherently flexible by virtue of their construction. The proximal capsule 13 by way of attachment to the sheath catheter 41 also form a connected pair that may move in tandem concentrically over the previously discussed catheters.

FIG. 8D depicts the result of the cross-section B-B introduced in FIG. 8A. As previously described, a plurality of handle housings, A-side 24 and B-side 25 are in mated connection and form the entirety of the housing which comprises the steering handle 5. Within this cross-section B-B of FIG. 8D can also be seen a plurality of carrier rods 601 that matingly pin together the A-side 607 and B-side 600 rotatable disks. Also shown are the cross bar 604, push-button pin 611, and setscrew 605 that fasten said bar and said pin together in mating connection. The steering thumbwheel 16, which houses the push button 613 and by extension the push button spring 612 is further revealed, additionally.

Figure 9A:
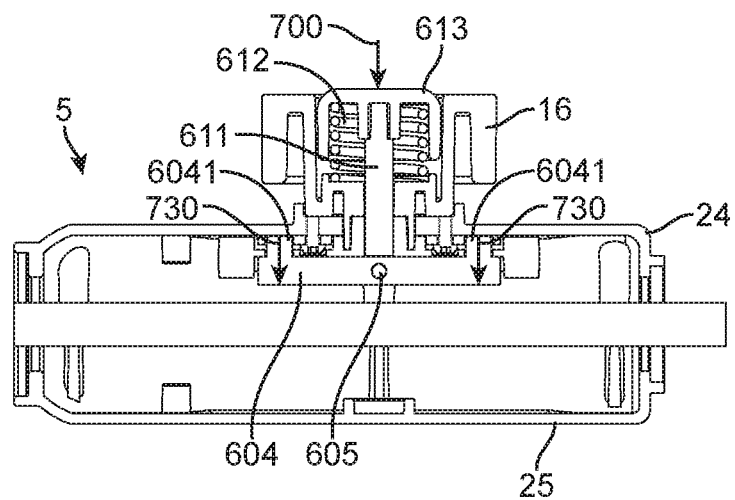
FIGS. 9A-9C are cross-sectional views of the steering handle portion taken along the line A-A in FIG. 8A.
Figure 9B:
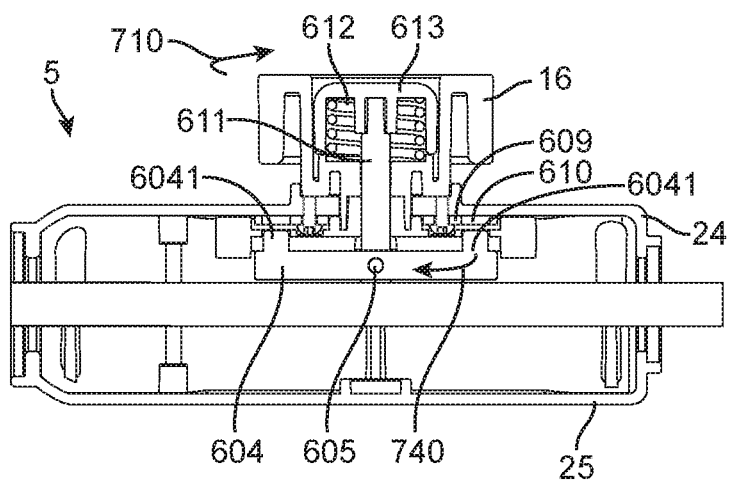
Figure 9C:
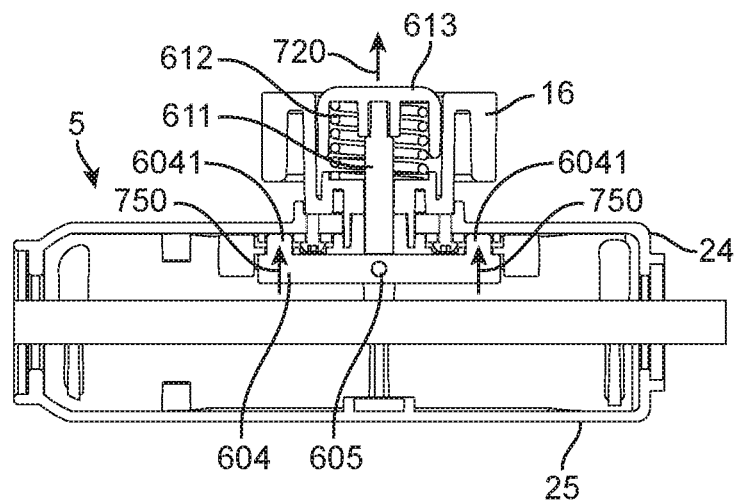

FIGS. 9A-9C illustrate the internal mechanics of the locking mechanism that is inherent to the steering handle 5 (of which these figures provide a cross-sectional view), and further illustrate the dynamic relationships between the components, and the manner in which they may be operated. Beginning with FIG. 9A, the sequence of operation that comprises pushing a button, turning a knob, and then releasing the button while maintaining an achieved angular position by the button is set forth. Specifically, FIG. 9A depicts the depression (arrow indicating translation 700) of the push button 613 that is mounted within the steering thumbwheel 16 and biased internally by the opposing force of the push button spring 612. As the push button 613 is matingly connected to the cross bar 604 by way of the push button pin 611 and the setscrew 605, when the push button 613 is translated through depression, the cross bar 604 is also translated (arrows indicating translation 730) in the same direction as the push button 613. Once the cross bar 604 is fully translated, a plurality of cross bar pegs 6041 described on the ends of the cross bar 604 become disengaged from circumferential slits 610 (FIG. 9B) that are provided by the position disk 609 (FIG. 9B).

Continuing within FIG. 9B, once the cross bar 604 is unconstrained it is thus free to rotate (arrows indicating rotation 740) by the application of a torque to the steering thumbwheel 16 (arrows indicating rotation 710).

FIG. 9C provides the final step in the operation of the push button 613 mechanism of the steering thumbwheel 16 for steering and positional lockout. After the appropriate rotational position is achieved with the steering thumbwheel 16, the push button 613 is released. This allows for translation in the opposite direction (arrows indicating translation 720) to that experienced when the push button 613 is depressed, due to the biasing force of the push button spring 612. Releasing the push button 613 also allows the cross bar 604 to translate (arrows indicating translation 750) and by extension, the cross bar pegs 6041 may thus achieve re-engagement with the circumferential slits 610 (FIG. 9B) and provide lockout against further rotation of the steering thumbwheel 16 and by extension disruption of position of the steerable catheter 309 (not shown).

Turning now to FIGS. 10A-10D, a sequence of images is provided which depict the rotation of the steering thumbwheel 16 and the ensuing effect at the valve capsule end of the system. Beginning with FIG. 10A, when a torque is applied to the steering thumbwheel 16, rotational motion is transferred to the A-side rotatable disk 607, which is in communication with a plurality of pull wires 308 that are further internally embedded at the articulated end 15 of the steerable catheter assembly 6. The pull wires act to pull the articulated end 15 of the steerable catheter assembly 6 in the direction of steering thumbwheel 16 rotation. Further application of torque (FIG. 10B-10D) results in a further rotation of the steering thumbwheel 16 and yet further bending of the articulated end 15 of the steerable catheter assembly 6.

Now with specific reference to FIGS. 11A-11D, a particular example of a valve capsule assembly 8, and general deployment sequence of a transcatheter valve prosthesis are herein illustrated. Details regarding the transcatheter valve prosthetic referenced herein are described in U.S. Pat. No. 8,579,964 to Lane et. al. As depicted in FIG. 11B, a transcatheter valve prosthesis 1100 is entrained within the valve capsule assembly 8, after having been crimped (details regarding the loading device used to crimp said transcatheter valve prosthetic are described in U.S. Pat. Publication. No. 2014/0155990, the entire contents of which are incorporated herein by reference, and loaded therein. The valve capsule assembly 8 can comprise a generally cylindrical structure having a proximal end and a distal end, wherein each of the proximal and distal ends terminates in a rounded dome-like surface. As shown in FIG. 1, the valve capsule assembly can comprise a proximal capsule 13 and a distal capsule 14, wherein the proximal capsule 13 is disposed at a proximal end of the valve capsule assembly, and the distal capsule 14 is disposed at a distal end of the valve capsule assembly. Each of the proximal capsule 13 and the distal capsule 14 can have a cylindrical portion with one end of the cylindrical portion having an open circular shape and the other end having a cap portion that can have a rounded dome-like surface. As shown in FIG. 3, the open circular shape of proximal capsule 13 can be configured to meet with or abut against the open circular shape of distal capsule 14, with the cap portion of the proximal capsule forming the proximal end of the valve capsule assembly, and the cap portion of the distal capsule forming the distal end of the valve capsule assembly.

FIG. 11C illustrates the valve 1100 in staged deployment after the proximal capsule 13 has been translated away from the valve 1100, and the atrial skirt 1101 has been revealed and allowed to self-expand. FIG. 11D illustrates the valve 1100 with the atrial skirt 1101 fully expanded, after the distal capsule 14 has been translated away from the valve 1100. A plurality of trigonal anchoring tabs 1102 have also been revealed by the movement of the distal capsule 14. FIG. 11E illustrates final deployment of the valve 1100, whereby the distal capsule 14 has translated to its maximum displacement, and the bell 36 on the bell catheter 34 has also translated maximally in order to release anchoring features of the valve (not shown) until finally full release of the valve from the delivery device has been achieved, and the valve 1100 is no longer anchored to any part of the valve capsule assembly 8.

With particular reference to FIGS. 12A-12D, an alternative example of a valve capsule assembly 1205 is herein illustrated. FIG. 12A depicts a valve capsule assembly 1205 which can be comprised of a proximal capsule 13, a distal capsule sleeve 1200, and an optional balloon tip 1201 or a tapered tip. The balloon tip 1201 may be inflated or deflated in order to optimize space constraints that are inherent to the anatomical limitations found within the left ventricle of the human heart, whereby deflating the balloon tip 1201 allows the distal capsule sleeve 1200 (which is generally configured to be shorter in overall length than the previously described proximal capsule 14, FIG. 1) to translate over the balloon tip 1201 in order to enable typical deployment.

Figure 13D:
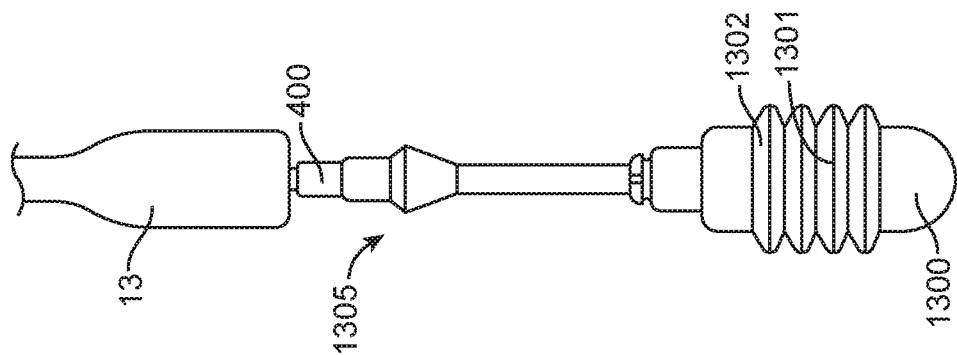
FIGS. 13A-13D are sequential partial views of an alternative example of the valve capsule portion of the delivery system of FIG. 1.
Figure 13C:
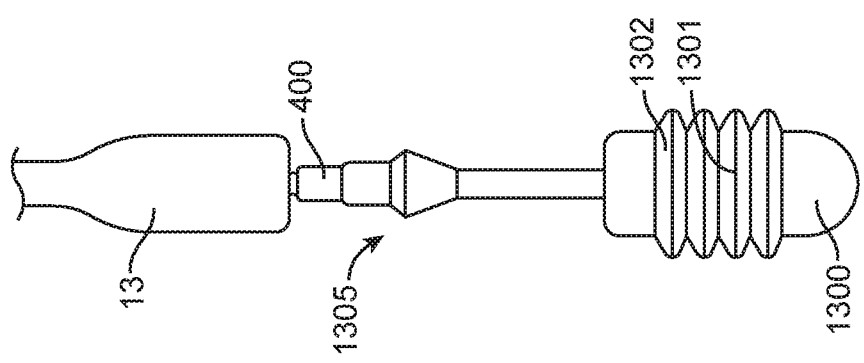
Figure 13B:
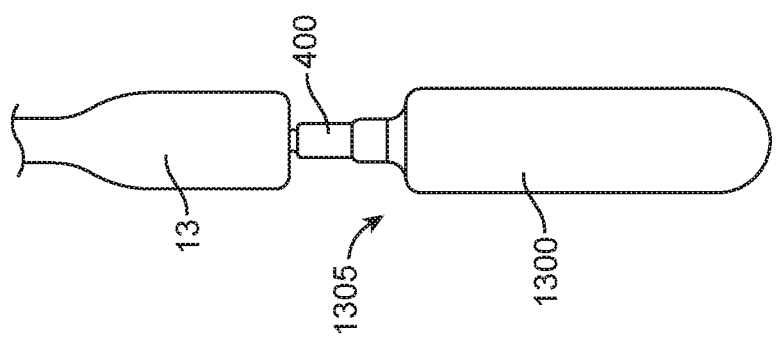
Figure 13A:
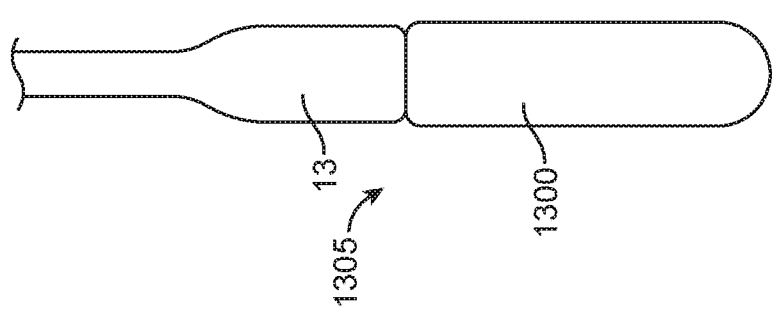

With particular reference to FIGS. 13A-13D, an alternative example of a valve capsule assembly 1305 is herein illustrated. FIG. 13A depicts a valve capsule assembly 1305 which is comprised of a proximal capsule 13, and a collapsible distal capsule 1300. The collapsible distal capsule 1300 generally translates and functions in the manner of an accordion, in order to optimize space constraints that are inherent to the anatomical limitations found within the left ventricle of the human heart, whereby collapsing the distal capsule 1300 to enable typical deployment requires moving the body of the capsule into the left ventricle a shorter distance than that anticipated by the previously described proximal capsule 14 (FIG. 1). The operational function of the collapsible distal capsule 1300 relies on the actuation of a plurality of stacked rings 1301 or stackable elements that can be joined in series and can generally covered by a shroud 1302 that may be comprised of fabrics, polymers, metallic alloys or any combination thereof.

Figure 14D:
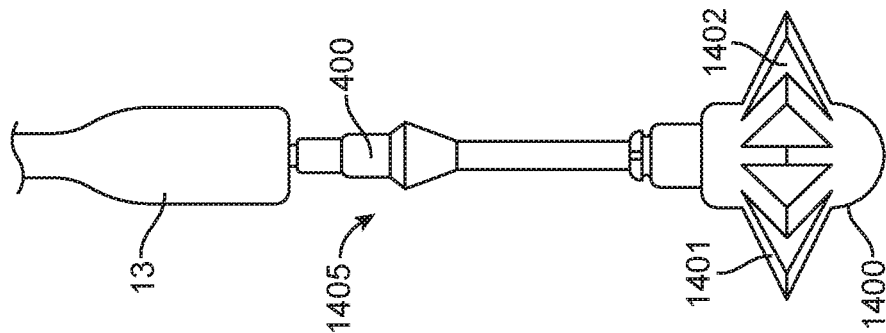
FIGS. 14A-14D are sequential partial views of an alternative example of the valve capsule portion of the delivery system of FIG. 1.
Figure 14C:
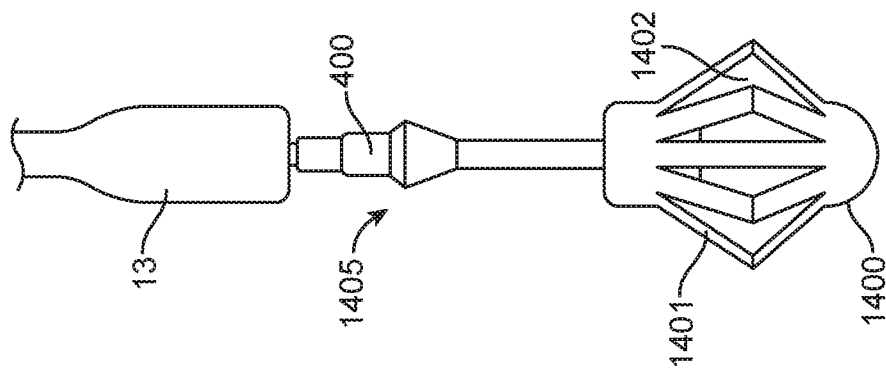
Figure 14B:
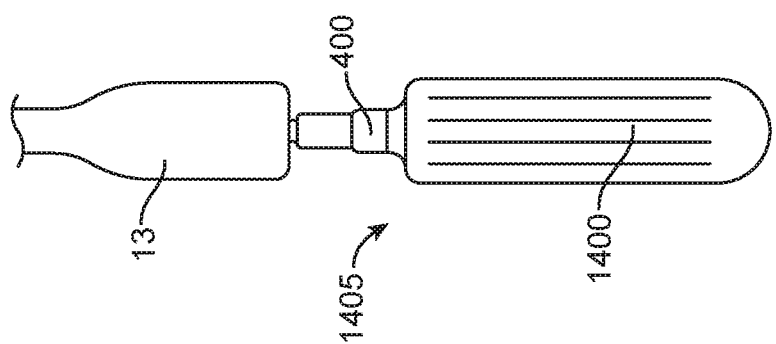
Figure 14A:
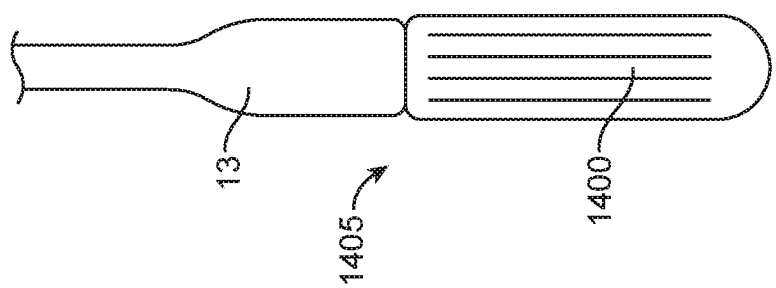

Any example of a valve capsule assembly may be used in any delivery catheter as described herein. With particular reference to FIGS. 14A-14D, an alternative example of a valve capsule assembly 1405 is herein illustrated. FIG. 14A depicts a valve capsule assembly 1405 which is comprised of a proximal capsule 13, and a collapsibly splined distal capsule 1400. The collapsibly splined distal capsule 1400 generally translates and functions in the manner of an umbrella, in order to optimize space constraints that are inherent to the anatomical limitations found within the left ventricle of the human heart, whereby collapsing the splined distal capsule 1400 to enable typical deployment requires moving the body of the capsule into the left ventricle a shorter distance than that anticipated by the previously described proximal capsule 14 (FIG. 1). The operational function of the collapsibly splined distal capsule 1400 relies on the actuation of plurality of hinged splines 1401 that are joined in parallel and generally covered by a shroud 1402 that may be comprised of fabrics, polymers, metallic alloys or any combination thereof. The splines 1401 can be arm-like parallel structures formed by a series of parallel cuts or incisions along a longitudinal surface of the cylindrical portion of the capsule, wherein the hinges of the splines allow each arm-like structure to bend, thus compressing or collapsing the distal capsule.

With particular reference to FIGS. 15A-15D, an alternative example of a valve capsule assembly 1505 is herein illustrated. FIG. 15A depicts a valve capsule assembly 1505 which is comprised of a proximal capsule 13, and a collapsibly wired distal capsule 1500. The collapsibly wired distal capsule 1500 generally translates and functions in the manner of a flag pole (relying on the push/pull of the rigid plurality of wires 1502) in order to optimize space constraints that are inherent to the anatomical limitations found within the left ventricle of the human heart, whereby collapsing the wired distal capsule 1500 to enable typical deployment requires moving the body of the capsule into the left ventricle a shorter distance than that anticipated by the previously described proximal capsule 14 (FIG. 1). The operational function of the collapsibly wired distal capsule 1500 relies on the actuation of plurality of nitinol or similar alloy wires 1502 that are joined in parallel and proximally fastened to a structural ring 1501 and generally covered by a shroud 1504 that may be comprised of fabrics, polymers, metallic alloys or any combination thereof. Distally, the plurality of nitinol wires 1502 may be withdrawn into a plurality of distal slots 1506, and then finally a distal lumen 1507 (not shown) that resides inside of a distal cap 1503 in order to cinch the capsule in its entirety, and translate it away from the distal portion of the valve. In one particular example, the distal lumen 1507 (not shown) would comprise an additional lumen (not shown) appearing within the guidewire catheter (30, FIG. 7) the additional lumen (not shown) traversing the entire delivery system and exiting through the delivery system A and B side handle halves 22, 23 respectively. The plurality of nitinol wires 1502 would traverse and exit the additional lumen (not shown), and be graspable and pullable for deployment, by an operator.

With particular reference to FIGS. 16A-16D, an alternative example of a valve capsule assembly 1605 is herein illustrated. FIG. 16A depicts a valve capsule assembly 1605 which is comprised of a proximal capsule 13, and a shape memory distal capsule 1600. The shape memory distal capsule 1600 generally translates and functions in the manner of an accordion, in order to optimize space constraints that are inherent to the anatomical limitations found within the left ventricle of the human heart, whereby collapsing the shape memory distal capsule 1600 to enable typical deployment requires moving the body of the capsule into the left ventricle a shorter distance than that anticipated by the previously described proximal capsule 14 (FIG. 1). The operational function of the shape memory distal capsule 1600 relies on the actuation and stiffening of a stent-like nitinol or similar alloy frame 1600 by the temperature gradient within a patient's blood stream, that is further anchored to a structural cap 1601 and generally covered by a shroud 1601 that may be comprised of fabrics, polymers, metallic alloys or any combination thereof. A plurality of internal biasing wires 1603 enable the shape memory distal capsule 1600 to be collapsed when they are in tension, and to be extended when they are not in tension.

Prosthesis

FIG. 17A illustrates a perspective view of an example of a prosthetic mitral valve with optional coverings removed to allow visibility of the anchor struts. FIG. 17B illustrates a top view of the prosthetic valve in FIG. 17A from the atrium looking down into the ventricle. The valve 1700 includes an asymmetrical expanded anchor portion having a D-shaped cross-section. As shown, the anchor portion generally comprises anterior 1702 and posterior 1704 aspects along the longitudinal axis thereof, as well as atrial 1706, annular 1708 and ventricular 1710 regions. Commissures (also referred to herein as commissure posts) 1713 are also shown. The prosthetic valve 1700 has a collapsed configuration and an expanded configuration. The collapsed configuration is adapted to loading on a shaft such as a delivery catheter for transluminal delivery to the heart, or on a shaft for transapical delivery through the heart wall. The radially expanded configuration is adapted to anchor the valve to the patient's native heart adjacent the damaged valve. In order to allow the valve to expand from the collapsed configuration to the expanded configuration, the anchor portion of the valve may be fabricated from a self-expanding material such as a nickel titanium alloy like nitinol, or it may also be made from spring temper stainless steel, or a resilient polymer. In still other examples, the anchor may be expandable with an expandable member such as a balloon. In examples, the anchor is fabricated by laser cutting, electrical discharge machining (EDM), or photochemically etching a tube. The anchor may also be fabricated by photochemically etching a flat sheet of material which is then rolled up with the opposing ends welded together.

The atrial skirt portion 1716 forms a flanged region that helps to anchor the prosthetic valve to the atrium, above the mitral valve. The atrial skirt includes a plurality of triangular fingers which extend radially outward from the anchor to form the flange. The posterior 1704 portion of the atrial skirt 1716 is generally round or circular, while a portion of the anterior 1702 part of the atrial skirt 1716 is flat. Thus, the atrial skirt region may have a D-shaped cross-section. This allows the prosthetic valve to conform to the patient's cardiac anatomy without obstructing other portions of the heart, as will be discussed below. Each triangular finger is formed from a pair of interconnected struts. The triangular fingers of the atrial skirt generally are bent radially outward from the central axis of the prosthetic valve and lie in a plane that is transverse to the valve central axis. In some examples, the atrial skirt lies in a plane that is substantially perpendicular to the central axis of the valve. The anterior portion 1702 of the atrial skirt 1706 optionally includes an alignment element 1714 which may be one or more struts which extend vertically upward and substantially parallel to the prosthetic valve. The alignment element 1714 may include radiopaque markers (not illustrated) to facilitate visualization under fluoroscopy. The alignment element helps the physician to align the prosthetic valve with the native mitral valve anatomy, as will be discussed later.

Disposed under the atrial skirt region is the annular region 1720 which also has a collapsed configuration for delivery, and an expanded configuration for anchoring the prosthetic valve along the native valve annulus. The annular region is also comprised of a plurality of interconnected struts that form a series of cells, that may be closed. Suture holes 1721 in some of the struts allow tissue or other coverings (not illustrated) to be attached to the annular region. Covering all or a portion of the anchor with tissue or another covering helps seal the anchor against the heart valve and adjacent tissue, thereby ensuring that blood is funneled through the valve, and not around it. The annular region may be cylindrical, but in any example has a posterior portion 1704 which is circular, and an anterior portion 1702 which is flat, thereby forming a D-shaped cross-section. This D-shaped cross-section conforms better to the native mitral valve anatomy without obstructing blood flow in other areas of the heart.

The lower portion of the prosthetic valve includes the ventricular skirt region 1728. The ventricular skirt region also has a collapsed configuration for delivery, and an expanded configuration for anchoring. It is formed from a plurality of interconnected struts that form a series of cells, that may be closed, that can radially expand. The ventricular skirt in the expanded configuration anchors the prosthetic valve to the ventricle by expanding against the native mitral valve leaflets. Optional barbs 1723 in the ventricular skirt may be used to further help anchor the prosthetic valve into the ventricular tissue. Barbs may optionally also be included in the atrial skirt portion as well as the annular region of the anchor. Additionally, optional suture holes 1721 in the ventricular skirt may be used to help suture tissue or another material to the ventricular skirt region, similarly as discussed above. The anterior 1702 portion of the ventricular skirt may be flat, and the posterior 1704 portion of the ventricular skirt may be circular, similarly forming a D-shaped cross-section to anchor and conform to the native anatomy without obstructing other portions of the heart. Also, the lower portions of the ventricular skirt serve as deployment control regions since the lower portions can remain sheathed thereby constraining the ventricular skirt from radial expansion until after the optional ventricular trigonal tabs and posterior tab have expanded, as will be explained in greater detail below.

The ventricular skirt portion may optionally also include a pair of ventricular trigonal tabs 1724 on the anterior portion of the anchor (only 1 visible in this view) for helping to anchor the prosthetic valve as will be discussed in greater detail below. The ventricular skirt may also optionally include a posterior tab 1726 on a posterior portion 1704 of the ventricular skirt for anchoring the prosthetic valve to a posterior portion of the annulus. The trigonal tabs 1724 or the posterior tab 1726 are tabs that extend radially outward from the anchor, and they are inclined upward in the upstream direction.

The actual valve mechanism is formed from three commissures posts (also referred to as commissures) 1713 which extend radially inward toward the central axis of the anchor in a funnel or cone-like shape. The commissures 1713 are formed from a plurality of interconnected struts that create the triangular shaped commissures. The struts of the commissures may include one or more suture holes 1721 that allow tissue or a synthetic material to be attached to the commissures. In this exemplary example, the valve is a tricuspid valve, therefore it includes three commissures 1713. The tips of the commissures may include a commissure tab 1712 (also referred to as a tab) for engaging a delivery catheter. In this example, the tabs have enlarged head regions connected to a narrower neck, forming a mushroom-like shape. The commissures may be biased in any position, but may angle inward slightly toward the central axis of the prosthetic valve so that retrograde blood flow forces the commissures into apposition with one another to close the valve, and antegrade blood flow pushes the commissures radially outward, to fully open the valve. FIG. 17B is a top view illustrating the prosthetic valve of FIG. 17A from the atrial side, and shows the D-shaped cross-section.

FIG. 18A illustrates the prosthetic mitral valve of FIGS. 17A-17B with a covering 1770 coupled to portions of the anchor with suture 1772. This view is taken from an atrial perspective. In this example, the covering may be pericardium which may come from a number of sources as disclosed elsewhere in this specification. In alternative examples, the covering may be a polymer such as Dacron polyester, ePTFE, or another synthetic material. The covering may be disposed over the annular region 1720 and the ventricular skirt region 1728, and in some examples the anterior ventricular trigonal 1724 tabs and the ventricular posterior tab 1730 may also be covered with the same or a different material. The covering helps seal the anchor against the adjacent tissue so that blood funnels through the valve mechanism. In this example, the atrial skirt is left uncovered, as well as tabs 1724, 1730. Additionally, radiopaque markers 1714*a* form a portion of the alignment element and facilitate visualization of the prosthetic valve under fluoroscopy which is important during alignment of the valve.

Figure 18B:
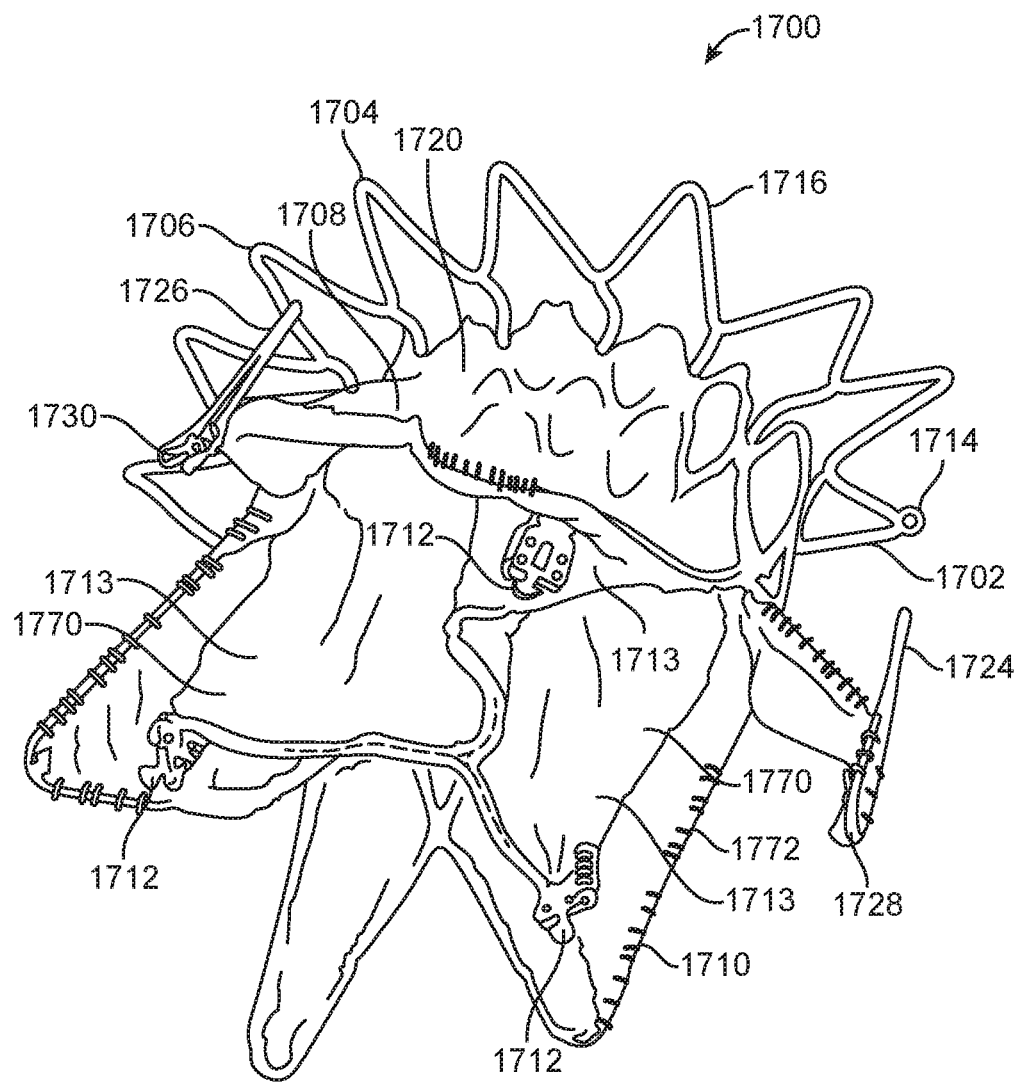
FIG. 18B illustrates a perspective view of the prosthetic valve in FIG. 17A.

FIG. 18B is a perspective view of the prosthetic mitral valve seen in FIG. 18A, as seen from the ventricle. The struts of the valve commissures are covered with the same material or a different material as the annular and ventricular regions as discussed above, thereby forming the tricuspid valve leaflets 1713. FIG. 18B shows the valve in the closed configuration where the three leaflets are engaged with one another preventing retrograde blood flow. Commissure tabs 1712 remain uncovered and allow the commissures to be coupled with a delivery device as will be explained below. The prosthetic valve in FIGS. 18A-18B may be sterilized so they are suitable for implantation in a patient using methods known in the art.

Introducer Sheath

An introducer sheath may be used to facilitate access to a vein or artery of the patient so that any of the delivery catheters or delivery systems disclosed herein may be introduced into the vein or artery and deliver any one of prostheses disclosed herein to a target treatment region in the patient. Not only does the introducer sheath facilitate vascular access but the introducer sheath also may have a hemostasis valve that prevents blood leakage due to backflow of blood from the pressurized vein or artery out of the proximal end of the sheath.

Figure 19A:
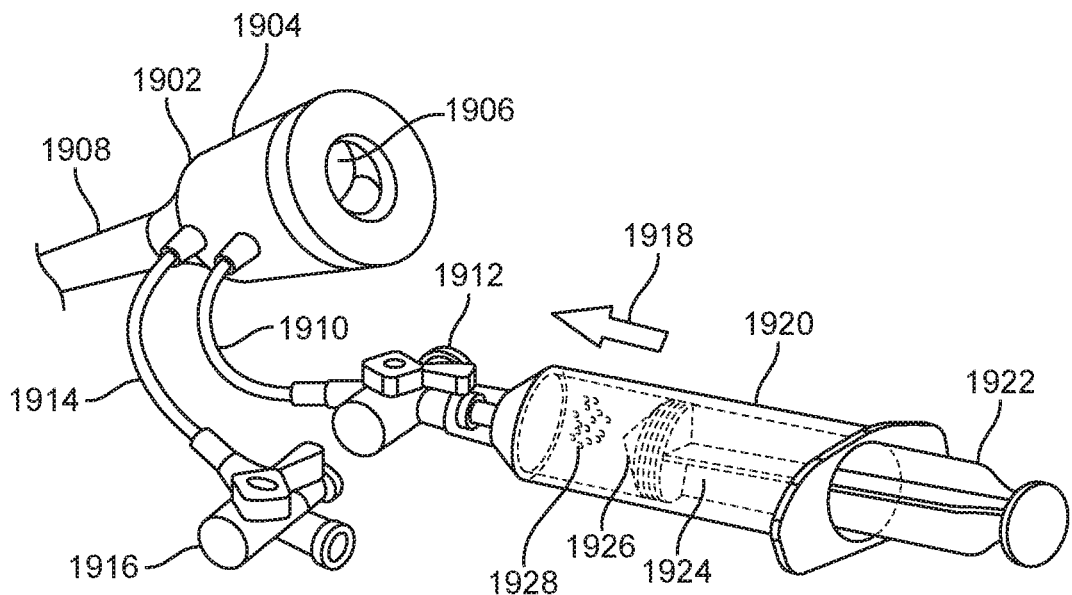
FIGS. 19A-19B illustrate an introducer sheath with a hemostasis valve in the closed and open positions, respectively.
Figure 19B:
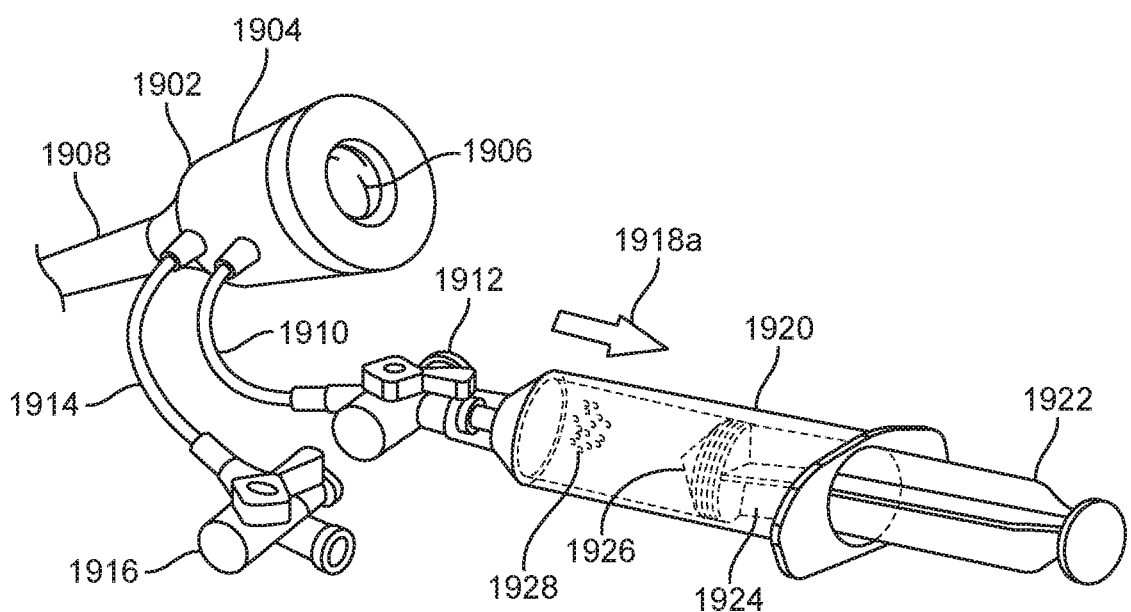

FIGS. 19A-19B illustrate an example of an introducer sheath 1902 that may be used with any of the delivery catheters or delivery systems disclosed herein to deliver any of the prostheses disclosed herein. The introducer sheath 1902 includes a hub 1904 on the proximal end of the introducer sheath 1902 and an elongate shaft 1908 coupled to the proximal end of the hub 1904. The elongate shaft extends distally from the hub 1904 and may have any desired length and size to accommodate various delivery catheters. The elongate shaft may have any cross-sectional geometry, but in this example the elongate shaft is a cylindrical tube with a circular cross-sectional, and a single circular lumen extending therethrough.

The hub 1904 has a lumen extending through the hub and that is fluidly coupled with the lumen in the elongate shaft. Therefore, fluid introduced from the proximal end of the hub may pass through the hub, through the lumen of the elongate shaft and exit the distal end of the elongate shaft. Thus, when the sheath is disposed in a vessel, blood will flow from the vessel out the hub and therefore the introducer sheath may include a hemostasis valve 1906 to control the backflow. The hemostasis valve is shown in the closed configuration in FIG. 19A.

The hemostasis valve 1906 is an actuatable hemostasis valve that an operator may control to open and close the hemostasis valve as desired. In the open position, the lumen in the hub is open and therefore fluid may be introduced into the introducer sheath and exit the distal end of the sheath, or fluid may be introduced into the sheath from the distal end of the sheath and exit at the proximal end of the hub. Additionally, delivery catheters, delivery systems, dilators, guidewires, or any other device may be inserted into or removed from the introducer sheath when the hemostasis valve is open. When the hemostasis valve is in the closed configuration, the hub lumen is closed and therefore fluid cannot pass past the hemostasis valve and exit out of the proximal end of the hub. Additionally, in any example, the hemostasis valve in the closed position may close tightly enough around a guidewire, delivery catheter, delivery system, dilator, or any other device disposed in the introducer sheath thereby preventing axial movement thereof relative to the introducer sheath.

Optional ports 1910, 1914 (also sometimes referred to as hemo-ports herein) may be coupled to the hub and both may be fluidly coupled with the hemostasis valve 1906. Ports 1910, 1914 may also optionally include a valve such as a one-way, two-way, or other multi-way stopcock 1912, 1916 to control flow in or out of the ports 1910, 1914. The stopcocks may have Luer connectors to facilitate releasable coupling with another medical device such as tubing, a syringe, or other item. A section of tubing may be used to fluidly couple the stopcocks with the hub and hemostasis valve. A pump may be used to actuate the hemostasis valve. Here, syringe 1920 acts as a manually controllable pump to introduce fluid into the hub and actuate the hemostasis valve. The syringe 1920 includes an outer syringe barrel 1924 that holds fluid 1928 such as saline or a gas like nitrogen. An operator may manually actuate syringe plunger 1922 to slidably move rubber seal 1926 through the syringe barrel as shown by arrow 1918 to push the fluid 1928 out of the syringe into the hub. The stopcock 1912 may be actuated into different positions in order to open or close various fluid pathways which is shown in the open position for fluid delivered by the syringe while a second port on the stopcock is shown in the closed position. As fluid is introduced from syringe 1920 through port 1910 into hub 1904, hemostasis valve 1906 will move into the closed position. The second port 1914 may be disposed in the open position to allow fluid from the hub to vent out into the surrounding environment. Once the hemostasis valve has been closed, both ports 1910, 1914 may be closed so that the hemostasis valve remains in the closed position.

FIG. 19B shows the introducer sheath 1902 of FIG. 19A with the hemostasis valve 1906 in the open position, thereby allowing fluid to flow into or out of the introducer sheath or to allow a device to be slidably introduced into or removed from the introducer sheath. Here, the syringe 1920 is actuated in the opposite direction to so that plunger 1922 is retracted proximally as indicated by arrow 1918a to draw fluid 1928 out of hub 1904 to open hemostasis valve 1906. Port 1910 is in the open position to allow the fluid to exit from the hub and also port 1914 may also be in the open position to facilitate fluid removal. Other aspects of FIG. 19B are generally the same as previously described in FIG. 19A. Further details about the actuatable hemostasis valve 1906 are described below.

Figure 20:
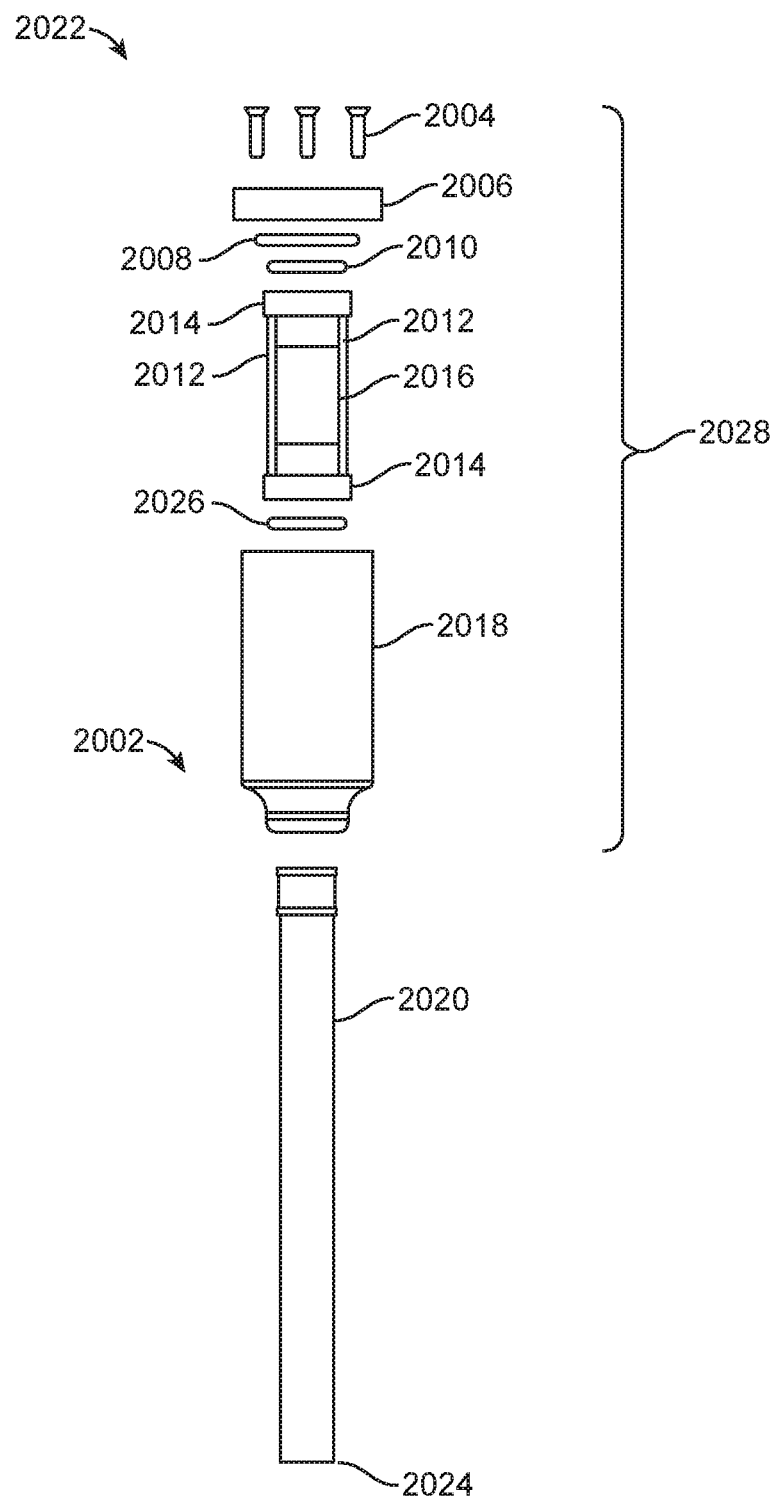
FIG. 20 is an exploded view of the introducer sheath in FIGS. 19A-19B.

FIG. 20 illustrates an exploded view of the introducer sheath 1902 in FIGS. 19A-19B. The introducer sheath 2002 has a proximal end 2022 and a distal end 2024. A hub 2026 is disposed on the proximal end of the introducer sheath and a proximal end of an elongate shaft 2024 is coupled to the distal end of the hub 2026. The elongate shaft extends distally from the hub. The elongate shaft here is a single lumen cylindrically shaped tube having a circular cross-section although other geometries may be used.

The hub 2028 includes fasteners 2004 such as screws, a hub cap 2006, sealing elements 2008, 2010, 2026 such as O-rings, proximal and distal sealing elements 2014, support elements 2012, sealing bladder 2016, and hub body 2018.

The fasteners 2004 secure the hub cap 2006 to the proximal sealing element 2014. Sealing elements 2008, 2010 such as O-rings prevent fluid leakage therebetween. The proximal and distal sealing elements 2014 provide attachment locations for the sealing bladder 2016 where the proximal end of the sealing bladder is coupled to the distal end of the proximal sealing element, and the distal end of the sealing bladder is coupled to the proximal end of the distal sealing element. The sealing bladder may be a cylindrical tube with a single channel extending therethrough and formed form a resilient and flexible material than can expand and collapse. Support elements such as elongate rods 2012 are coupled to the proximal and distal sealing elements to provide a rigid structure so that the proximal and distal sealing elements do not move relative to one another. The assembly of the proximal and distal sealing elements, support elements and the sealing bladder form the actuatable hemostasis valve which can then be inserted into the hub body 2018 leaving an annular space therebetween which can be pressurized with fluid or depressurized. Pressurization of the annular space collapses the bladder closing the hemostasis valve, and depressurizing the annular space allows the bladder to expand thereby opening the hemostasis valve. Sealing element 2026 prevents fluid leakage between the distal sealing element and a distal portion of the hub body. Additional details on the elements of the hub and actuatable hemostasis valve are disclosed below.

Figure 21:
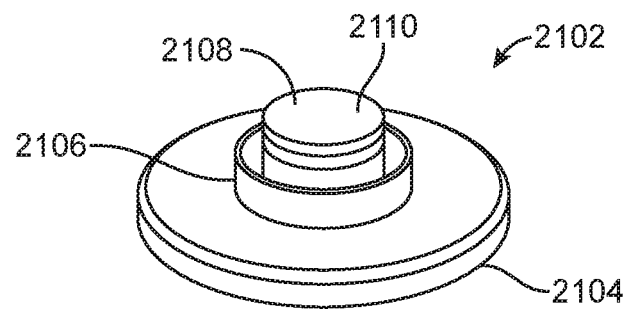
FIG. 21 is a perspective view of a cap.

FIG. 21 shows an example of a cap 2102 that may be disposed at the proximal end of a dilator, such as those seen in FIGS. 26A-26D. The cap includes a disc-shaped circular base 2104, a tapered rim 2106 that extends from the circular base, and also a protruding receptacle 2108 that extends from the circular base. The edges of the circular base are rounded, chamfered, or otherwise broken in order to avoid sharp corners or edges and provide a rim that an operator may easily grasp or manipulate. The rim also provides an enlarged region that serves as a backstop to control over-insertion into the introducer sheath and also may be a visual indicator to help the operator assess insertion of the dilator into the introducer sheath. Additionally, the cap 2102 includes a central channel extending therethrough 2110 and the proximal portion of the channel may include a funnel portion that tapers distally. This facilitates insertion of a guidewire, catheter, delivery system, dilator or any other device into the receptacle and through the introducer sheath. The elongate shaft of the dilator may be coupled to the distal side of the cap.

Figure 22:
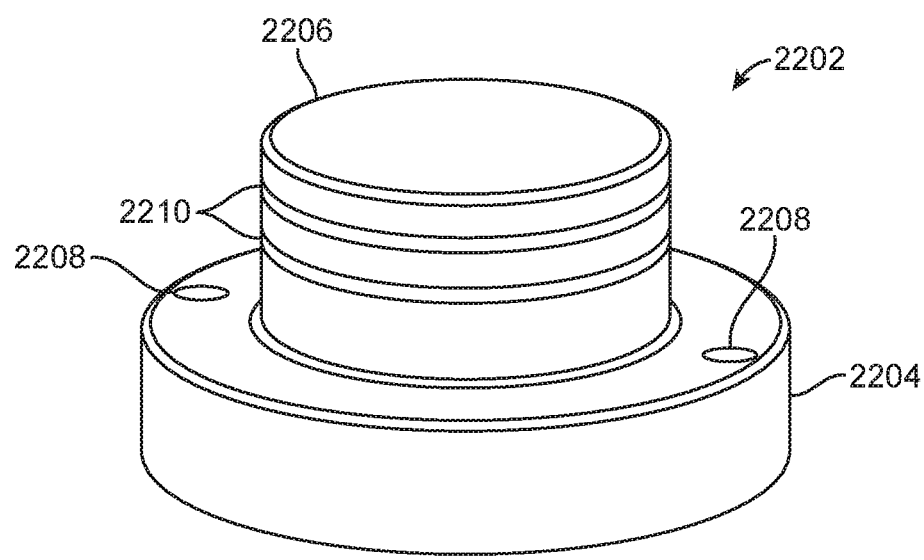
FIG. 22 is a perspective view of a sealing element.

FIG. 22 shows an example of a sealing element 2202. There are two sealing elements, a proximal sealing element and a distal sealing element in the example of FIGS. 19A-19B. Each sealing element includes a circular, disc-like base 2204 with a protruding cylindrical connector portion 2206 extending therefrom. Barbs 2210 allow the ends of the sealing bladder to be coupled to the connector portion. Optionally, in any example barbs may be used in conjunction with or substituted with grooved regions that are sized to receive a filament such as a wire or suture that is tied around the sealing bladder once the sealing bladder is placed over the connector portion. Holes 2208, here two, although any number may be used are sized to receive a cylindrical or any other shaped rod to hold the two sealing elements together and prevent relative movement between the sealing elements thereby forming a rigid structure.

Figure 23:
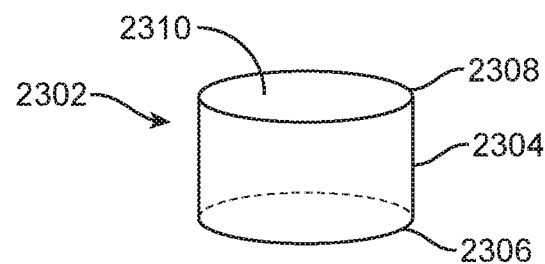
FIG. 23 is an example of a sealing bladder.

FIG. 23 shows an example of a sealing bladder 2302 which is generally a cylindrically shaped resilient and thin walled tube 2304 with proximal and distal ends 2306, 2308 that are coupled to the connector portion of the sealing elements in FIG. 22. The central channel 2310 in the sealing bladder opens and closes to allow fluid, guidewires, catheters, delivery systems, dilators, or other devices to pass through the hub of the introducer sheath into the lumen of the elongate shaft of the introducer sheath.

Figure 24:
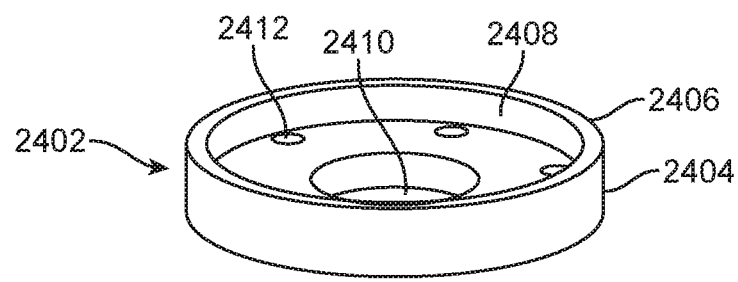
FIG. 24 is an example of a hub cap.

FIG. 24 shows an example of a hub cap 2402 that may be coupled to the hub body to form the proximal-most end of the introducer sheath seen in FIGS. 19A-19B. The hub cap 2402 is a cylindrically shaped cap with a rim 2406 extending outward to form a recessed region 2408 that can fit over the hub body so the two elements can abut with one another. One or more holes through the hub cap allow fasteners such as screws 2004 (seen in FIG. 20) to couple the hub cap with the hub body. Sealing element 2008 prevents fluid leakage therebetween. A central aperture 2410 allows access to the proximal end of the hub so that guidewires, catheters, delivery systems, dilators, or other devices can be inserted into or removed from the introducer sheath. Also, fluids can be introduced into the hub or removed therefrom.

Figure 25:
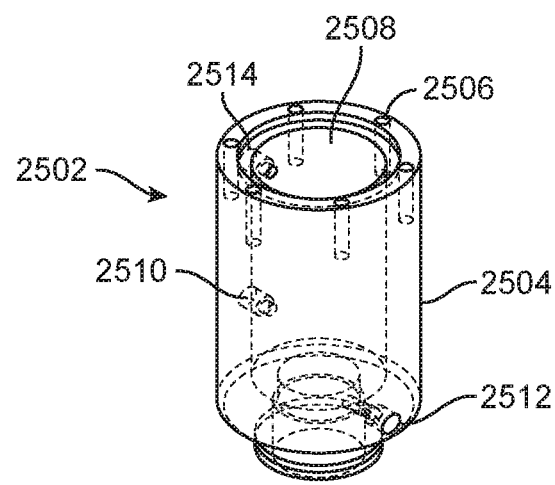
FIG. 25 is an example of a hub body.

FIG. 25 shows an example of a hub body 2502 that houses the actuatable hemostasis valve components described above. The hub body in this example is a cylindrical tube 2504 with a central channel 2508 extending therethrough and that receives the sealing bladder element that is connected to the two sealing elements thereby forming an annular space between the inner surface of the hub body and the outer surface of the sealing bladder. Fluid may be introduced into this annular space to collapse the sealing bladder thereby closing the hemostasis valve, or fluid may be removed from the annular space allowing the sealing bladder to expand and therefore opening the hemostasis valve. Apertures 2510, 2512, 2514 allow fluid to be introduced or removed from various portions of the introducer sheath. For example, aperture 2512 allows fluid to be introduced or removed from the lumen of the elongate shaft of the introducer sheath. This may be used to flush out air from the elongate shaft. Aperture 2514 allows fluid to be introduced into or removed from the annular space between the hub body and the sealing bladder and therefore actuates opening and closing of the hemostasis valve. Aperture 2510 also allows fluid to be introduced into or removed from the annular space between the hub body and the sealing bladder. As fluid is introduced from aperture 2514, air or any other fluid in the annular space may be vented out aperture 2510. And similarly, when fluid is removed from the annular space through aperture 2514, aperture 2510 allows pressure equalization. Tubing with Luer connectors and/or stopcocks may be coupled to the apertures as seen in FIGS. 19A-19B (note only two ports are shown in FIGS. 19A-19B).

Holes 2506 may be threaded to receive fasteners such as screws 2004 shown in FIG. 20, in order to secure the hub cap with the hub body. The elongate shaft (not shown) of the introducer sheath may be coupled to the distal end of the hub body.

Introducer Sheath Delivery

FIGS. 26A-26D illustrate an example of using any of the examples of an introducer sheath disclosed herein.

After a surgical cutdown or Seldinger procedure has been performed to introduce a guidewire into a vessel, a first dilator 2604 may be advanced over the guidewire 2602 through the skin and puncture site 2606 into the vessel 2608 as shown in FIG. 26A.

In FIG. 26B, optionally the first dilator 2602 is removed from the vessel and guidewire and a second larger stepped up size of dilator 2610 is advanced over the guidewire through the skin and puncture site 2606 into the vessel 2608. This process of using several other larger dilators to increase the puncture and vascular access site size may be repeated as needed. After the puncture site and vascular access site have been dilated to a desired size, the dilator may be removed from the vessel and the guidewire. Any of the dilators disclosed herein may include the cap described in FIG. 21 on a proximal end of the dilator shaft to provide a surface that an operator may grasp and manipulate, and that serves as a backstop and visual indicator, as well as a tapered or funneled entry to facilitate introduction of guidewires or other devices into the dilator.

Figure 26C:
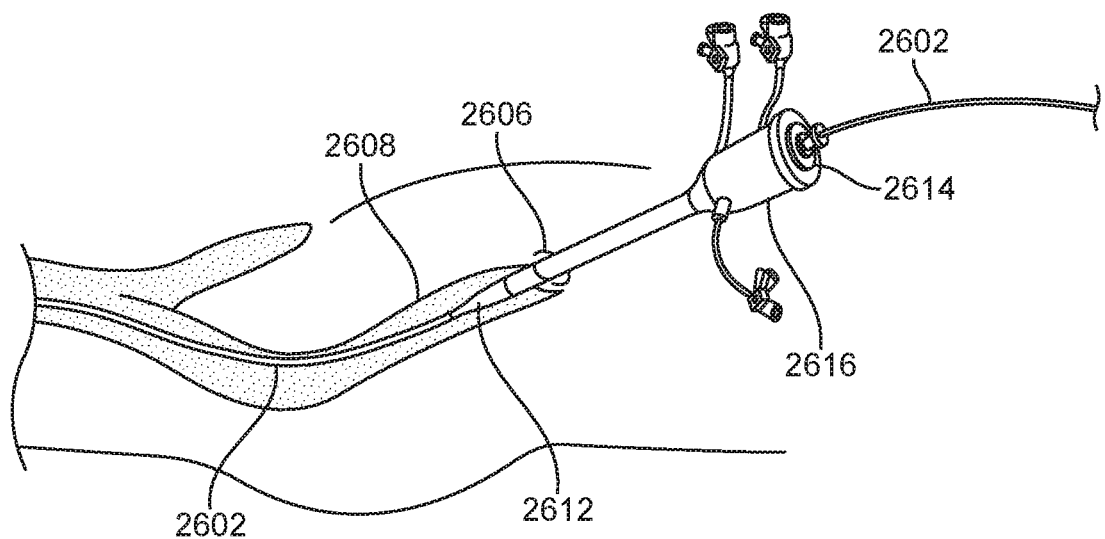

FIG. 26C illustrates loading of an introducer sheath 2616 over the guidewire 2602. The introducer sheath 2616 may be any of the introducer sheaths disclosed herein and it may have a dilator 2614 or obturator disposed in the introducer sheath lumen to help provide column stiffness so that the introducer sheath may be advanced over the guidewire through the skin and puncture site 2606 and into the vessel 2608. The distal end of the dilator or obturator may be tapered 2612 to facilitate introduction of the introducer sheath into the vessel.

Figure 26D:
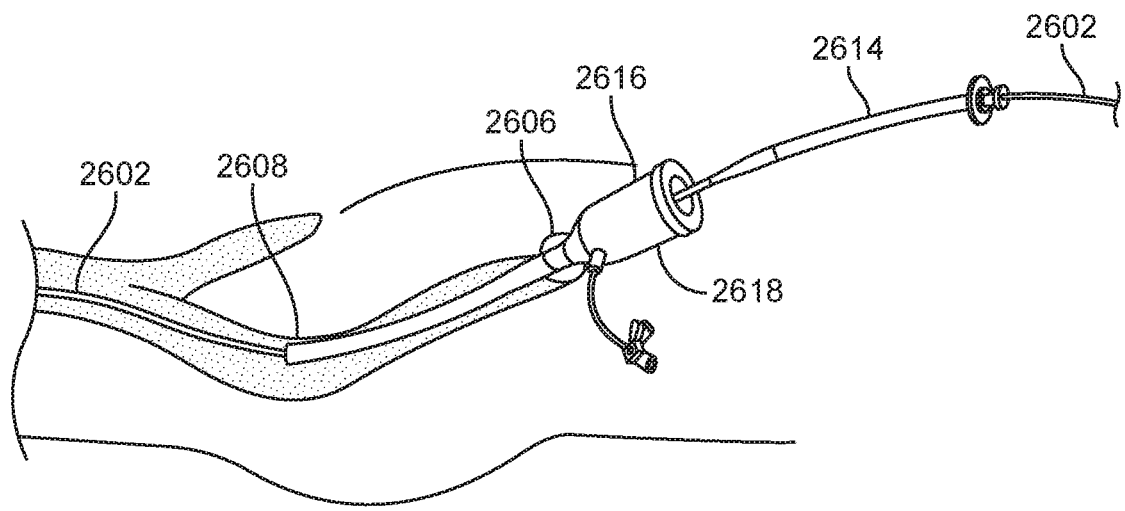

FIG. 26D shows that the introducer sheath 2616 is advanced distally into the vessel so that the introducer hub 2618 is adjacent the skin and puncture site 2606. The introducer sheath may be anchored in position with a suture, tape, or any other technique known in the art. The dilator 2614 or obturator is then retracted out of the vessel, out of the introducer sheath and removed from the guidewire. This leaves the introducer sheath and guidewire in the vessel.

Any catheter, delivery system or other instrument such as any of the delivery catheters and delivery systems disclosed herein carrying any of the prostheses disclosed herein can then be loaded over the guidewire and advanced through the sheath into the vessel. The delivery catheter can then be advanced to a target treatment region where the prosthesis is then deployed. For example, a prosthetic mitral valve may be carried by a prosthesis delivery catheter and delivered to the native mitral valve where the prosthetic mitral valve is deployed to repair a diseased or damaged native mitral valve, using any of the previously described methods disclosed herein. The hemostasis valve may be actuated into an open or closed position by introducing fluid or removing fluid from the hub as previously described, and as needed. Once the procedure is complete, the guidewire and sheath may be removed from the patient.

Purging Straw

An optional purging straw may be used to help flush the prosthesis and capsule on the delivery catheter to remove air and wet the device before introduction into the patient's vascular system.

Figure 27:
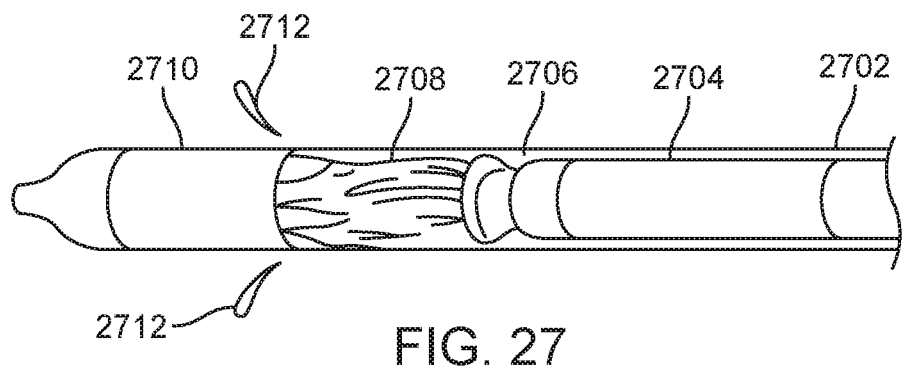
FIG. 27 illustrates an example of a purging straw.

FIG. 27 shows a purging straw 2702 disposed over a delivery catheter 2704 carrying a prosthesis 2708 in the capsule 2710 of the delivery catheter. The delivery catheter, delivery system, prosthesis, and capsule may be any of those described herein. The purging straw 2702 is an elongate cylindrical shaft having a lumen extending therethrough. A connector such as a Luer hub (not shown) may be disposed on the proximal end of the purging straw to allow connection to a syringe, tubing or another device. Fluid is introduced into the purging straw lumen 2706 and this fills all the spaces in the capsule and around the prosthesis thereby driving out air 2712 or any other unwanted fluids from the device. The purging straw may be used to flush the delivery catheter capsule and prosthesis prior to insertion into an introducer sheath. After the flushing is complete, the delivery catheter with prosthesis and purging straw disposed thereover may be inserted into an introducer sheath in the patient.

Figure 28A:
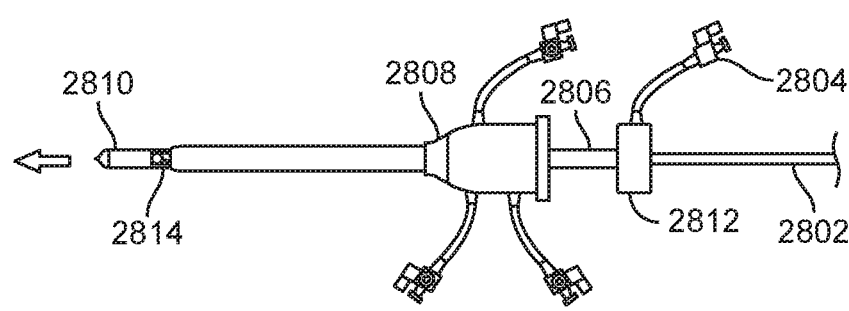
FIGS. 28A-28C illustrate an example of an introducer sheath with a purging straw and delivery catheter.
Figure 28B:
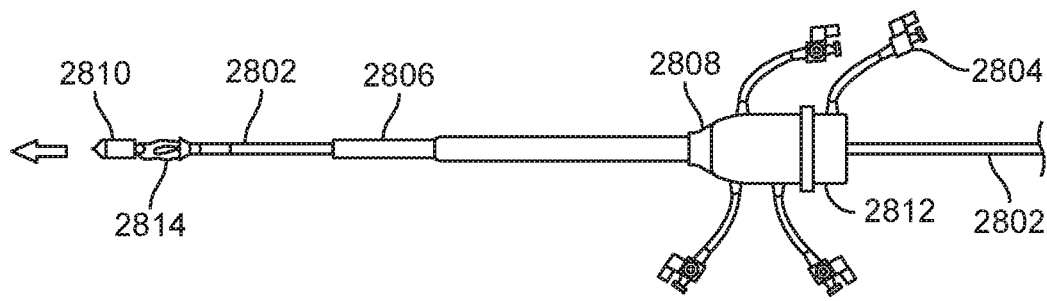
Figure 28C:
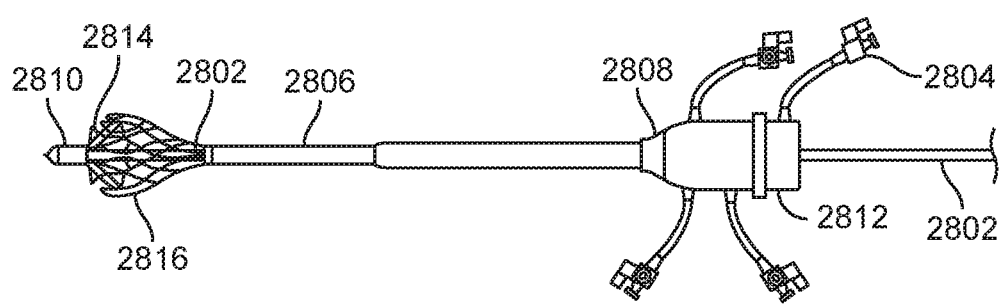

FIGS. 28A-28C show how a delivery catheter, purging straw and introducer sheath may be used together. FIG. 28A shows an introducer sheath 2808 with a purging straw 2806 disposed in the sheath 2808 and a prosthesis delivery catheter 2802 carrying a prosthesis 2814, disposed in the purging straw 2806. This is illustrated outside the body for simplicity but one of skill in the art would appreciate that this may be performed in a patient similarly as described above in the example. The introducer sheath, purging straw, prosthesis delivery catheter and prosthesis may be any of those described herein. After flushing outside the introducer sheath and outside the patient, purging straw with delivery catheter disposed in the purging straw is partially advanced into the introducer sheath such that the distal portion of the capsule 2810 on the delivery catheter is distal of the purging straw and past the distal end of the introducer sheath, as indicated by the arrow. Purging may be completed before inserting the purging straw and delivery catheter into the introducer sheath by introducing a fluid into the purging straw via tubing coupled to a port 2804 (here a stopcock with a Luer connector) on the hub 2812 of the purging straw. Fluid flows through the lumen of the purging straw to flush out air from the capsule 2810 holding the prosthesis 2814 and any air that may be entrapped in the prosthesis.

In FIG. 28B the purging straw 2806 is advanced further distally into the introducer sheath 2808 and the delivery catheter 2802 is also advanced further distally into the purging straw 2806 and into the introducer sheath 2808 as indicated by the arrow. The delivery catheter is advanced to a target treatment site such as a native mitral valve and the capsule 2810 is opened up to allow the prosthesis 2814 to start to self-expand. The prosthesis is then delivered, and the purging straw and introducer sheath may be withdrawn from the patient. Again, note the surrounding anatomy and guidewire are not illustrated in FIG. 28B.

In the situation where the prosthesis does not deploy correctly, an optional funnel may be used to help capture and resheath the prosthesis. In FIG. 28C, the prosthesis 2814 is partially deployed but the operator determines that deployment is not optimal and therefore the operator may recapture and resheath the prosthesis for a second attempt at a better deployment. Here, the purging straw 2806 may optionally include a self-expanding or otherwise expandable funnel 2816 that tapers from its distal end to its proximal end. The funnel may be a woven mesh of filaments or it may be a series of open or closed cells that have been cut from tubing or a flat sheet rolled into a tube. This funnel is disposed on the distal end of the purging straw, and facilitates recapture of the partially deployed prosthesis 2814 and allows the prosthesis to be recaptured and resheathed in the capsule of the delivery system. The funnel also helps prevent edges of the prosthesis from catching on other portions of the patient anatomy, delivery catheter, introducer sheath or purging straw and thus helps prevent deformation of the prosthesis. The elongate shaft of the introducer sheath may serve as a constraining member to prevent self-expansion of the funnel when it is disposed in the introducer sheath lumen. When the funnel is needed, the purging straw may be pushed distally out of the introducer sheath to unconstrain the funnel and allow it to self-expand. Once the prosthesis has been recaptured and resheathed in the capsule, the funnel may also be collapsed by retracting the funnel into the introducer sheath. The device may be repositioned, and deployment may be attempted again as desired.

The actuatable hemostasis valve may be actuated between the open and closed positions as previously described to allow or prevent fluid flow through the introducer sheath as well as anchoring or allowing movement of the purging straw and/or delivery catheter through the introducer sheath.

FIGS. 29A-29F illustrate several other examples of an actuatable hemostasis valve in an introducer sheath.

Figure 29A:
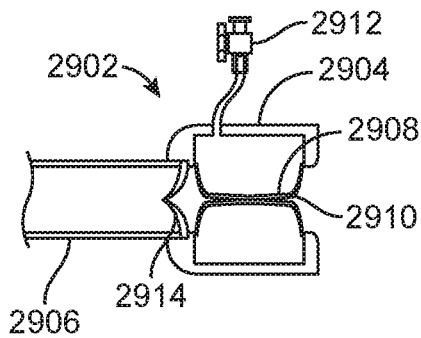
FIGS. 29A-29F show several examples of an actuatable hemostasis valve in an introducer sheath.

FIG. 29A shows another example of an introducer sheath 2902 with an actuatable hemostasis valve. The introducer sheath 2902 includes an elongate tubular member 2906 coupled to a proximal hub 2904. The elongate tubular member 2906 has a lumen extending therethrough. A bladder 2908 may be actuated into an expanded or collapsed position by introducing fluid in the space surrounding the bladder to open or close the port 2910 on the hub thereby opening or closing the hemostasis valve and constraining movement of any devices disposed therein. An optional distal valve 2914 such as a slit valve, duckbill valve or flap valve may also be included to further ensure a tight seal. The distal valve may have two opposable leaflets or it may be any other valve. Moreover, an optional spring (not shown) may be coupled to the bladder to bias the bladder into either the open or closed position. Fluid may be introduced or removed from the hub to actuate the hemostasis valve between open and closed positions via port 2912 which may have a one-way or multi-way stopcock with Luer connector.

Figure 29B:
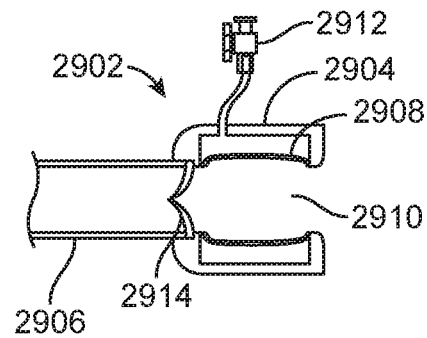

FIG. 29B shows the introducer sheath with hemostasis valve of FIG. 29A in the open position. Here, fluid has been removed from the space surrounding the bladder thereby allowing the bladder to expand and opening up channel 2910 so that fluid can flow through the hub and devices may be positioned therein. Optional distal valve 2914 may be biased in the closed position to prevent blood from leaking out of the introducer sheath. As mentioned previously, an optional spring (not shown) coupled to the bladder may be biased to help open the hemostasis valve.

Figure 29C:
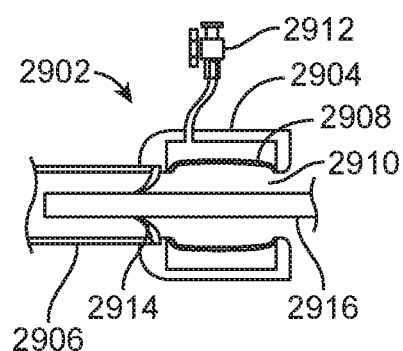

FIG. 29C shows the introducer sheath with hemostasis valve of FIG. 29B in the open position and with a device 2916 disposed across the actuatable hemostasis valve and past the distal valve 2914. The distal valve 2914 closes against the device 2916 to prevent fluid flow therepast. The device 2916 may be anything including a guidewire, a purge straw, a delivery catheter, delivery system, or other elongate shaft. Any of the delivery catheters, delivery systems, purge straws, prostheses, etc. disclosed herein may be used with this introducer sheath. Other aspects of FIG. 29C are generally the same as described with respect to FIG. 29C.

Figure 29D:
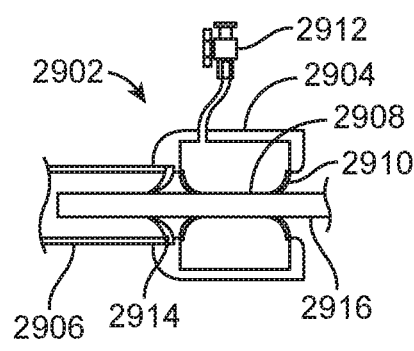

FIG. 29D shows the introducer sheath with hemostasis valve of FIG. 29A in the closed position and with a device 2916 disposed across the actuatable hemostasis valve and past the distal valve 2914. Both the hemostasis valve 2908 and the distal valve 2914 prevent fluid flow out channel 2910. Additionally, in the closed position both valves 2908, 2914 abut the device 2916 and may limit or prevent axial movement thereof.

Figure 29E:
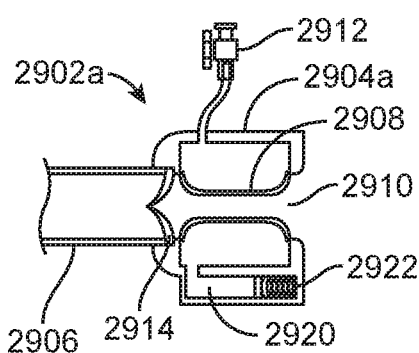

FIG. 29E shows another example of an introducer sheath with an actuatable hemostasis valve in the open position. Here, introducer sheath 2902a includes a proximal hub 2904a coupled to an elongate shaft 2906 having a lumen extending therethrough. The hub 2904a includes a bladder 2908 that may expand and collapse to open and close channel 2910. An optional distal valve 2914 may also be used to help prevent backflow of fluid through the sheath. The hemostasis valve is substantially the same as that described in FIGS. 29A-29D above in that fluid may be introduced around the bladder via port 2912 to collapse and close the hemostasis valve, or fluid may be removed from around the bladder via port 2912 to open the channel 2910. Closing the channel may also help prevent axial movement of devices through the channel. An optional spring (not shown) may be coupled to the bladder to bias it into an open or closed position as desired. An additional reservoir 2920 may be coupled to the hub and fluidly coupled to the space surrounding the bladder 2908. A spring with a plunger 2922 drives fluid out of reservoir 2920 into the space surrounding the bladder, or drives fluid out of the space surrounding the bladder back into the reservoir 2920, thereby helping to control bladder compliance.

Figure 29F:
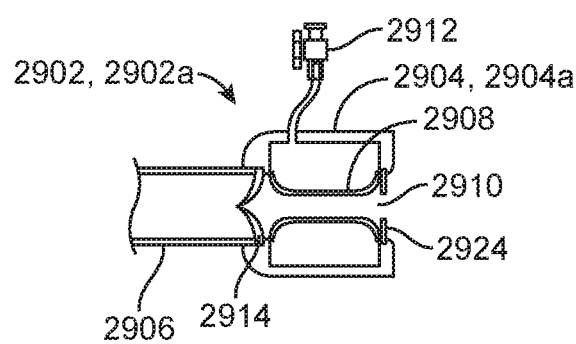

FIG. 29F shows another example an introducer sheath with an actuatable hemostasis valve. The introducer sheath 2902, 2902a may be any of the introducer sheaths disclosed herein and it includes an elongate shaft 2906 with a lumen extending therethrough, and that is coupled to the proximal hub 2904, 2904a. The actuatable hemostasis valve 2908 is a bladder that expands and contracts thereby opening and closing channel 2910. Fluid is introduced into the space surrounding the bladder via port 2912 to collapse the bladder and close channel 2910. Fluid may be removed from the space surrounding the bladder allowing the bladder to expand and open channel 2910. A spring (not shown) may be coupled to the bladder to bias it into the expanded or collapsed configuration. An optional distal valve 2914 may be included such as a valve with flaps or leaflets. Also optionally this example or any example of hemostasis valve may also include a proximal seal 2924 to help seal the proximal end of the introducer sheath. The proximal seal may be a washer type valve that is fully or partially closed, or it may be fully or partially open. It may help minimize blood loss during catheter insertion as the seal seals around the device inserted therepast. Other aspects of the introducer sheath are generally the same as in any of FIGS. 29A-29E.

Notes and Examples

The following, non-limiting examples, detail certain aspects of the present subject matter to solve the challenges and provide the benefits discussed herein, among others.

Example 1 is an introducer sheath that comprises an elongate shaft having a proximal end, a distal end, and a lumen extending therebetween; a hub coupled to the proximal end of the elongate shaft, the hub having a lumen extending therethrough, and the hub lumen fluidly coupled with the elongate shaft lumen; and an actuatable hemostasis valve disposed in the hub, the actuatable hemostasis valve actuatable between an open configuration and a closed configuration, wherein in the open configuration the actuatable hemostasis valve is disposed in an expanded configuration that allows fluid to flow past the actuatable hemostasis valve, and wherein in the closed configuration the actuatable sealing element is disposed in a collapsed configuration that seals the hub lumen and prevents fluid from flowing past the actuatable hemostasis valve.

Example 2 is the introducer of Example 1, further comprising a purging straw slidably disposed in the hub lumen, the purging straw comprising an elongate shaft with a proximal end, a distal end, and a lumen extending therebetween.

Example 3 is the introducer of any of Examples 1-2, wherein in the closed configuration the actuatable hemostasis valve is in the collapsed configuration and is configured to collapse against the purging straw and prevent axial movement of the purging straw relative to the hub.

Example 4 is the introducer of any of Examples 1-3, wherein in the closed configuration the actuatable hemostasis valve is in the collapsed configuration and is configured to collapse against a catheter disposed in the hub lumen and prevent axial movement of the catheter relative to the hub.

Example 5 is the introducer of any of Examples 1-4, wherein the purging straw comprises a stopping element coupled to the proximal end of the purging straw, the stopping element configured to limit advancement of the purging straw into the hub lumen.

Example 6 is the introducer of any of Examples 1-5, wherein the purging straw comprises a flared funnel coupled to a distal end of the purging straw.

Example 7 is the introducer of any of Examples 1-6, wherein the flared funnel is self-expanding.

Example 8 is the introducer of any of Examples 1-7, wherein the flared funnel comprises a coating or cover coupled thereto.

Example 9 is the introducer of any of Examples 1-8, wherein the hub comprises one or more ports fluidly coupled therewith, the one or more ports configured to allow fluid to enter or exit the hub.

Example 10, is the introducer of any of Examples 1-9, wherein the one or more ports comprise three ports, the first port fluidly coupled with the actuatable hemostasis valve and configured to allow introduction of a fluid into the actuatable hemostasis valve, the second port fluidly coupled with the actuatable hemostasis valve and configured to allow fluid to vent out of the actuatable hemostasis valve, and the third port fluidly coupled with the hub lumen and configured to introduce fluid into the hub lumen or to allow fluid to be removed from the hub lumen.

Example 11 is the introducer of any of Examples 1-10, further comprising a dilator with a tapered distal tip, the dilator slidably disposed through the elongate shaft lumen.

Example 12 is the introducer of any of Examples 1-11, wherein the actuatable hemostasis valve comprises a sealing bladder having an expanded configuration and a collapsed configuration, wherein in the expanded configuration the elongate shaft lumen is patent, and wherein in the collapsed configuration the elongate shaft lumen is obstructed.

Example 13 is the introducer of any of Examples 1-12, wherein the actuatable hemostasis valve comprises a plurality of support elements, a proximal sealing element, a distal sealing element and a sealing bladder, and wherein the hub comprises a hub body and a hub cap, wherein opposite ends of the sealing bladder are coupled to the upper and lower sealing elements, wherein the plurality of support elements are disposed between the upper and lower sealing elements, wherein the actuatable hemostasis valve is disposed in the hub body, and wherein the hub cap is coupled to a proximal end of the hub body.

Example 14 is a system for introducing a medical device into a patient, said system comprising: an introducer sheath comprising an elongate shaft, a hub coupled to a proximal end of the elongate shaft, and an actuatable hemostasis valve disposed in the hub, the actuatable hemostasis valve actuatable between an open configuration and closed configuration, wherein in the open configuration fluid is configured to flow past the actuatable hemostasis valve, and wherein in the closed configuration the fluid is prevented from flowing past the actuatable hemostasis valve.

Example 15 is the system of Example 14, further comprising a purging straw slidably disposed in the introducer sheath, wherein the purging straw comprises an elongate shaft with a lumen extending therethrough.

Example 16 is the system of any of Examples 14-15, wherein the actuatable hemostasis valve in the closed configuration engages the purging straw and prevents axial movement of the purging straw relative to the intruder sheath.

Example 17 is the system of any of Examples 14-16, further comprising a dilator with a tapered distal tip slidably disposed in the introducer sheath.

Example 18 is the system of any of Examples 14-17, further comprising a delivery catheter slidably disposed in the introducer sheath.

Example 19 is the system of any of Examples 14-18, wherein the delivery catheter comprises a delivery catheter carrying a prosthetic cardiac valve.

Example 20 is the system of any of Examples 14-19, wherein the purging straw comprises a stopping element coupled to a proximal end of the purging straw, the stopping element configured to limit advancement of the purging straw into the introducer sheath.

Example 21 is the system of any of Examples 14-20, wherein the purging straw comprises a flared funnel coupled to a distal end of the purging straw.

Example 22 is the system of any of Examples 14-21, wherein the flared funnel is self-expanding.

Example 23 is the system of any of Examples 14-22, wherein the flared funnel comprises a coating or cover coupled thereto.

Example 24 is the system of any of Examples 14-23, wherein the hub comprises one or more ports fluidly coupled therewith, the one or more ports configured to allow fluid to enter or exit the hub.

Example 25 is the system of any of Examples 14-24, wherein the one or more ports comprise three ports, the first port fluidly coupled with the actuatable hemostasis valve and configured to allow introduction of a fluid into the actuatable hemostasis valve, the second port fluidly coupled with the actuatable hemostasis valve and configured to allow fluid to vent out of the actuatable hemostasis valve, and the third port fluidly coupled with the hub and configured to introduce fluid into the hub or to allow fluid to be removed from the hub.

Example 26 is the system of any of Examples 14-25, wherein the actuatable hemostasis valve comprises a sealing bladder having an expanded configuration and a collapsed configuration, wherein in the expanded configuration fluid is configured to flow past the actuatable hemostasis valve, and wherein in the collapsed configuration fluid is obstructed from flowing past the actuatable hemostasis valve.

Example 27 is a method of introducing a medical device into a patient, said method comprising: inserting an introducer sheath into a blood vessel; slidably disposing an elongate shaft into the introducer sheath; advancing the medical device through the introducer sheath to a target treatment area; actuating an actuatable hemostasis valve in the introducer sheath to collapse against the elongate shaft thereby preventing fluid from flowing past the actuatable hemostasis valve; performing a treatment on the patient at the target treatment area with the medical device; actuating the actuatable hemostasis valve in the introducer sheath to expand away from the elongate shaft thereby allowing fluid to flow past the actuatable hemostasis valve; and removing the elongate shaft from the introducer sheath.

Example 28 is the method of Example 27, wherein the actuatable hemostasis valve comprises a sealing bladder and wherein actuating the actuatable hemostasis valve to collapse against the elongate shaft comprises collapsing the sealing bladder around the elongate shaft thereby constraining axial movement of the elongate shaft relative to the introducer sheath.

Example 29 is the method of any of Examples 27-28, wherein the actuatable hemostasis valve comprises a sealing bladder and wherein actuating the actuatable hemostasis valve to expand away from the elongate shaft comprises expanding the sealing bladder away from the elongate shaft thereby allowing axial movement of the elongate shaft relative to the introducer sheath.

Example 30 is the method of any of Examples 27-29, wherein the elongate shaft comprises a purging straw, the method further comprising filling the purging straw with a liquid and purging a gas out of the purging straw.

Example 31 is the method of any of Examples 27-30, wherein slidably disposing the elongate shaft comprises advancing the purging straw until a stopping element on a proximal end of the purging straw abuts a proximal portion of the introducer sheath.

Example 32 is the method of any of Examples 27-31, further comprising radially expanding a flared funnel on a distal end of the purging straw to facilitate recapture of the medical device.

Example 33 is the method of any of Examples 27-32, wherein the introducer sheath comprises a hub coupled to a proximal end of the introducer sheath, and wherein the actuatable hemostasis valve comprises a sealing bladder in the hub, and wherein actuating the actuatable hemostasis valve to collapse against the elongate shaft comprises introducing a fluid into the hub to collapse the sealing bladder.

Example 34 is the method of any of Examples 27-33, wherein actuating the actuatable hemostasis valve to collapse against the elongate shaft further comprises venting a fluid out of the hub.

Example 35 is the method of any of Examples 27-34, wherein the introducer sheath comprises a hub coupled to a proximal end of the introducer sheath, and wherein the actuatable hemostasis valve comprises a sealing bladder in the hub, and wherein actuating the actuatable hemostasis valve in the introducer sheath to expand away from the elongate shaft comprises removing fluid from the hub.

Example 36 is the method of any of Examples 27-35, wherein the introducer sheath comprises a hub coupled to a proximal end of the introducer sheath, the method further comprising purging the introducer sheath by introducing a fluid into the hub.

Example 37 is the method of any of Examples 27-36, further comprising slidably disposing a dilator through the introducer sheath.

Example 38 is the method of any of Examples 27-37, wherein the medical device comprises a prosthetic cardiac valve.

Example 39 is the method of any of Examples 27-38, wherein the elongate shaft is a delivery catheter carrying the medical device.

In Example 40, the apparatuses, systems or methods of any one or any combination of Examples 1-39 can optionally be configured such that all elements or options recited are available to use or select from.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

The invention claimed is:

1. An introducer sheath comprising:
   an elongate shaft having a proximal end, a distal end, and a lumen extending therebetween;
   a hub coupled to the proximal end of the elongate shaft, the hub having a lumen extending therethrough, and the hub lumen fluidly coupled with the elongate shaft lumen;
   an actuatable hemostasis valve disposed in the huh forming an annular region therebetween, the annular region fluidly isolated from the lumen in the hub and the lumen in the elongate shaft, the actuatable hemostasis valve actuatable between an open configuration and a closed configuration,
   wherein in the open configuration the actuatable hemostasis valve is disposed in an expanded configuration that allows fluid to flow past the actuatable hemostasis valve, and
   wherein in the closed configuration the actuatable hemostasis valve is disposed in a collapsed configuration that seals the hub lumen and prevents fluid from flowing past the actuatable hemostasis valve; and
   a single fluid port fluidly coupled with the annular region,
   wherein introduction of a fluid into the single fluid port fills the annular region with the fluid thereby moving the actuatable hemostasis valve into the closed configuration, and
   wherein removal of the fluid from the annular region via the single fluid port moves the actuatable hemostasis valve into the open configuration;
   wherein the annular region of the actuatable hemostasis valve is configured to remain in the open configuration when not filled with fluid.

2. The sheath of claim 1, further comprising a purging straw slidably disposed in the hub lumen, the purging straw comprising an elongate shaft with a proximal end, a distal end, and a lumen extending therebetween.

3. The sheath of claim 2, wherein in the closed configuration the actuatable hemostasis valve is in the collapsed configuration and is configured to collapse against the purging straw and prevent axial movement of the purging straw relative to the hub.

4. The sheath of claim 2, wherein in the closed configuration the actuatable hemostasis valve is in the collapsed configuration and is configured to collapse against a catheter disposed in the hub lumen and prevent axial movement of the catheter relative to the hub.

5. The sheath of claim 2, wherein the purging straw comprises a stopping element coupled to the proximal end of the purging straw, the stopping element configured to limit advancement of the purging straw into the hub lumen.

6. The sheath of claim 2, wherein the purging straw comprises a flared funnel coupled to a distal end of the purging straw.

7. The sheath of claim 6, wherein the flared funnel is self-expanding and comprises a coating or a cover coupled thereto.

8. The sheath of claim 1, wherein the actuatable hemostasis valve is biased to the open configuration.

9. The sheath of claim 1, further comprising a dilator with a tapered distal tip, the dilator slidably disposed through the elongate shaft lumen.

10. The sheath of claim 1, wherein the actuatable hemostasis valve comprises a sealing bladder having an expanded configuration and a collapsed configuration, wherein in the expanded configuration the elongate shaft lumen is patent, and wherein in the collapsed configuration the elongate shaft lumen is obstructed.

11. The sheath of claim 1, wherein the actuatable hemostasis valve comprises a plurality of support elements, a proximal sealing element, a distal sealing element and a sealing bladder, and
wherein the hub comprises a hub body and a hub cap,
wherein opposite ends of the sealing bladder are coupled to the proximal and the distal sealing elements,
wherein the plurality of support elements are disposed between the proximal and the distal sealing elements,
wherein the actuatable hemostasis valve is disposed in the hub body, and
wherein the hub cap is coupled to a proximal end of the hub body.

12. The sheath of claim 1, further comprising a distal valve connected to the hub distal of the actuatable hemostasis valve, the distal valve biased to a closed position.

13. The sheath of claim 1, further comprising an external fluid source coupled to the single fluid port, the external fluid source located outside of the hub.

14. A system for introducing a medical device into a patient, said system comprising:
an introducer sheath comprising an elongate shaft, a hub coupled to a proximal end of the elongate shaft, and an actuatable hemostasis valve disposed in the hub forming an annular region therebetween,
the annular region fluidly isolated from the elongate shaft,
the actuatable hemostasis valve actuatable between an open configuration and closed configuration, wherein in the open configuration fluid is configured to flow past the actuatable hemostasis valve, and wherein in the closed configuration the fluid is prevented from flowing past the actuatable hemostasis valve,
a single fluid port fluidly coupled with the annular region, and
an external pressurization device coupled to the hub via a fluid line at the single fluid port to introduce and remove fluid into the single fluid port,
wherein introduction of a fluid into the single fluid port fills the annular region with the fluid thereby moving the actuatable hemostasis valve into the closed configuration, and
wherein removal of the fluid from the annular region via the single fluid port moves the actuatable hemostasis valve into the open configuration.

15. The system of claim 14, further comprising a purging straw slidably disposed in the introducer sheath, wherein the purging straw comprises an elongate shaft with a lumen extending therethrough.

16. The system of claim 15, wherein the actuatable hemostasis valve in the closed configuration engages the purging straw and prevents axial movement of the purging straw relative to the introducer sheath.

17. The system of claim 15, wherein the purging straw comprises a stopping element coupled to a proximal end of the purging straw, the stopping element configured to limit advancement of the purging straw into the introducer sheath.

18. The system of claim 15, wherein the purging straw comprises a flared funnel coupled to a distal end of the purging straw.

19. The system of claim 18, wherein the flared funnel is self-expanding.

20. The system of claim 18, wherein the flared funnel comprises a coating or cover coupled thereto.

21. The system of claim 14, further comprising a dilator with a tapered distal tip slidably disposed in the introducer sheath.

22. The system of claim 14, further comprising a delivery catheter slidably disposed in the introducer sheath.

23. The system of claim 22, wherein the delivery catheter comprises a delivery catheter carrying a prosthetic cardiac valve.

24. The system of claim 14, wherein the actuatable hemostasis valve comprises a sealing bladder having an expanded configuration and a collapsed configuration, wherein in the expanded configuration fluid is configured to flow past the actuatable hemostasis valve, and wherein in the collapsed configuration fluid is Obstructed from flowing past the actuatable hemostasis valve.

25. The sheath of claim 14, further comprising a distal valve connected to the hub distal of the actuatable hemostasis valve, the distal valve comprising a duckbill valve or flap valve that is biased to a closed position.

26. The sheath of claim 14, wherein the external pressurization source comprises a manually operated syringe.

27. A method of introducing a medical device into a patient, said method comprising
inserting an introducer sheath into a blood vessel;
advancing an elongate shaft of the medical device into an actuatable hemostasis valve in a hub of the introducer sheath, the actuatable hemostasis valve being defaulted to an open state;
slidably disposing the elongate shaft into a lumen in the introducer sheath;
advancing the medical device through the actuatable hemostasis valve and the introducer sheath to a target treatment area;
actuating the actuatable hemostasis valve to collapse against the elongate shaft thereby preventing fluid from flowing past the actuatable hemostasis valve, wherein an annular region is disposed between the actuatable hemostasis valve and the hub, the annular region fluidly isolated from the lumen,
wherein actuating the actuatable hemostasis valve comprises introducing a fluid into a single fluid port fluidly coupled with the annular region thereby filling the annular region with the fluid and moving the actuatable hemostasis valve into a closed configuration;
performing a treatment on the patient at the target treatment area with the medical device;

actuating the actuatable hemostasis valve in the introducer sheath to expand away from the elongate shaft thereby allowing fluid to flow past the actuatable hemostasis valve, wherein actuating the actuatable hemostasis valve to expand away comprises removing the fluid from the annular region via the single fluid port thereby moving the actuating hemostasis valve into an open configuration; and removing the elongate shaft from the introducer sheath.

28. The method of claim 27, wherein the actuatable hemostasis valve comprises a sealing bladder and wherein actuating the actuatable hemostasis valve to collapse against the elongate shaft comprises collapsing the sealing bladder around the elongate shaft thereby constraining axial movement of the elongate shaft relative to the introducer sheath.

29. The method of claim 27, wherein the actuatable hemostasis valve comprises a sealing bladder and wherein actuating the actuatable hemostasis valve to expand away from the elongate shaft comprises expanding the sealing bladder away from the elongate shaft thereby allowing axial movement of the elongate shaft relative to the introducer sheath.

30. The method of claim 27, wherein the elongate shaft comprises a purging straw, the method further comprising filling the purging straw with a liquid and purging a gas out of the purging straw.

31. The method of claim 30, wherein slidably disposing the elongate shaft comprises advancing the purging straw until a stopping element on a proximal end of the purging straw abuts a proximal portion of the introducer sheath.

32. The method of claim 30, further comprising radially expanding a flared funnel on a distal end of the purging straw to facilitate recapture of the medical device.

33. The method of claim 27, further comprising purging the introducer sheath by introducing a fluid into the hub.

34. The method of claim 27, further comprising slidably disposing a dilator through the introducer sheath.

35. The method of claim 27, wherein the medical device comprises a prosthetic cardiac valve.

36. The method of claim 27, wherein the elongate shaft is a delivery catheter carrying the medical device.

37. The method of claim 27, further comprising advancing the medical device through a distal valve disposed in the hub distal of the actuatable hemostasis valve.

38. The method of claim 27, further comprising:

operating an external pressurization source coupled to the single fluid port to collapse and expand the actuatable hemostasis valve, wherein:

in a closed configuration the actuatable hemostasis valve is pressurized with actuation fluid from the external pressurization source; and in an open configuration the actuatable hemostasis valve is free of actuation fluid.

* * * * *